(12) United States Patent
Yaron et al.

(10) Patent No.: US 8,313,454 B2
(45) Date of Patent: Nov. 20, 2012

(54) FLUID DRAINAGE DEVICE, DELIVERY DEVICE, AND ASSOCIATED METHODS OF USE AND MANUFACTURE

(75) Inventors: Ira Yaron, Har Adar (IL); Oded Nissan, Modiin (IL); Gal Goren, Reut (IL)

(73) Assignee: Optonol Ltd., Neve Ilan (IL)

( * ) Notice: Subject to any disclaimer, the term of this patent is extended or adjusted under 35 U.S.C. 154(b) by 314 days.

(21) Appl. No.: 12/748,149

(22) Filed: Mar. 26, 2010

(65) Prior Publication Data

US 2010/0274259 A1    Oct. 28, 2010

Related U.S. Application Data

(60) Continuation-in-part of application No. 12/691,176, filed on Jan. 21, 2010, now abandoned, which is a continuation of application No. 11/952,819, filed on Dec. 7, 2007, now Pat. No. 7,670,310, which is a continuation of application No. 10/314,324, filed on Dec. 9, 2002, now abandoned, which is a division of application No. 09/729,050, filed on Dec. 4, 2000, now Pat. No. 6,510,600, which is a division of application No. 08/975,386, filed on Nov. 20, 1997, now Pat. No. 6,203,513.

(51) Int. Cl.
*A61B 19/00* (2006.01)
*A61F 11/00* (2006.01)
(52) U.S. Cl. .................. 604/8; 604/9; 606/108
(58) Field of Classification Search .............. 604/8, 9, 604/264; 606/108
See application file for complete search history.

(56) References Cited

U.S. PATENT DOCUMENTS

| 15,192 | A | 6/1856 | Peale |
| 274,447 | A | 3/1883 | Kennish |
| 733,152 | A | 7/1903 | Chisholm |
| 1,388,172 | A | 8/1921 | Craddock |
| 2,431,587 | A | 11/1947 | Schnee |
| 2,555,076 | A | 5/1951 | Crossley |
| 2,867,213 | A | 1/1959 | Thomas, Jr. |
| 3,159,161 | A | 12/1964 | Ness |
| 3,272,204 | A | 9/1966 | Artandi et al. |
| 3,310,051 | A | 3/1967 | Schulte |

(Continued)

FOREIGN PATENT DOCUMENTS

EP    0 102 747 A1    7/1983

(Continued)

OTHER PUBLICATIONS

Prata, João Antonio, Jr., MD, et al., "In Vitro and in Vivo Flow Characteristics of Glaucoma Drainage Implants," Ophthalmology, vol. 102, No. 6, pp. 894-904 (Jun. 1995).

(Continued)

*Primary Examiner* — Leslie Deak
(74) *Attorney, Agent, or Firm* — Kenyon & Kenyon LLP

(57) ABSTRACT

The disclosure provides an intraocular implant for allowing fluid flow from the anterior chamber of an eye, the implant comprising a tube having an inlet end, an outlet end, and a tube passage, wherein the inlet end is adapted to extend into the anterior chamber of the eye, and wherein the outlet end is adapted to be implanted adjacent scleral tissue of the eye. The implant may be adapted to drain aqueous humor into a suprachoroidal space or a juxta-uveal space. The disclosure also provides associated delivery devices, methods of use, and methods of manufacture.

12 Claims, 37 Drawing Sheets

U.S. PATENT DOCUMENTS

| | | | |
|---|---|---|---|
| 3,333,588 A | 8/1967 | Schulte | |
| 3,421,509 A | 1/1969 | Fiore | |
| 3,530,860 A | 9/1970 | Majoros | |
| 3,589,401 A | 6/1971 | Harding | |
| 3,788,327 A * | 1/1974 | Donowitz et al. | 604/247 |
| 3,884,238 A | 5/1975 | O'Malley et al. | |
| 3,890,976 A | 6/1975 | Bazell et al. | |
| 3,913,584 A | 10/1975 | Walchle et al. | |
| 3,915,172 A | 10/1975 | Wichterle et al. | |
| 3,938,529 A | 2/1976 | Gibbons | |
| 3,957,035 A | 5/1976 | Chassaing | |
| 3,976,077 A | 8/1976 | Kerfoot, Jr. | |
| 4,037,604 A | 7/1977 | Newkirk | |
| 4,142,526 A | 3/1979 | Zaffaroni et al. | |
| 4,153,058 A | 5/1979 | Nehme | |
| 4,175,563 A | 11/1979 | Arenberg et al. | |
| 4,290,426 A | 9/1981 | Luschen et al. | |
| 4,299,227 A | 11/1981 | Lincoff | |
| 4,303,063 A | 12/1981 | Stahl | |
| 4,402,681 A | 9/1983 | Haas et al. | |
| 4,457,757 A | 7/1984 | Molteno | |
| 4,474,569 A | 10/1984 | Newkirk | |
| 4,521,210 A | 6/1985 | Wong | |
| 4,526,343 A | 7/1985 | d'Agostino et al. | |
| 4,538,611 A | 9/1985 | Kelman | |
| 4,554,918 A | 11/1985 | White | |
| 4,563,779 A | 1/1986 | Kelman | |
| 4,578,058 A | 3/1986 | Grandon | |
| 4,587,954 A | 5/1986 | Haber | |
| 4,598,705 A | 7/1986 | Lichtenberger | |
| 4,604,087 A | 8/1986 | Joseph | |
| 4,634,418 A | 1/1987 | Binder | |
| 4,645,493 A | 2/1987 | Ferrando et al. | |
| 4,660,546 A | 4/1987 | Herrick et al. | |
| 4,692,142 A | 9/1987 | Dignam et al. | |
| 4,722,724 A | 2/1988 | Schocket | |
| 4,750,901 A | 6/1988 | Molteno | |
| 4,750,971 A | 6/1988 | Maas et al. | |
| 4,751,926 A | 6/1988 | Sasaki | |
| 4,781,675 A | 11/1988 | White | |
| 4,787,885 A | 11/1988 | Binder | |
| 4,808,183 A | 2/1989 | Panje | |
| 4,813,941 A | 3/1989 | Shea | |
| 4,826,478 A | 5/1989 | Schocket | |
| 4,863,457 A | 9/1989 | Lee | |
| 4,886,488 A | 12/1989 | White | |
| 4,909,783 A | 3/1990 | Morrison | |
| 4,915,684 A | 4/1990 | MacKeen et al. | |
| 4,934,363 A | 6/1990 | Smith et al. | |
| 4,936,825 A | 6/1990 | Ungerleider | |
| 4,942,875 A | 7/1990 | Hlavacek et al. | |
| 4,946,436 A | 8/1990 | Smith | |
| 4,959,048 A | 9/1990 | Seder et al. | |
| 4,964,850 A | 10/1990 | Bouton et al. | |
| 4,968,296 A * | 11/1990 | Ritch et al. | 604/8 |
| 5,000,731 A | 3/1991 | Wong et al. | |
| 5,041,081 A | 8/1991 | Odrich | |
| 5,053,040 A | 10/1991 | Goldsmith, III | |
| 5,064,417 A | 11/1991 | Andreussi | |
| 5,071,408 A | 12/1991 | Ahmed | |
| 5,073,163 A | 12/1991 | Lippman | |
| 5,092,837 A | 3/1992 | Ritch et al. | |
| 5,098,393 A | 3/1992 | Amplatz et al. | |
| 5,098,438 A | 3/1992 | Siepser | |
| 5,106,367 A | 4/1992 | Ureche et al. | |
| 5,109,867 A | 5/1992 | Twyford, Jr. | |
| 5,127,901 A | 7/1992 | Odrich | |
| 5,139,502 A | 8/1992 | Berg et al. | |
| 5,147,370 A | 9/1992 | McNamara et al. | |
| 5,167,620 A | 12/1992 | Ureche et al. | |
| 5,171,213 A | 12/1992 | Price, Jr. | |
| 5,171,270 A | 12/1992 | Herrick | |
| 5,178,604 A | 1/1993 | Baerveldt et al. | |
| 5,180,362 A * | 1/1993 | Worst | 604/8 |
| 5,190,552 A | 3/1993 | Kelman | |
| 5,207,660 A | 5/1993 | Lincoff | |
| 5,217,486 A | 6/1993 | Rice et al. | |
| 5,221,278 A | 6/1993 | Linkwitz et al. | |
| 5,242,449 A | 9/1993 | Zaleski | |
| 5,283,063 A | 2/1994 | Freeman | |
| 5,300,020 A | 4/1994 | L'Esperance, Jr. | |
| 5,318,558 A | 6/1994 | Linkwitz et al. | |
| 5,322,504 A | 6/1994 | Doherty et al. | |
| 5,326,345 A | 7/1994 | Price, Jr. | |
| 5,338,291 A | 8/1994 | Speckman et al. | |
| 5,342,370 A | 8/1994 | Simon et al. | |
| 5,346,464 A | 9/1994 | Camras | |
| 5,355,871 A | 10/1994 | Hurley et al. | |
| 5,358,492 A | 10/1994 | Feibus | |
| 5,360,398 A | 11/1994 | Grieshaber et al. | |
| 5,360,399 A | 11/1994 | Stegmann | |
| 5,370,607 A | 12/1994 | Memmen | |
| 5,372,577 A | 12/1994 | Ungerleider | |
| 5,380,290 A | 1/1995 | Makower et al. | |
| D356,867 S | 3/1995 | Krupin | |
| 5,397,300 A | 3/1995 | Baerveldt et al. | |
| 5,403,323 A | 4/1995 | Smith | |
| RE34,998 E | 7/1995 | Langerman | |
| 5,433,701 A | 7/1995 | Rubinstein | |
| 5,433,714 A | 7/1995 | Bloomberg | |
| 5,451,229 A | 9/1995 | Geuder et al. | |
| 5,454,796 A | 10/1995 | Krupin | |
| 5,476,445 A | 12/1995 | Baerveldt et al. | |
| 5,494,484 A | 2/1996 | Feingold | |
| 5,520,631 A | 5/1996 | Nordquist et al. | |
| 5,522,845 A | 6/1996 | Wenstrom, Jr. | |
| 5,558,629 A | 9/1996 | Baerveldt et al. | |
| 5,558,630 A | 9/1996 | Fisher | |
| 5,601,094 A | 2/1997 | Reiss | |
| 5,616,118 A | 4/1997 | Ahmed | |
| 5,626,558 A | 5/1997 | Suson | |
| 5,626,559 A * | 5/1997 | Solomon | 604/9 |
| 5,660,205 A | 8/1997 | Epstein | |
| 5,674,286 A | 10/1997 | D'Alessio et al. | |
| 5,681,275 A * | 10/1997 | Ahmed | 604/9 |
| 5,702,414 A | 12/1997 | Richter et al. | |
| 5,704,907 A | 1/1998 | Nordquist et al. | |
| 5,709,698 A | 1/1998 | Adams et al. | |
| 5,713,844 A | 2/1998 | Peyman | |
| 5,720,760 A | 2/1998 | Becker et al. | |
| 5,741,292 A | 4/1998 | Mendius | |
| 5,800,376 A | 9/1998 | Watson et al. | |
| 5,807,240 A | 9/1998 | Muller et al. | |
| 5,865,831 A | 2/1999 | Cozean et al. | |
| 5,868,697 A | 2/1999 | Richter et al. | |
| 5,879,319 A | 3/1999 | Pynson et al. | |
| 5,893,837 A | 4/1999 | Eagles et al. | |
| 5,968,058 A | 10/1999 | Richter et al. | |
| 6,004,302 A | 12/1999 | Brierley | |
| 6,007,510 A | 12/1999 | Nigam | |
| 6,007,511 A | 12/1999 | Prywes | |
| 6,050,970 A | 4/2000 | Baerveldt | |
| 6,102,045 A | 8/2000 | Nordquist et al. | |
| 6,168,575 B1 | 1/2001 | Soltanpour | |
| 6,186,974 B1 | 2/2001 | Allan et al. | |
| RE37,117 E | 3/2001 | Palermo | |
| 6,203,513 B1 | 3/2001 | Yaron et al. | |
| 6,221,078 B1 | 4/2001 | Bylsma | |
| 6,245,077 B1 | 6/2001 | East et al. | |
| 6,264,625 B1 | 7/2001 | Rubenstein et al. | |
| 6,280,468 B1 | 8/2001 | Schachar | |
| 6,299,640 B1 | 10/2001 | Schachar | |
| 6,450,984 B1 | 9/2002 | Lynch et al. | |
| 6,464,724 B1 | 10/2002 | Lynch et al. | |
| 6,471,666 B1 | 10/2002 | Odrich | |
| 6,524,275 B1 | 2/2003 | Lynch et al. | |
| 6,533,768 B1 | 3/2003 | Hill | |
| 6,544,249 B1 | 4/2003 | Yu et al. | |
| 6,558,342 B1 | 5/2003 | Yaron et al. | |
| 6,626,858 B2 | 9/2003 | Lynch et al. | |
| 6,638,239 B1 | 10/2003 | Bergheim et al. | |
| 6,666,841 B2 | 12/2003 | Gharib et al. | |
| 6,682,523 B2 | 1/2004 | Shadduck | |
| D490,152 S | 5/2004 | Myall et al. | |
| 6,730,056 B1 | 5/2004 | Ghaem et al. | |
| 6,736,791 B1 | 5/2004 | Tu et al. | |
| 6,780,164 B2 | 8/2004 | Bergheim et al. | |

| | | |
|---|---|---|
| 6,783,544 B2 | 8/2004 | Lynch et al. |
| 6,827,699 B2 | 12/2004 | Lynch et al. |
| 6,827,700 B2 | 12/2004 | Lynch et al. |
| 6,939,298 B2 | 9/2005 | Brown et al. |
| 6,955,656 B2 | 10/2005 | Bergheim et al. |
| 6,981,958 B1 | 1/2006 | Gharib et al. |
| 6,989,007 B2 | 1/2006 | Shadduck |
| 7,008,396 B1 | 3/2006 | Straub |
| 7,041,077 B2 | 5/2006 | Shields |
| 7,094,225 B2 | 8/2006 | Tu et al. |
| 7,135,009 B2 | 11/2006 | Tu et al. |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,965 B2 | 4/2007 | Simon |
| 7,220,238 B2 | 5/2007 | Lynch et al. |
| 7,273,475 B2 | 9/2007 | Tu et al. |
| 7,291,125 B2 | 11/2007 | Coroneo |
| 7,297,130 B2 | 11/2007 | Bergheim et al. |
| 7,331,984 B2 | 2/2008 | Tu et al. |
| 7,431,710 B2 | 10/2008 | Tu et al. |
| 7,488,303 B1 | 2/2009 | Haffner et al. |
| 7,563,241 B2 | 7/2009 | Tu et al. |
| 2002/0133168 A1 | 9/2002 | Smedley et al. |
| 2002/0143284 A1 | 10/2002 | Tu et al. |
| 2003/0060752 A1 | 3/2003 | Bergheim et al. |
| 2003/0097151 A1 | 5/2003 | Smedley et al. |
| 2003/0229303 A1 | 12/2003 | Haffner et al. |
| 2003/0236484 A1 | 12/2003 | Lynch et al. |
| 2004/0015140 A1 | 1/2004 | Shields |
| 2004/0024345 A1 | 2/2004 | Gharib et al. |
| 2004/0102729 A1 | 5/2004 | Haffner et al. |
| 2004/0111050 A1 | 6/2004 | Smedley et al. |
| 2004/0127843 A1 | 7/2004 | Tu et al. |
| 2004/0147870 A1 | 7/2004 | Burns et al. |
| 2004/0154946 A1 | 8/2004 | Solovay et al. |
| 2004/0210185 A1 | 10/2004 | Tu et al. |
| 2004/0216749 A1 | 11/2004 | Tu |
| 2004/0225250 A1 | 11/2004 | Yablonski |
| 2004/0254520 A1 | 12/2004 | Porteous et al. |
| 2004/0260228 A1 | 12/2004 | Lynch et al. |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0119601 A9 | 6/2005 | Lynch et al. |
| 2005/0119636 A1 | 6/2005 | Haffner et al. |
| 2005/0165385 A1 | 7/2005 | Simon |
| 2005/0209550 A1 | 9/2005 | Bergheim et al. |
| 2005/0250788 A1 | 11/2005 | Tu et al. |
| 2005/0266047 A1 | 12/2005 | Tu et al. |
| 2005/0271704 A1 | 12/2005 | Tu et al. |
| 2005/0277864 A1 | 12/2005 | Haffner et al. |
| 2006/0032507 A1 | 2/2006 | Tu |
| 2006/0069340 A1 | 3/2006 | Simon |
| 2006/0173397 A1 | 8/2006 | Tu et al. |
| 2006/0200113 A1 | 9/2006 | Haffner et al. |
| 2006/0241749 A1 | 10/2006 | Tu et al. |
| 2007/0010827 A1 | 1/2007 | Tu et al. |
| 2007/0088242 A1 | 4/2007 | Coroneo |
| 2007/0106235 A1 | 5/2007 | Coroneo |
| 2007/0106236 A1 | 5/2007 | Coroneo |
| 2007/0149915 A1 | 6/2007 | Yablonski |
| 2007/0191863 A1 | 8/2007 | De Juan et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2008/0015488 A1 | 1/2008 | Tu et al. |
| 2008/0045878 A1 | 2/2008 | Bergheim et al. |
| 2008/0183121 A2 | 7/2008 | Smedley et al. |
| 2008/0195027 A1 | 8/2008 | Coroneo |
| 2008/0200860 A1 | 8/2008 | Tu et al. |
| 2008/0228127 A1 | 9/2008 | Burns et al. |
| 2008/0234624 A2 | 9/2008 | Bergheim et al. |
| 2009/0036819 A1 | 2/2009 | Tu et al. |
| 2009/0076436 A2 | 3/2009 | Gharib et al. |
| 2009/0137983 A1 | 5/2009 | Bergheim et al. |
| 2009/0138022 A1 | 5/2009 | Tu et al. |
| 2009/0138081 A1 | 5/2009 | Bergheim et al. |
| 2009/0143712 A1 | 6/2009 | Tu et al. |
| 2009/0182421 A1 | 7/2009 | Silvestrini et al. |

FOREIGN PATENT DOCUMENTS

| | | |
|---|---|---|
| EP | 0 228 185 A1 | 7/1987 |
| EP | 0 606 188 A1 | 7/1994 |
| EP | 1 310 222 A2 | 5/2003 |
| FR | 2 721 499 A1 | 12/1995 |
| FR | 2 757 068 A1 | 6/1998 |
| JP | 63-305860 | 12/1988 |
| JP | 3-292953 | 12/1991 |
| JP | 5-115502 | 5/1993 |
| JP | 5-502811 | 5/1993 |
| JP | 8-155540 | 6/1996 |
| JP | 2003-102765 A | 4/2003 |
| SU | 1191227 A | 11/1985 |
| SU | 1797884 A1 | 2/1993 |
| WO | 91/08784 A1 | 6/1991 |
| WO | 92/00112 A1 | 1/1992 |
| WO | 93/20783 A1 | 10/1993 |
| WO | 94/02081 A1 | 2/1994 |
| WO | 94/06503 A1 | 3/1994 |
| WO | 94/09837 A1 | 5/1994 |
| WO | 94/13234 A1 | 6/1994 |
| WO | 94/17755 A1 | 8/1994 |
| WO | 94/21443 A1 | 9/1994 |
| WO | 95/35078 A1 | 12/1995 |
| WO | 96/03944 A1 | 2/1996 |
| WO | 96/20742 A1 | 7/1996 |
| WO | 96/36377 A1 | 11/1996 |
| WO | 98/30181 A1 | 7/1998 |
| WO | 99/26567 A1 | 6/1999 |
| WO | 00/64393 A1 | 11/2000 |
| WO | 00/72788 A1 | 12/2000 |
| WO | 2007/087061 A2 | 8/2007 |
| WO | 2008/005873 A2 | 1/2008 |
| WO | 2008/061043 A2 | 5/2008 |
| WO | 2009/012406 A1 | 1/2009 |

OTHER PUBLICATIONS

Krupin, Theodore, et al., "Drainage Implants," Glaucoma, edited by Paul L. Kaufman, MD, et al., Section VII, pp. 9.62-9.75 (1994).
Sidoti, Paul A., MD, et al., "Glaucoma Drainage Implants," Current Opinion in Ophthalmology, vol. 5, No. 11 (1994), 4 pages.
Middleton, John C., et al., "Synthetic Biodegradable Polymers as Medical Devices," Medical Plastics and Biomaterials Magazine—MPB Article Index, Mar. 1998, 14 pages [printed May 18, 1999].
International Search Report and Written Opinion of the International Searching Authority, mailed Jun. 20, 2011, from related International Application No. PCT/US2011/029796.

* cited by examiner

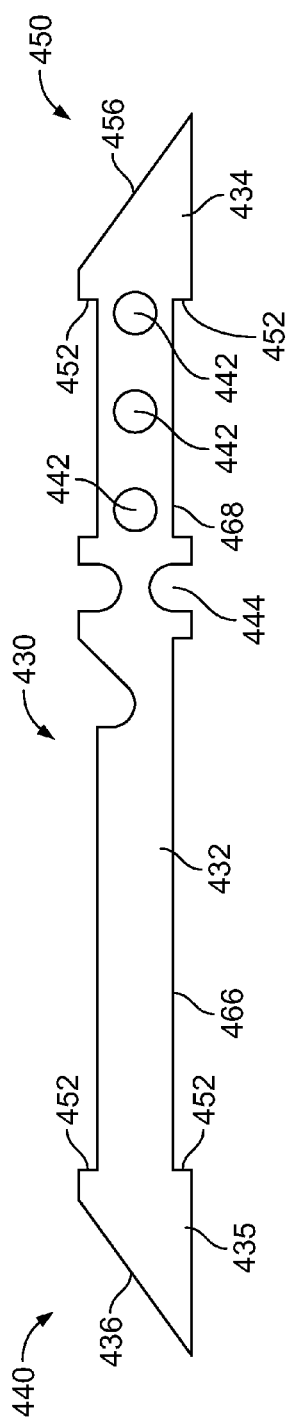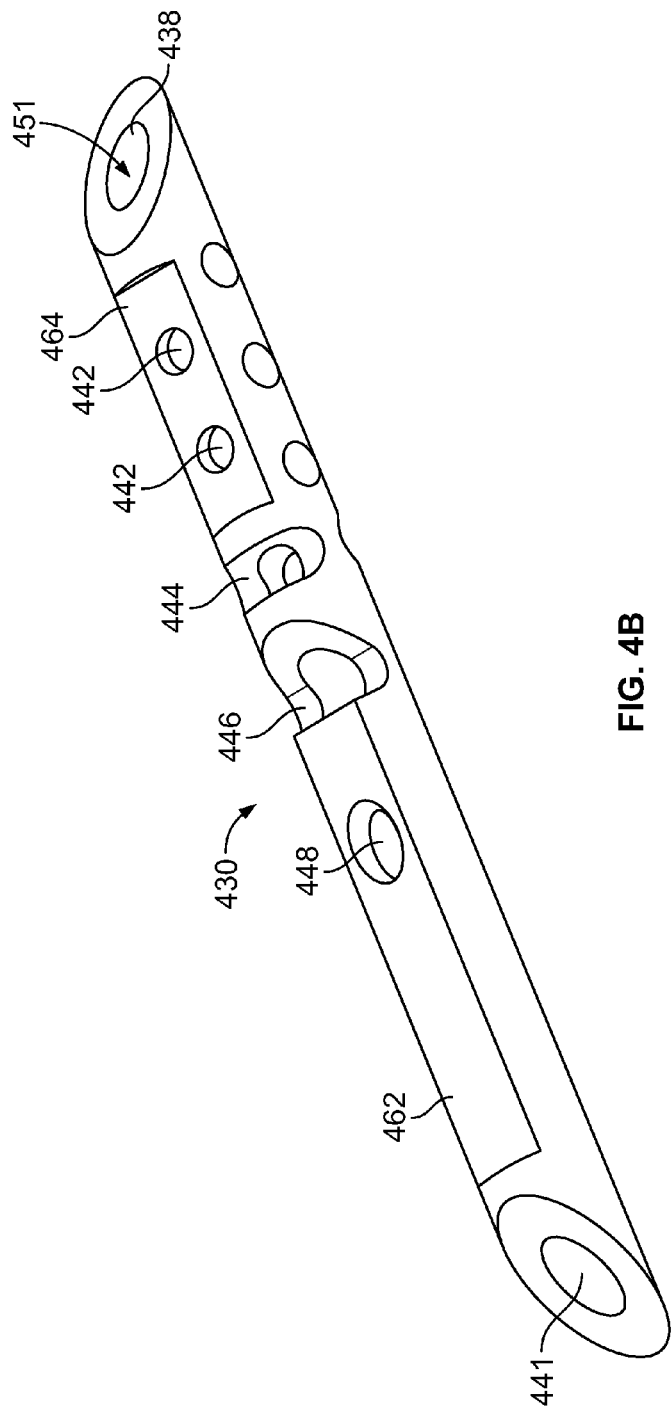

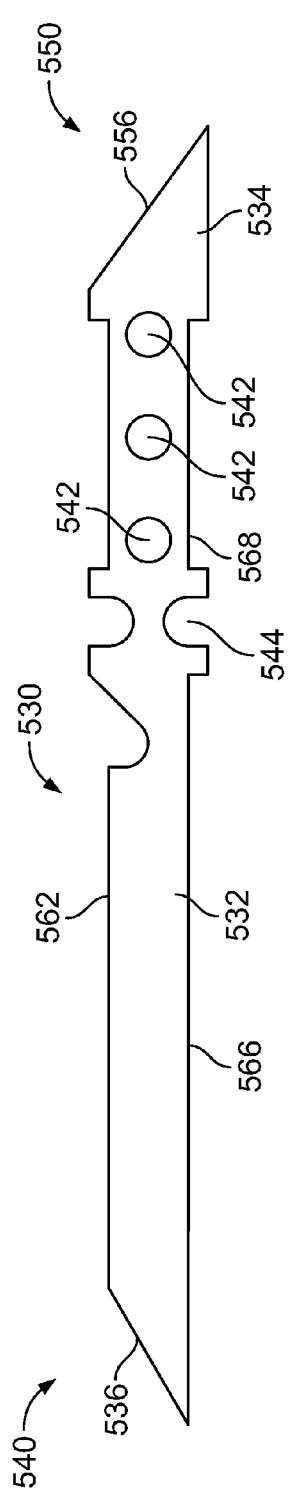
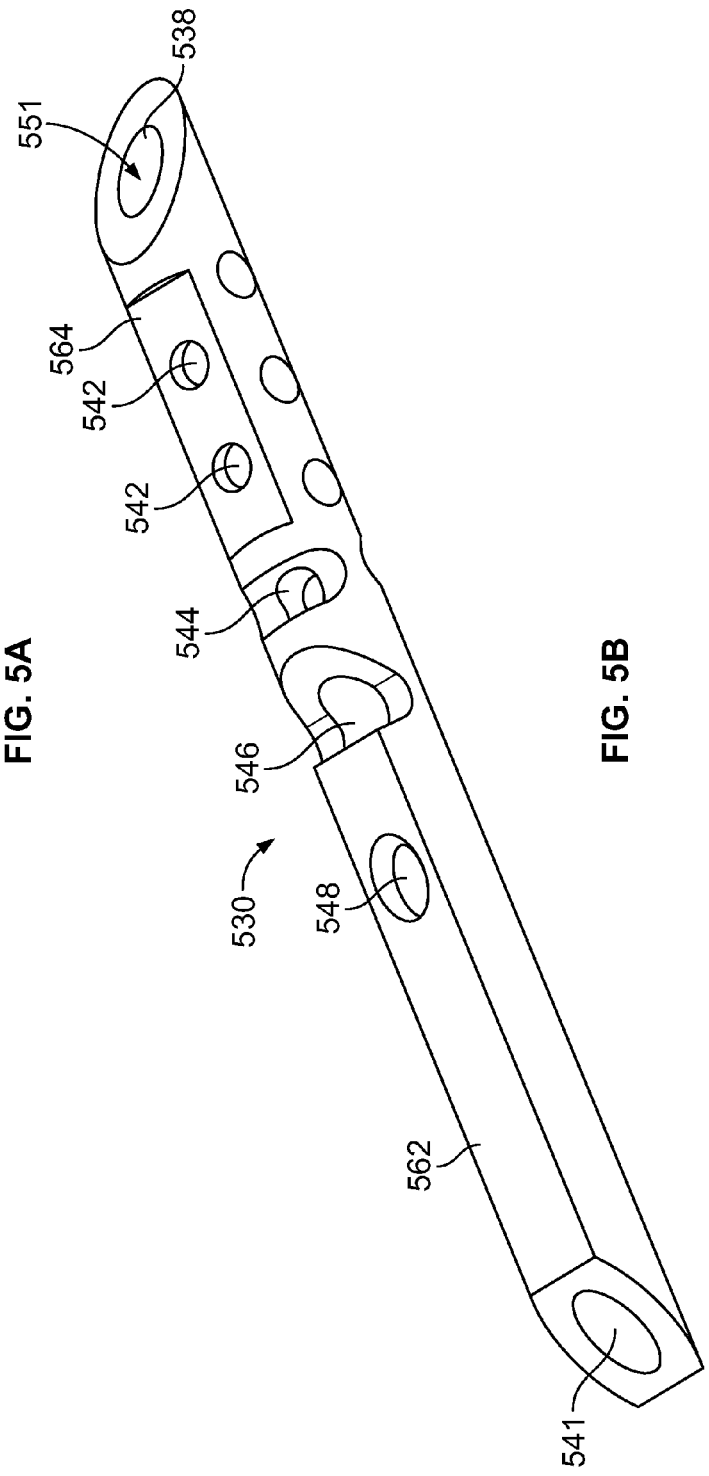
FIG. 5A
FIG. 5B

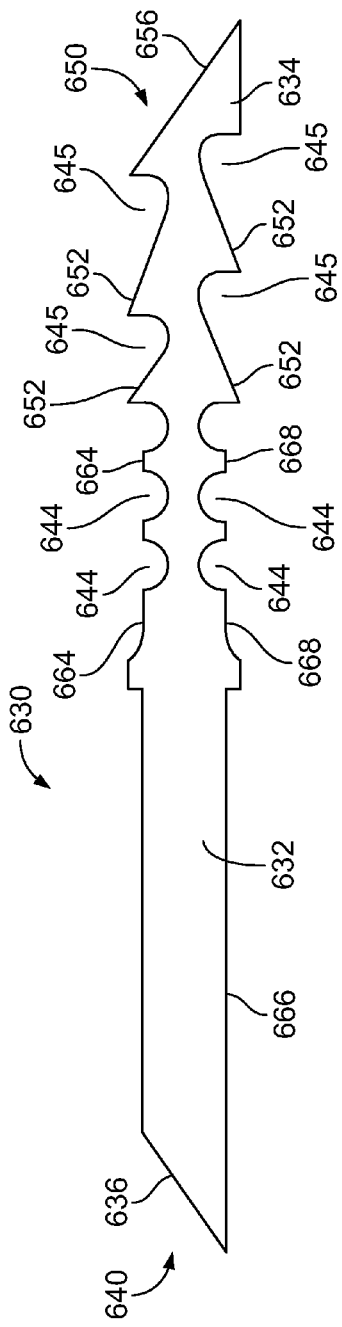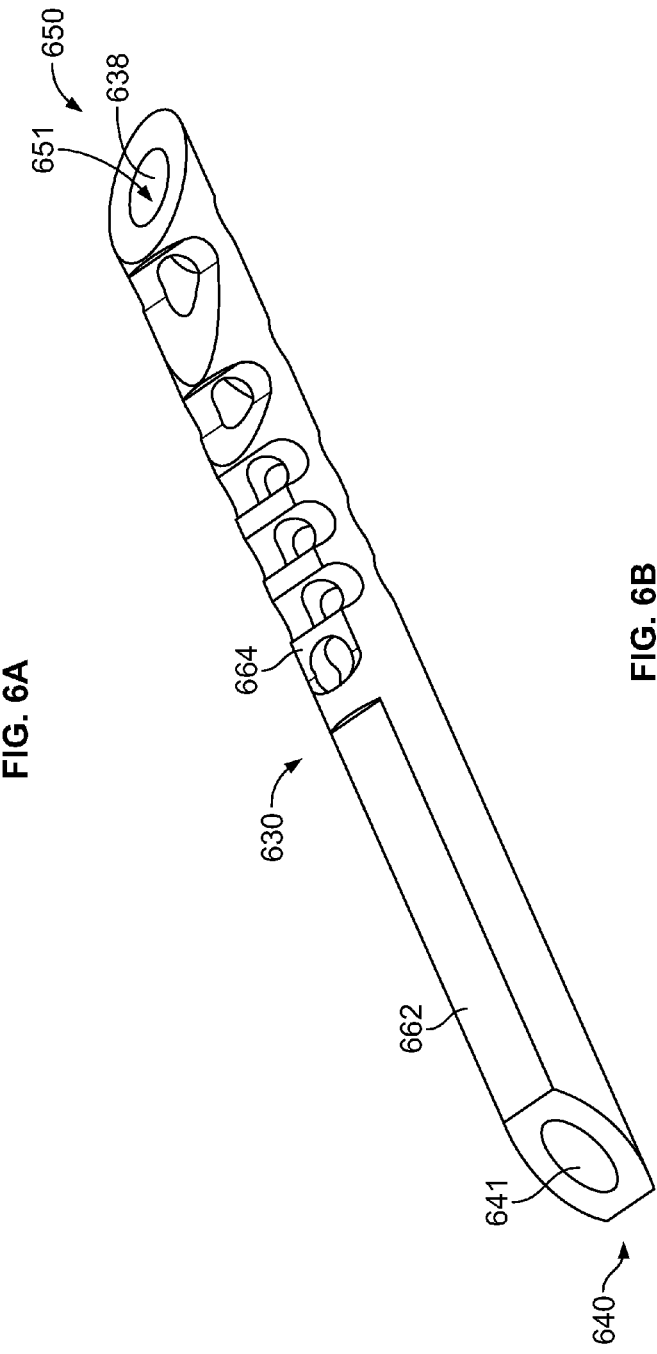

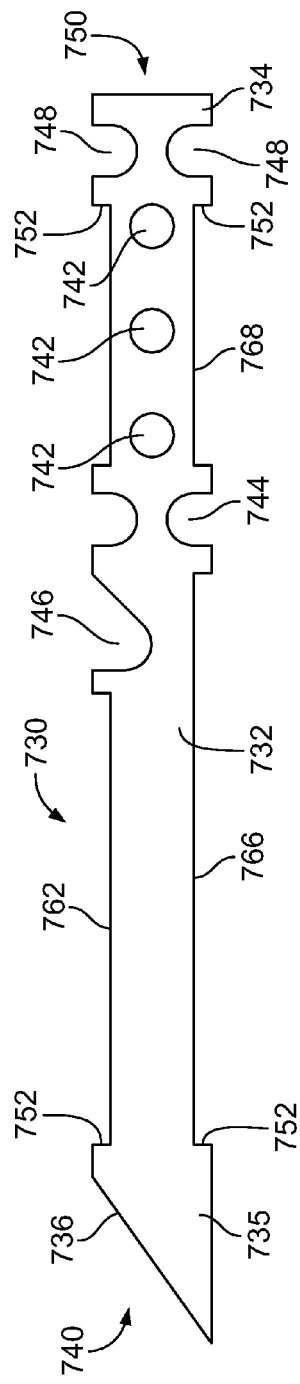
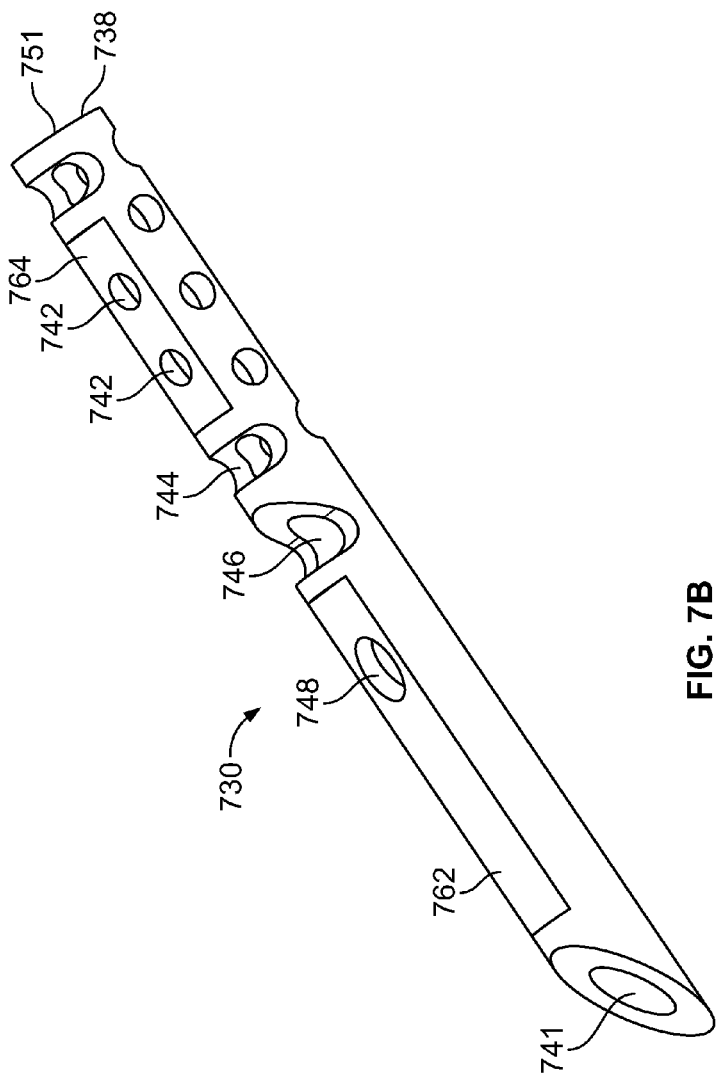
FIG. 7A
FIG. 7B

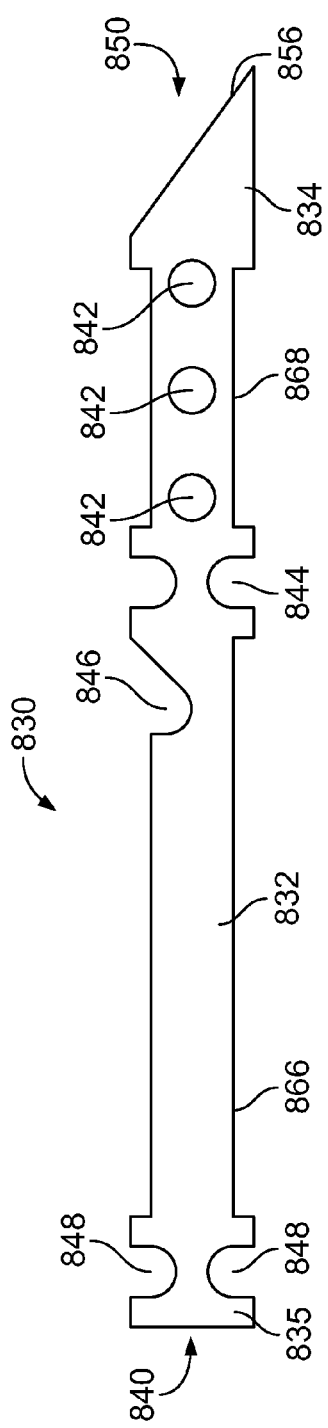
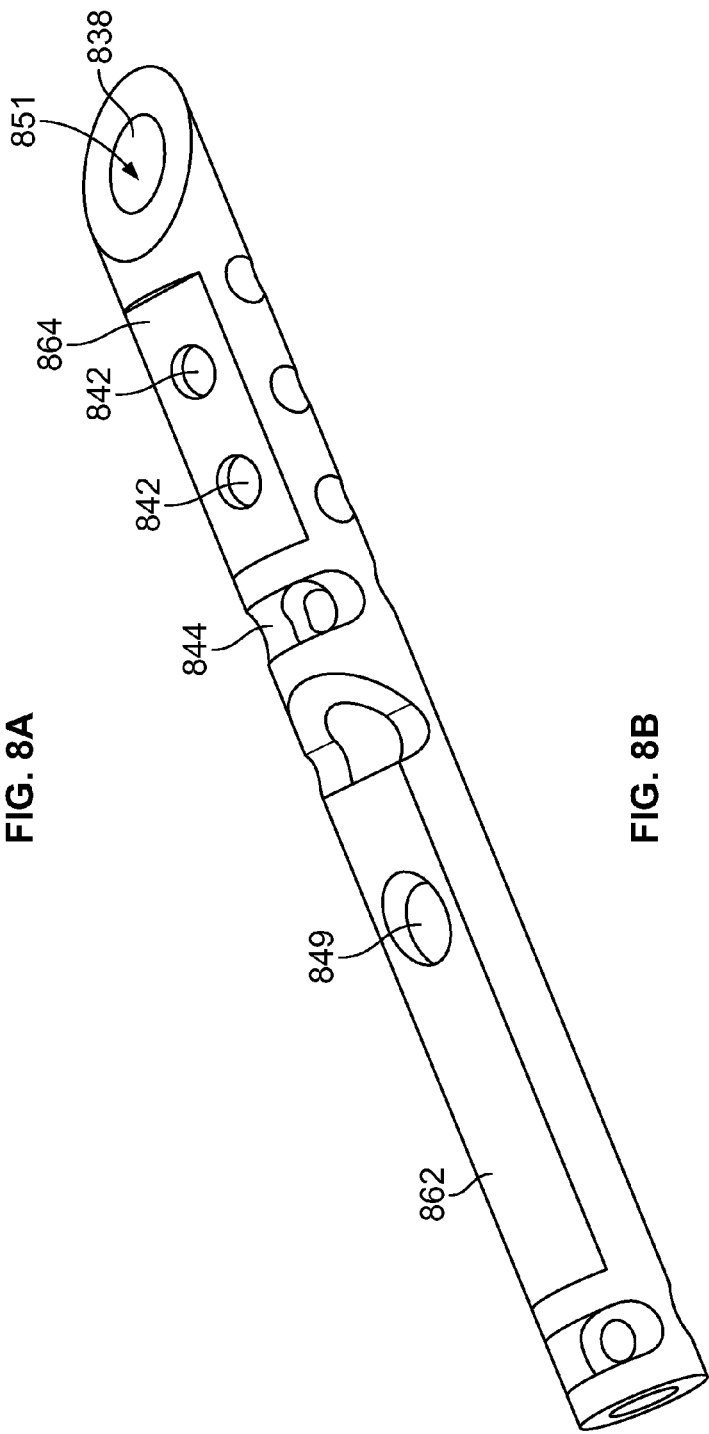
FIG. 8A
FIG. 8B

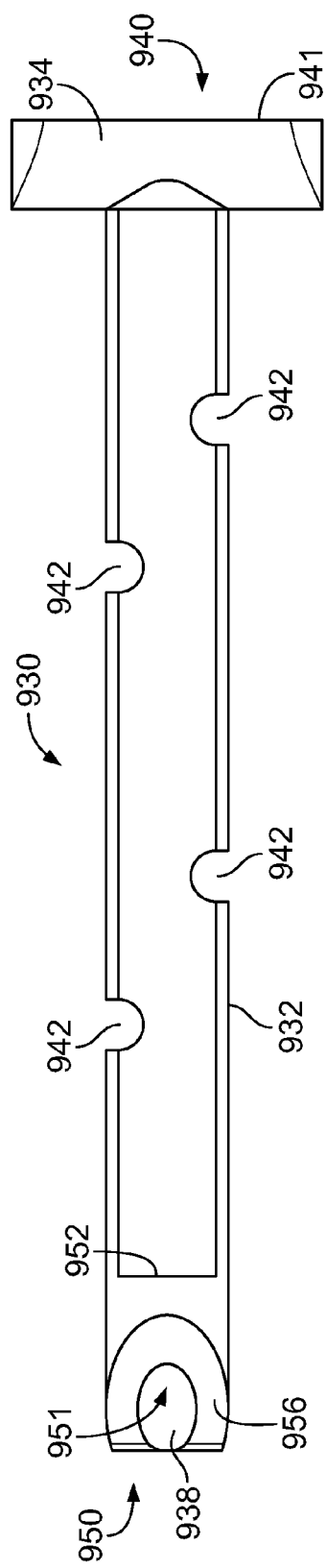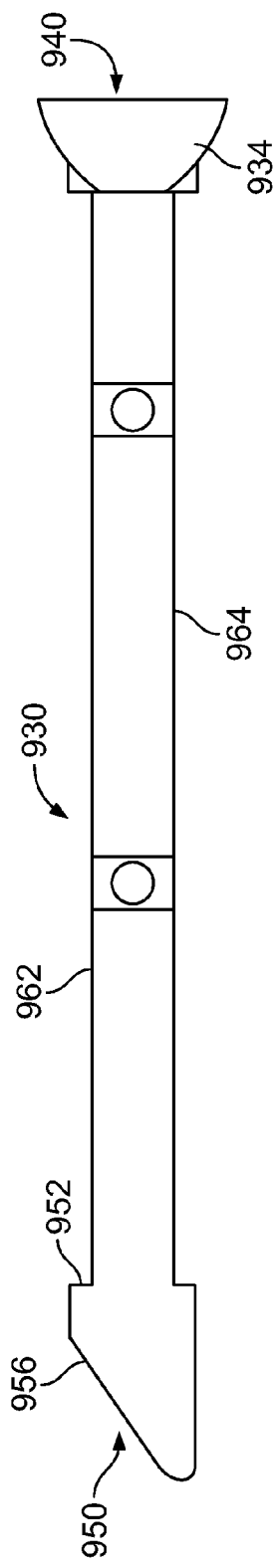
FIG. 9A
FIG. 9B

FLUID DRAINAGE DEVICE, DELIVERY DEVICE, AND ASSOCIATED METHODS OF USE AND MANUFACTURE

RELATED U.S. APPLICATIONS

This application is a continuation-in-part of U.S. patent application Ser. No. 12/691,176, filed Jan. 21, 2010, which is a continuation of U.S. patent application Ser. No. 11/952,819, filed Dec. 7, 2007, now U.S. Pat. No. 7,670,310, which is a continuation of U.S. patent application Ser. No. 10/314,324, filed Dec. 9, 2002, now abandoned, which is a divisional of U.S. patent application Ser. No. 09/729,050, filed Dec. 4, 2000, now U.S. Pat. No. 6,510,600, which is a divisional of U.S. patent application Ser. No. 08/975,386, filed Nov. 20, 1997, now U.S. Pat. No. 6,203,513, the disclosures of which are hereby expressly incorporated herein by reference.

FIELD OF THE INVENTION

The invention relates to fluid drainage devices, such as for drainage of aqueous humor from the eye to treat glaucoma, and to delivery devices for implanting fluid drainage devices. The invention also relates to associated methods of use and manufacture.

BACKGROUND OF THE INVENTION

Glaucoma is an eye condition typically characterized by an increase in the intraocular pressure (IOP) of the eye to an abnormal level. A normal eye maintains a proper IOP by the circulation within the eye of aqueous humor. Aqueous humor is secreted from the ciliary body, passes through the pupil into the anterior chamber of the eyeball, and is filtered out of the eyeball via the trabeculum and the Canal of Schlemm (or Schlemm's Canal). With glaucoma, the aqueous humor excretory pathway is blocked, the aqueous humor cannot pass out of the eyeball at an adequate rate, the IOP rises, the eyeball becomes harder, and the optic nerve atrophies due to the pressure applied on its fibers leaving the retina. A characteristic optic neuropathy develops, resulting in progressive death of the ganglion cells in the retina, restriction of the visual field, and eventual blindness. Advanced stages of the disease are characterized also by significant pain.

Glaucoma treatment, if initiated early in the course of the disease, can prevent further deterioration and preserve most of the ocular functions. The goal of glaucoma treatment is to reduce the IOP to a level which is considered safe for a particular eye, but which is not so low as to cause ocular malfunction or retinal complications.

In the past, procedures and devices have been developed and implemented for providing an alternate route for aqueous humor to pass out of the eye. For example, in full thickness filtration surgery, a fistula is created through the limbal sclera, connecting directly the anterior chamber of the eyeball and the sub-conjunctival space. This provides an alternate route, allowing the aqueous humor to exit the anterior chamber of the eyeball through the fistula in the limbal sclera and to pass into the sub-conjunctival space. During healing, however, there is potential for cell growth and scar formation in the sclera and/or conjunctiva, potentially obstructing the fluid passage.

In guarded filtration surgery (trabeculectomy), a fistula created through the limbal sclera is protected by an overlying partial thickness sutured scleral flap. This procedure similarly provides an alternate route, allowing the aqueous humor to exit the anterior chamber of the eyeball, through the fistula in the limbal sclera, allowing the aqueous humor to pass under the scleral flap and into the sub-conjunctival space. Again there is a possibility of obstructing the fluid passage, due to the potential for cell growth and scar formation in the sclera and/or conjunctiva.

In a deep sclerectomy, a superficial flap is made in the sclera and then a second deep scleral flap is created and excised leaving a scleral reservoir or well under the first flap. A thin permeable membrane is exposed between the anterior chamber and the scleral reservoir. The procedure is non-penetrating in that no penetration is made into the anterior chamber. The aqueous humor percolates from the anterior chamber through the thin membrane into the scleral reservoir and into the Schlemm's Canal. This procedure can be difficult to perform and has not been shown to be fully effective in reducing IOP.

Trabeculoplasty procedures are procedures wherein a physician uses a laser to create holes in the trabecular meshwork in order to allow flow from the anterior chamber into the Schlemm's Canal. The two primary types of trabeculoplasty are argon laser trabeculoplasty (ALT) and selective laser trabeculoplasty (SLT). Trabeculoplasty may not be a suitable long-term treatment as the meshwork may close again, for example due to scarring.

The TRABECTOME® device of NeoMedix, Inc., has been proposed for another method for providing passage through the trabecular meshwork. The device is passed through a corneal incision and across the anterior chamber. The device's tip has a bipolar micro-electrocautery electrode that ablates and removes a strip of trabecular meshwork. As with trabeculoplasty, this procedure may not be a suitable long-term treatment as the meshwork may close again.

In addition to various procedures, drainage implant devices have also been developed and implemented. For example, some implants have a tube that is inserted through the limbal sclera. The tube provides an alternate route for the aqueous humor to leave the eye.

Many of these known devices and methods do not provide adequate regulation of IOP or have other potential drawbacks. For example, with some devices and methods, the initial procedure can cause excessive loss of aqueous humor from the eyeball during the early postoperative period, frequently leading to hypotony. With other devices and methods, there may be too much resistance to the flow of aqueous humor from the eyeball, thereby resulting in higher eventual IOP and an increased risk of late failure. There is also the risk that the drainage pathway will become clogged, for example due to iris prolapse or due to scarring, or that infection could occur because of the passageway into the eye. In certain valved implant devices, defects in and/or failure of the valve mechanisms can lead to either too much or too little aqueous humor exiting the eye. In procedures that drain into a "bleb" in the sub-conjunctival space, there is sometimes a risk of leakage or infection. Additionally, some implant insertion operations can be complicated, lengthy, and costly.

There continues to be a desire for improvements in treating glaucoma, to provide improved patient outcomes in an efficient manner.

SUMMARY OF THE INVENTION

In certain embodiments, the disclosure provides an intraocular implant for allowing fluid flow from the anterior chamber of an eye, the implant comprising a tube having an inlet end, an outlet end, and a tube passage, wherein the inlet end is adapted to extend into the anterior chamber of the eye, and wherein the outlet end is adapted to be implanted adjacent scleral tissue of the eye. The implant may be adapted to drain aqueous humor into a suprachoroidal space. The implant may be adapted to drain aqueous humor into a juxta-uveal space. The tube of the implant may penetrate through or near the trabecular meshwork or through the anterior chamber angle of the eye.

In certain embodiments, the intraocular implant may comprise one or more side holes. The side holes may be formed by lateral cuts, grooves or channels in the tube. The side holes may be staggered in relation to each other.

In certain embodiments, the intraocular implant may comprise a beveled surface at the inlet end, the outlet end, or both. The intraocular implant may further comprise one or more retention projections in the form of one or more spurs and/or one or more spikes. The intraocular implant may further comprise one or more flat surfaces along the length of the tube, giving the tube a reduced profile.

In certain embodiments, the intraocular implant may comprise a flange at the inlet end, the outlet end, or both. The flange may comprise one or more grooves or access pockets for receiving the wall of a delivery device. The flange may have one or more spacers. If a flange is at the inlet end, the side of the flange that faces the tube may be rounded, tapered or conical.

In certain embodiments, the tube may have one or more narrow areas, reduced profiles, or holes for suturing the implant in position. The tube may have a curvature along its length. The implant may be curved at the inlet end. The implant may comprise a curved support portion attached to the tube.

In certain embodiments, the disclosure provides a delivery device comprising a rodlike instrument. The delivery device may comprise a tip for penetrating a tube passage of the implant. The delivery device may comprise a retention mechanism for preventing the implant from moving up the delivery device during implantation. The retention mechanism may be an abutment surface. The delivery device may comprise a bore for accommodating the implant. The delivery device may comprise a recess for accommodating the tube of the implant and a tip for inserting into a hole in the implant.

In certain embodiments, the disclosure provides a method of implanting an intraocular implant, comprising loading the implant in or on a delivery device, forming an incision in the eye, directing the implant to a desired implantation location, and withdrawing the delivery device. The implantation may be performed ab externo or ab interno. The outlet end of the implant may be implanted in a juxta-uveal location.

In certain embodiments, the disclosure provides a method of manufacturing an intraocular implant comprising providing a tube and cutting the tube.

BRIEF DESCRIPTION OF THE DRAWINGS

FIG. 4A is a side view of an implant in accordance with another embodiment;
FIG. 4B is a perspective view of the implant of FIG. 4A;
FIG. 5A is a side view of an implant in accordance with another embodiment;
FIG. 5B is a perspective view of the implant of FIG. 5A;
FIG. 6A is a side view of an implant in accordance with another embodiment;
FIG. 6B is a perspective view of the implant of FIG. 6A;
FIG. 7A is a side view of an implant in accordance with another embodiment;
FIG. 7B is a perspective view of the implant of FIG. 7A;
FIG. 8A is a side view of an implant in accordance with another embodiment;
FIG. 8B is a perspective view of the implant of FIG. 8A;
FIG. 9A is a side view of an implant in accordance with another embodiment;
FIG. 9B is another side view of the implant of FIG. 9A.

DETAILED DESCRIPTION

Figure 1A:
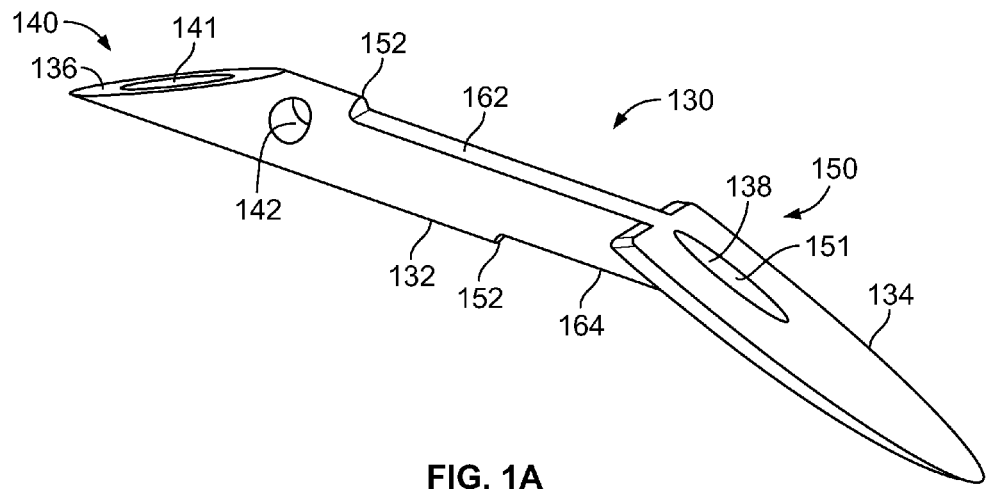
FIG. 1A is a perspective view of an implant in accordance with a first embodiment.

FIG. 1A shows a perspective view of an implant 130 in accordance with a first embodiment. The implant 130 in FIG. 1A is similar to implants described and illustrated in U.S. patent application Ser. No. 08/975,386, filed Nov. 20, 1997, now U.S. Pat. No. 6,203,513, the disclosure of which, as mentioned above, is incorporated by reference herein.

As can be seen in FIG. 1A, the implant 130 comprises a needle-like tube 132 and a disk or flange 134. The plane of the flange 134 forms an angle with the tube 132. The tube 132 has an inlet end 140, an outlet end 150, and a tube passage 138 extending between inlet end 140 and the outlet end 150, with the tube passage 138 having an axial inlet 141 and an axial outlet 151. The flange 134 is connected to the tube 132 at its outlet end 150.

The entire implant may be very small, and the size will depend on the intended application and implantation site. As one example, the tube 132 may have a length of about 2 mm to about 3 mm and a width or outer diameter of about 0.5 mm, and the flange 134 may have a width or diameter of about 1 mm and a thickness of less than 0.1 mm. As another example, the tube 132 may have a length of about 3 mm to about 6 mm and a width or outer diameter of about 0.3 mm to about 0.6 mm, for example about 0.4 mm or 0.5 mm, and the flange 134 may have a width or diameter of about 0.3 mm to about 1 mm. Many variations are possible, depending on the intended application and implantation site.

The tube passage 138 is sized to provide the desired flow characteristics. In general terms, a wide and short tube passage 138 will permit more flow than a narrow and long tube passage 138. The tube passage 138 may have a cross-sectional area sufficiently small to restrict or inhibit the flow of aqueous humor through the tube passage 138. In one embodiment, for example, the cylindrical tube passage 138 has a width or diameter of about 100 micrometers to about 300 micrometers, for example about 200 micrometers. By using a specified internal cross-sectional area for the tube passage 138, excessive loss of aqueous humor from the eye is prevented.

An implant having the general design such as shown in FIG. 1A or in U.S. patent application Ser. No. 08/975,386 may be implanted in multiple different locations. For example, FIG. 1 of U.S. patent application Ser. No. 08/975,386 illustrates an intraocular implant 30 inserted in the sclera 12 of the eyeball 10, in the limbal area 14 adjacent to the cornea 16. The tip of the implant 30 protrudes into the anterior chamber 20 adjacent the iris 22. The implant 30 is inserted so that the flange 34 is placed on a surface of the sclera 12 underneath the conjunctiva 18. When the implant 30 is implanted in the location illustrated in FIG. 1 of U.S. patent application Ser. No. 08/975,386, aqueous humor drains from the anterior chamber 20 of the eyeball 10 through the axial inlet 41 and one or more side holes 42, through the tube passage 38, and into the space under the conjunctiva 18. The side holes 42 help prevent the tube passage 38 from becoming clogged at its inlet end because, even if the iris 22 obstructs the axial inlet 41, aqueous humor can still pass through the side holes 42. In the event the axial inlet 41 is obstructed, the side holes 42 also serve to cause a back pressure in the tube passage 38 to unclog the axial inlet 41. The side holes 42 serve the additional purpose of insuring a proper insertion depth of the implant 30, as the upper hole is visible during implantation after penetration through the sclera and thus can be used as a marker. To serve this function, any other suitable marker (such as a scratch or colored mark) may be used. The implant 30 illustrated in FIG. 1 of U.S. patent application Ser. No. 08/975,386 also has a beveled surface 36 at the inlet end 40. The beveled surface 36 increases the area of the axial inlet 41 to enlarge the entrance to the tube passage 38. As illustrated in FIG. 1 of U.S. patent application Ser. No. 08/975,386, the beveled surface 36 faces away from the iris 22 to reduce the possibility of obstruction of the axial inlet 41. The implant 30 also has one or more retention projections in the form of one or more spurs 52 for retaining the implant 30 in the eye 10 after insertion.

Figure 1B:
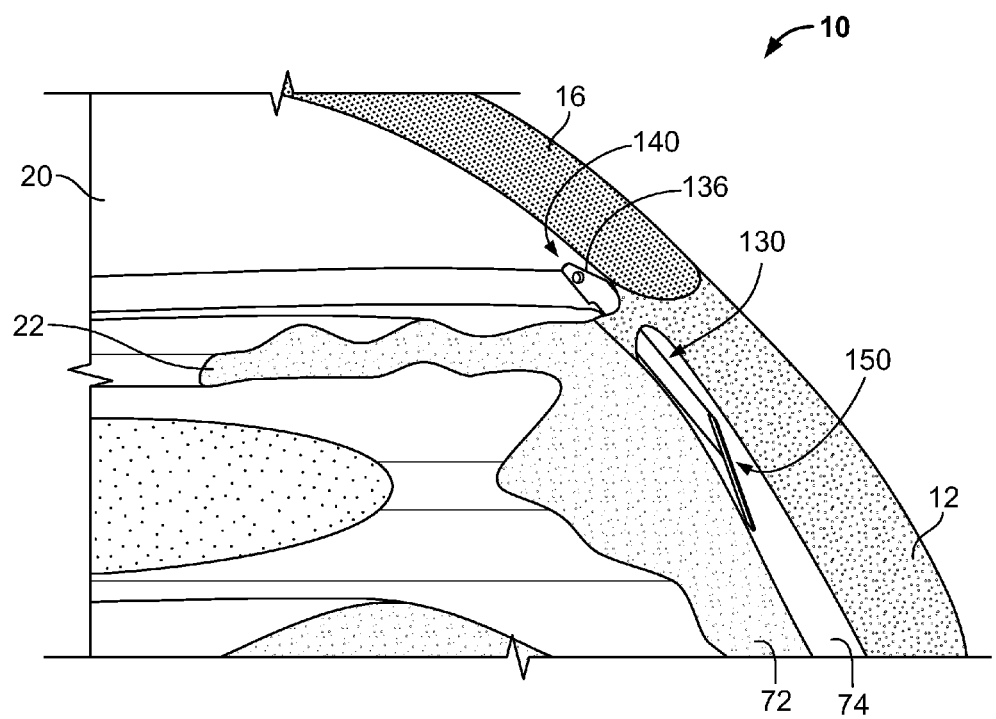
FIG. 1B shows the implant of FIG. 1A implanted in an eye.

An implant having the general design such as shown in FIG. 1A or in U.S. patent application Ser. No. 08/975,386 may alternatively be implanted to direct the flow of aqueous humor into a suprachoroidal space, for example as shown in FIG. 1B. FIG. 1B shows the implant 130 positioned with its inlet end 140 in the anterior chamber 20 adjacent the iris 22 and its outlet end 150 positioned to direct the flow of aqueous humor into or toward a suprachoroidal space 74 between the choroid 72 and the sclera 12. The implant 130 is placed in the area of the anterior chamber angle of the eye, with the tube of the implant 130 penetrating through the trabecular meshwork or other tissue by which the tube passage of the implant 130 provides a fluid passageway from the anterior chamber to the suprachoroidal space.

When the implant 130 is implanted in the location illustrated in FIG. 1B, aqueous humor drains from the anterior chamber 20 of the eyeball 10 through the axial inlet 141 and one or more side holes 142, through the tube passage 138, and into the suprachoroidal space 74. The side holes 142 help prevent the tube passage 138 from becoming clogged at its inlet end because, even if the iris 22 obstructs the axial inlet 141, aqueous humor can still pass through the side holes 142. In the event the axial inlet 141 is obstructed, the side holes 142 also serve to cause a back pressure in the tube passage 138 to unclog the axial inlet 141. The side holes 142 serve the additional purpose of insuring a proper insertion depth of the implant 130, as the holes are visible during implantation and thus can be used as a marker. As mentioned above, to serve this function, any other suitable marker (such as a scratch or colored mark) may be used.

The implant 130 illustrated in FIG. 1A has a beveled surface 136 at the inlet end 140. The beveled surface 136 increases the area of the axial inlet 141 to enlarge the entrance to the tube passage 138. As illustrated in FIG. 1B, the implant 130 can be implanted such that the beveled surface 136 faces away from the iris 22, toward the cornea 16, to reduce the possibility of obstruction of the axial inlet 141 by the iris 22. The implant 130 also has one or more retention projections in the form of one or more spurs 152 for retaining the implant 130 in the eye 10 after insertion.

As can be seen in FIG. 1A, the implant 130 has been made with a reduced profile along most of its length. This can be done, for example, so that the implant takes up less space, can fit more easily into the desired location, and/or is less prone to rotation. The implant may be manufactured, e.g., molded, with a reduced profile tube. Alternatively, the implant may initially be manufactured from a cylindrical tube and then material can be removed from sides of the tube to give the implant the desired profile. For example, in the embodiment illustrated in FIG. 1A, material has been removed from the tube leaving relatively flat surfaces 162 and 164.

As can be seen in FIGS. 1A and 1B, the flange 134 has a size, shape and orientation tailored to the particular application. For example, the flange 134 may be in a narrow elliptical or oval shape to facilitate insertion through tissue and into the desired location. The angle between the plane of the flange 134 and the longitudinal axis of the tube 132 can be relatively small, as shown in FIG. 1A, so that the major axis of the flange 134 more closely lines up with the longitudinal axis of the tube 132. For example, the angle may be in the range of 10 to 30 degrees.

An implant of a type as described herein may be implanted into a position such as that shown in FIG. 1B by a plurality of methods. For example, in an "ab externo" method, a physician forms an incision in the sclera from outside the eye. The implant is directed through the incision to the intended implantation location. The incision can be made in a location such that the inlet end is advanced first as the leading end during implantation or such that the outlet end is advanced first as the leading end during implantation. Alternatively, the incision may be made in an intermediate location, for example at a location similar to that of incision 90 in FIG. 31. Then one end of the implant may be put through the incision and generally into position, after which the other end of the implant may be put through the incision and tucked into position. To facilitate putting the second end through the incision, the first end may be forced further distally and/or the tissue may be stretched.

In an "ab interno" method, a physician forms an incision in the eye, generally in the cornea or sclera, and advances the implant through the incision, into and across the anterior chamber, and to the intended implantation location. "Ab interno" methods are disclosed, for example, in U.S. Pat. No. 4,968,296 (Ritch), U.S. Pat. No. 5,092,837 (Ritch), U.S. Pat. No. 6,007,511 (Prywes), and WO 98/30181 (Allan), the disclosures of which are hereby expressly incorporated herein by reference.

FIGS. 2A through 25C illustrate a number of alternative versions of implants. In general terms, the implants illustrated in FIGS. 2A through 25C, like the implant 130 illustrated in FIGS. 1A and 1B, comprises a needle-like tube having an inlet end, an outlet end, and a tube passage, with the tube passage having an axial inlet and an axial outlet. The implants illustrated in FIGS. 2A through 25C, may be sized similarly to the implant 130 illustrated in FIGS. 1A and 1B, for example having a length of about 2 mm to about 6 mm and a width or outer diameter of about 0.3 to about 0.6 mm. As one example, the implants illustrated in FIGS. 2A through 25C may have a length of about 4 mm and a width or outer diameter of about 0.4 mm. Again, many variations are possible, depending on the intended application and implantation site.

In the implants illustrated in FIGS. 2A through 25C, like the implant 130 illustrated in FIGS. 1A and 1B, the tube passage is sized to provide the desired flow characteristics. The tube passage may have a length and cross-sectional area designed and sized to restrict or inhibit the flow of aqueous humor through the tube passage. For example, the tube passage may have a width or diameter of about 100 micrometers to about 300 micrometers, for example about 200 micrometers. By using a specified internal cross-sectional area for the tube passage, excessive loss of aqueous humor from the eye is prevented.

The implants illustrated in FIGS. 2A through 25C, like the implant 130 illustrated in FIGS. 1A and 1B, may be implanted to direct the flow of aqueous humor from the anterior chamber into the suprachoroidal space. Each of these implants may be positioned with its inlet end in the anterior chamber adjacent the iris and its outlet end positioned to direct the flow of aqueous humor into or toward the suprachoroidal space between the choroid and the sclera.

Figure 2A:
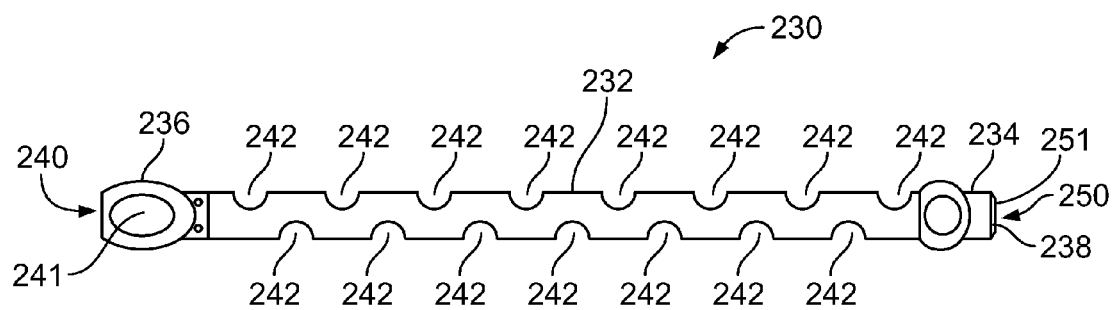
FIG. 2A is a side view of an implant in accordance with another embodiment.
Figure 2B:
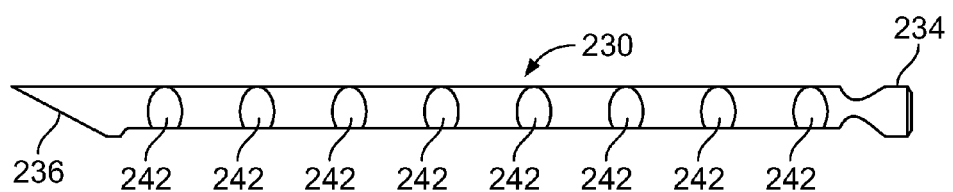
FIG. 2B is another side view of the implant of FIG. 2A.

FIGS. 2A and 2B illustrated two side views of an implant 230. The view of FIG. 2B is the view from the top of FIG. 2A, such that the view of FIG. 2B is with the implant 230 rotated 90 degrees about its longitudinal axis from the position shown in FIG. 2A. The implant 230 comprises a tube 232 with an inlet end 240, an outlet end 250, and a tube passage 238, with the tube passage 238 having an axial inlet 241 and an axial outlet 251.

The implant 230 has a beveled surface 236 at its inlet end 240. The beveled surface 236 forms a relatively pointed tip at the inlet end 240. The tip may be sharp or may be made blunt, for example by rounding it. The beveled surface 236 can aid in implantation through tissue and also can serve to prevent clogging when faced away from the iris as described above.

The implant 230 has a flange 234 at its outlet end 250. The flange 234 may be formed, for example, as a relatively conical structure having a generally oval or elliptical cross-section. Other suitable shapes may be used. The flange 234 can help anchor the outlet end of the implant in the tissue into which it is implanted.

The tube 232 has a series of side holes 242 opening into the tube passage 238 along its length. In the embodiment illustrated in FIGS. 2A and 2B, there are fifteen side holes 242, but more or fewer may be used. The side holes 242 opening into the tube passage 238 may be formed or shaped in any suitable manner. For example, they may be formed as longitudinal cuts, channels or grooves as shown in FIGS. 2A and 2B, or as bores or other suitable pathways between the tube passage 238 and the outside of the tube 232. The side holes 242 provide a plurality of fluid passageways, aiding fluid flow, helping to prevent clogging, and potentially serving as markers as described above, depending on the design and application.

Figure 3A:
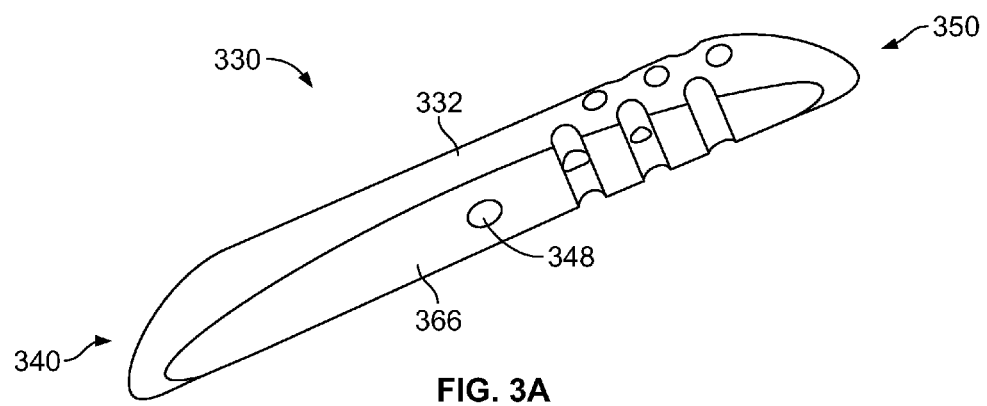
FIG. 3A is a perspective view of an implant in accordance with another embodiment.
Figure 3B:
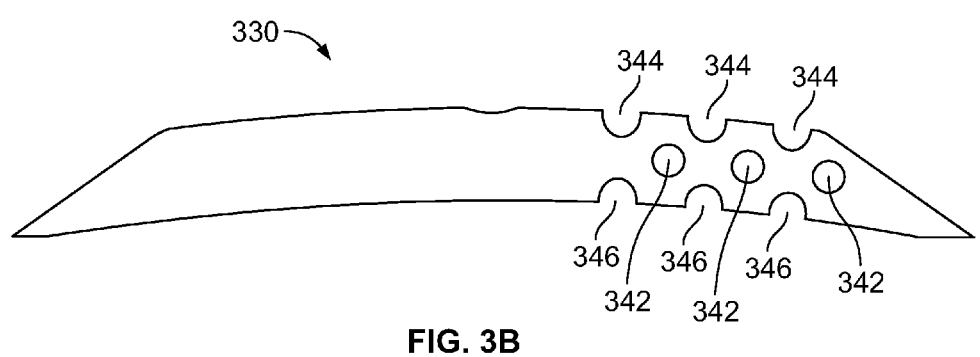
FIG. 3B is a side view of the implant of FIG. 3A.
Figure 3C:
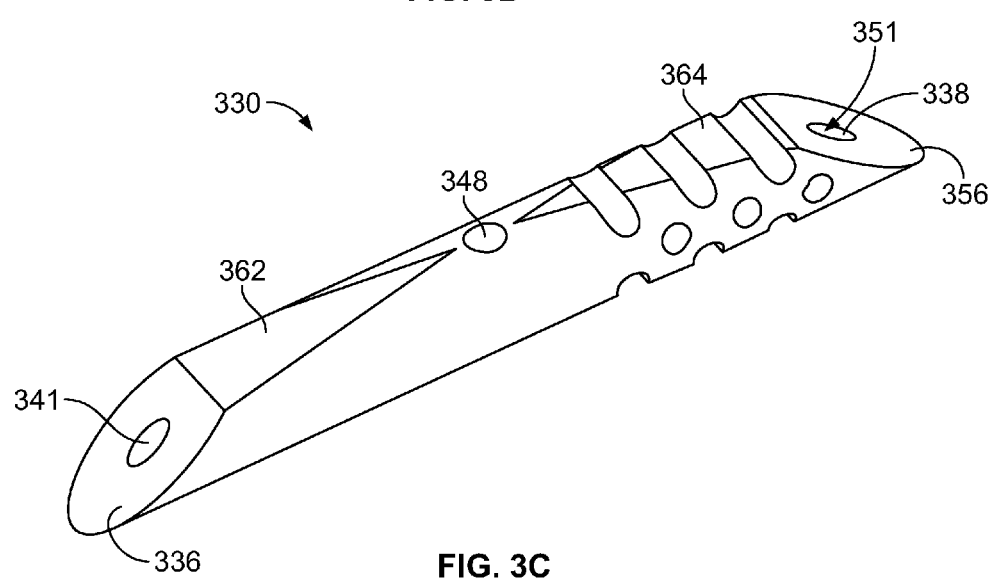
FIG. 3C is another perspective view of the implant of FIG. 3A.

FIGS. 3A through 3C illustrate another version of an implant 330. FIG. 3B shows a side view of the implant 330. FIG. 3A shows a perspective view generally from the top of the view of FIG. 3B, and FIG. 3C shows a perspective view generally from the bottom of the view of FIG. 3B. The implant 330 comprises a tube 332 with an inlet end 340, an outlet end 350, and a tube passage 338, with the tube passage 338 having an axial inlet 341 and an axial outlet 351.

As can be seen in FIG. 3B, the implant 330 has a slight curvature along its length. This can be done, for example, to generally approximate the curvature of the eye at the location where the implant is to be implanted, giving the implant a closer fit. Any or all of the implants illustrated in FIGS. 1A through 25C may be manufactured with such a curvature. In order to provide the curvature, the implant may be manufactured, e.g., molded, as a generally curved tube. Alternatively, the implant may initially be manufactured from a straight tube and then material can be removed from sides of the tube to give the implant the desired curvature. For example, in the embodiment illustrated in FIGS. 3A-3C, material has been removed from a straight tube, leaving curved surfaces 362 and 364 on one side of the implant, and curved surface 366 on an opposite side of the implant. Each of the surfaces 362 and 364 is generally on one end of the implant, closer to the axis of the straight tube at the end of the implant. The curved surface 366 is closer to the axis of the straight tube near or at the middle of the implant, tapering towards the ends of the implant.

The implant 330 has a beveled surface 336 at its inlet end 340 and a beveled surface 356 at its outlet end 350. The beveled surfaces 336, 356 form relatively pointed tips. The tips may be sharp or may be made blunt. The beveled surfaces 336, 356 can aid in implantation through tissue and can also serve to prevent clogging when faced away from the iris as described above.

The tube 332 has a series of side holes 342, 344, 346 opening into the tube passage 338, generally located proximate the outlet end 350 of the implant. The side holes 342, 344, 346 opening into the tube passage 338 may be formed or shaped in any suitable manner. For example, they may be formed as longitudinal cuts, channels, or grooves like the side holes 344 and 346, or they may be formed as bores like the side holes 342.

The side holes 342, 344, 346 provide a plurality of fluid passageways, aiding fluid flow. An additional side hole 348 can also allow fluid flow and can serve as a place for allowing the implant to be attached to a delivery device.

FIGS. 4A and 4B illustrate another version of an implant 430. FIG. 4A shows a side view of the implant 430. FIG. 4B shows a perspective view generally from the top of the view of FIG. 4A. The implant 430 comprises a tube 432 with an inlet end 440, an outlet end 450, and a tube passage 438, with the tube passage 438 having an axial inlet 441 and an axial outlet 451.

As can be seen in FIGS. 4A and 4B, the implant 430 has been made with a reduced profile along most of its length. This can be done, as described above, so that the implant takes up less space, can fit more easily into the desired location, and/or is less prone to rotation. Any or all of the implants illustrated in FIGS. 1A through 25C may be manufactured with such a reduced profile. As discussed above, the implant may be manufactured, e.g., molded, with a reduced profile tube, or the implant may initially be manufactured from a straight tube and then material can be removed from sides of the tube to give the implant the desired profile. For example, in the embodiment illustrated in FIGS. 4A-4B, material has been removed from the tube leaving relatively flat surfaces 462, 464, 466 and 468.

The implant 430 has an enlarged head or flange 434 at its outlet end 450 and an enlarged head or flange 435 at its inlet end 440. When such a flange is implanted into tissue, it can help anchor the implant. This is facilitated by the profile of the flanges 434, 435 being generally larger than the tube at the areas of the flat surfaces 462, 464, 464 and 468. The implant 430 has retention projections in the form of spurs 452 that can also assist in holding the implant 430 in tissue.

The tube 432 has a series of side holes 442, 444, 446 opening into the tube passage 438, generally located toward or proximate to the outlet end 450 of the implant. The side holes 442, 444, 446 opening into the tube passage 438 may be formed or shaped in any suitable manner. For example, they may be formed as longitudinal grooves like the side holes 444 and 446, or they may be formed as bores like the side holes 442.

The implant 430 has a beveled surface 436 at its inlet end 440 and a beveled surface 456 at its outlet end 450. The beveled surfaces 436, 456 form relatively pointed tips. The tips may be sharp or may be made blunt.

The beveled surfaces 436, 456 can aid in implantation through tissue and can also serve to prevent clogging, including when faced away from the iris as described above. The side holes 442, 444, 446 provide a plurality of fluid passageways, aiding fluid flow. An additional side hole 448 also can allow fluid flow and can serve as a place for allowing the implant to be attached to a delivery device.

In certain situations, it may be desirable to fix the implant into position by suturing or stitching it to the tissue at the implantation site. Any or all of the implants illustrated in FIGS. 1A through 25C may be affixed in this manner. The implants may be provided with narrow areas, reduced profiles, or holes for this purpose. For example, in the embodiment illustrated in FIGS. 4A-4B, the areas at side holes 444 and 446 form narrow areas and facilitate suturing the implant 430 in position.

FIGS. 5A and 5B illustrate another version of an implant 530. Implant 530 is essentially the same as implant 430, except that implant 530 does not have an enlarged head or flange at the inlet end 540, and the surfaces 562 and 566 extend all the way to the inlet end 540. When the inlet end is intended to extend into the anterior chamber, it may be considered unnecessary to use an enlarged head at the inlet end, because it is not anchored within tissue. However, in certain instances, an enlarged head at the inlet end may be advantageous. For example, it may help prevent the implant from sliding out of position in a direction away from the anterior chamber. The enlarged head or flange 435 in FIGS. 4A-4B can help keep the implant in position.

In other respects, the implant 530 is similar to the implant 430. The implant 530 comprises a tube 532 with an inlet end 540, an outlet end 550, and a tube passage 538, with the tube passage 538 having an axial inlet 541 and an axial outlet 551. The implant 530 has a reduced profile along most of its length. Material has been removed from the tube leaving flat surfaces 562, 564, 566 and 568.

The implant 530 has an enlarged head or flange 534 at its outlet end 550 which can help anchor the implant. The tube 532 has a series of side holes 542, 544, 546 opening into the tube passage 538, generally located toward or proximate to the outlet end 550 of the implant. The implant 530 has a beveled surface 536 at its inlet end 540 and a beveled surface 556 at its outlet end 550. The beveled surfaces 536, 556 form relatively pointed tips. The tips may be sharp or may be made blunt.

FIGS. 6A and 6B illustrate another version of an implant 630. Implant 630 is similar to implant 530 in many respects. The implant 630 comprises a tube 632 with an inlet end 640, an outlet end 650, and a tube passage 638 having an axial inlet 641 and an axial outlet 651. The implant 630 has a enlarged head or flange 634 at its outlet end 650 which can help anchor the implant. The tube 632 has a series of side holes 644, 645 opening into the tube passage 638, generally located toward or proximate to the outlet end 650 of the implant. The implant 630 has a beveled surface 636 at its inlet end 640 and a beveled surface 656 at its outlet end 650. The beveled surfaces 636, 656 form relatively pointed tips and may be sharp or blunt.

The implant 630 has a reduced profile along much of its length. Material has been removed from the tube leaving surfaces 662, 664, 666 and 668. As can be seen in FIGS. 6A and 6B, surfaces 664 and 668 do not extend all the way to the outlet end 650. Instead, a portion of the length of the tube 632 proximate the outlet end 650 is of an increased profile or diameter relative to the areas of the tube 632 where the surfaces 662, 664, 666 and 668 are located. In addition, the angles of the cuts forming side holes 645 create a series of spikes 652. These spikes 652 help anchor the implant 630 in tissue. In addition, they can particularly help prevent movement of the implant 630 toward its inlet end 640.

FIGS. 7A and 7B illustrate another version of an implant 730. Implant 730 is essentially the same as implant 430 shown in FIGS. 4A and 4B, except that implant 730 has a different structure at the outlet end 750. At the outlet end 750, implant 730 has an enlarged head or flange 734, but does not have a beveled surface. Outlet holes 748 are provided in the enlarged head or flange 734.

In other respects, the implant 730 is similar to the implant 430. The implant 730 comprises a tube 732 with an inlet end 740, an outlet end 750, and a tube passage 738 having an axial inlet 741 and an axial outlet 751. The implant 730 has a reduced profile along most of its length, with flat surfaces 762, 764, 766 and 768.

The implant 730 has an enlarged head or flange 735 at its inlet end 740, an enlarged head or flange 734 at its outlet end 750, and retention projections or spurs 752. The tube 732 has a series of side holes 742, 744, 746 opening into the tube passage 738, generally located toward or proximate to the outlet end 750 of the implant. The implant 730 has a beveled surface 736 at its inlet end 740, forming a relatively pointed tip, which may be sharp or blunt.

Figure 7C:
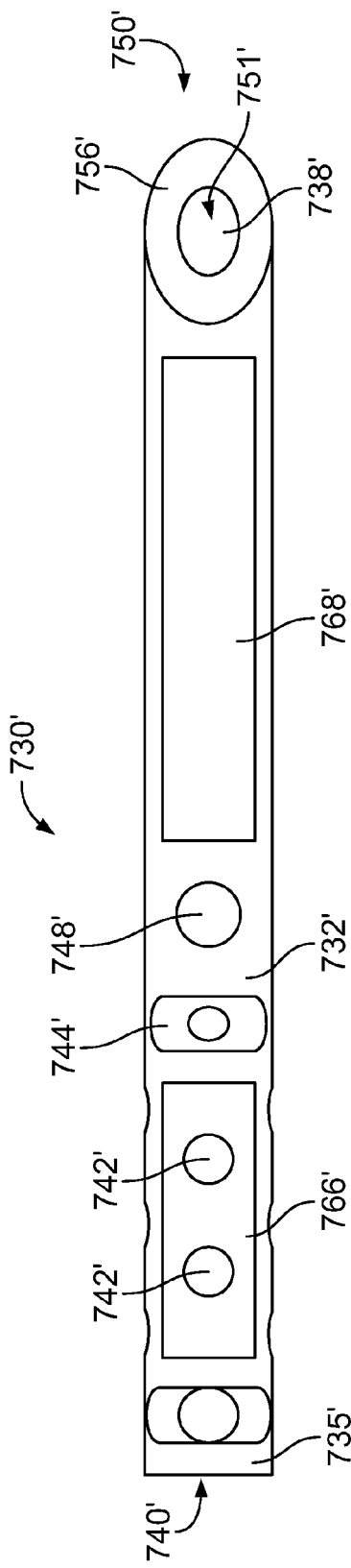
FIG. 7C is a side view of an implant in accordance with another embodiment.
Figure 7D:
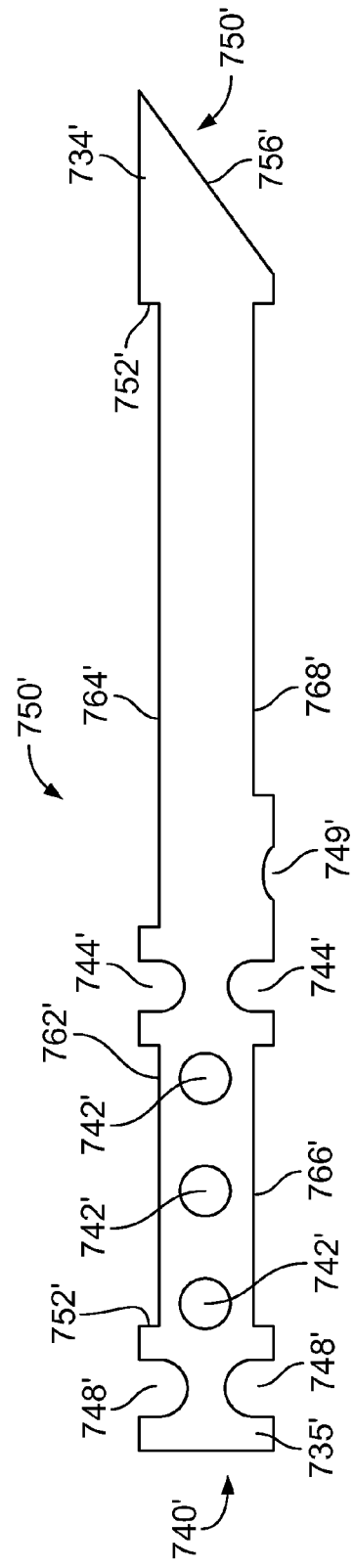
FIG. 7D is another side view of the implant of FIG. 7C.

FIGS. 7C and 7D illustrate another version of an implant 730'. Implant 730' is similar to implant 730, except that the inlet ends and outlet ends are reversed. The implant 730' comprises a tube 732' with an inlet end 740', an outlet end 750', and a tube passage 738' having an axial inlet 741' and an axial outlet 751'.

As can be seen in FIGS. 7C and 7D, the implant 730' has a reduced profile along most of its length. Material has been removed from the tube leaving surfaces 762', 764', 766' and 768'.

The implant 730' has a enlarged head or flange 734' at its outlet end 750', an enlarged head or flange 735' at its inlet end 740', and retention projections or spurs 752'. The tube 732' has a series of side holes 742', 744' opening into the tube passage 738', generally located toward or proximate to the inlet end 740' of the implant. Inlet holes 748' are provided in the enlarged head or flange 735'.

The implant 730' has a beveled surface 756' at its outlet end 750'. The beveled surface 756' forms a relatively pointed tip, which may be sharp or blunt. The beveled surface 756' can aid in implantation through tissue. The side holes 742', 744' provide a plurality of fluid passageways, aiding fluid flow. An additional side hole 749' can also allow fluid drainage and can serve as a place for allowing the implant to be attached to a delivery device. The areas at side holes 744' form narrow areas and facilitate suturing the implant 730' in position.

FIGS. 8A and 8B illustrate another version of an implant 830. Implant 830 is similar along its interior length to implant 730 and similar at its ends to implant 730'. The implant 830 comprises a tube 832 with an inlet end 840, an outlet end 850, and a tube passage 838 having an axial inlet 841 and an axial outlet 851. The implant 830 has a reduced profile along most of its length, with relatively flat surfaces 862, 864, 866 and 868.

The implant 830 has an enlarged head or flange 834 at its outlet end 850 and an enlarged head or flange 835 at its inlet end 840. The tube 832 has a series of side holes 842, 844, 846 opening into the tube passage 838, generally located toward or proximate to the outlet end 850 of the implant. Inlet holes 848 are provided in the enlarged head or flange 835.

The implant 830 has a beveled surface 856 at its outlet end 850. The beveled surface 856 forms a relatively pointed tip, which may be sharp or blunt. The beveled surface 856 can aid in implantation through tissue. The side holes 842, 844, 846 provide a plurality of fluid passageways, aiding fluid flow. An additional side hole 849 also can allow fluid flow and can serve as a place for allowing the implant to be attached to a delivery device. The areas at side holes 844, 846 form narrow areas and facilitate suturing the implant 830 in position.

FIGS. 9A through 9D show another implant 930, having similarities to other implants described herein. The implant 930 comprises a tube 932 and an enlarged head or flange 934. The tube 932 has an inlet end 940, an outlet end 950, and a tube passage 938 having an inlet 941 and an outlet 951. The flange 934 is connected to the tube 932 at its inlet end 940. The implant 930 has one or more side holes 942, and the tube 932 has a reduced profile, with flat surfaces 962, 964. The side holes 942 help prevent clogging and allow increased fluid flow.

The implant 930 has a beveled surface 956 at the outlet end 950, facilitating implantation. The implant 930 also has one or more retention projections in the form of one or more spurs 952 for retaining the implant 930 in the eye after insertion.

Figure 9C:
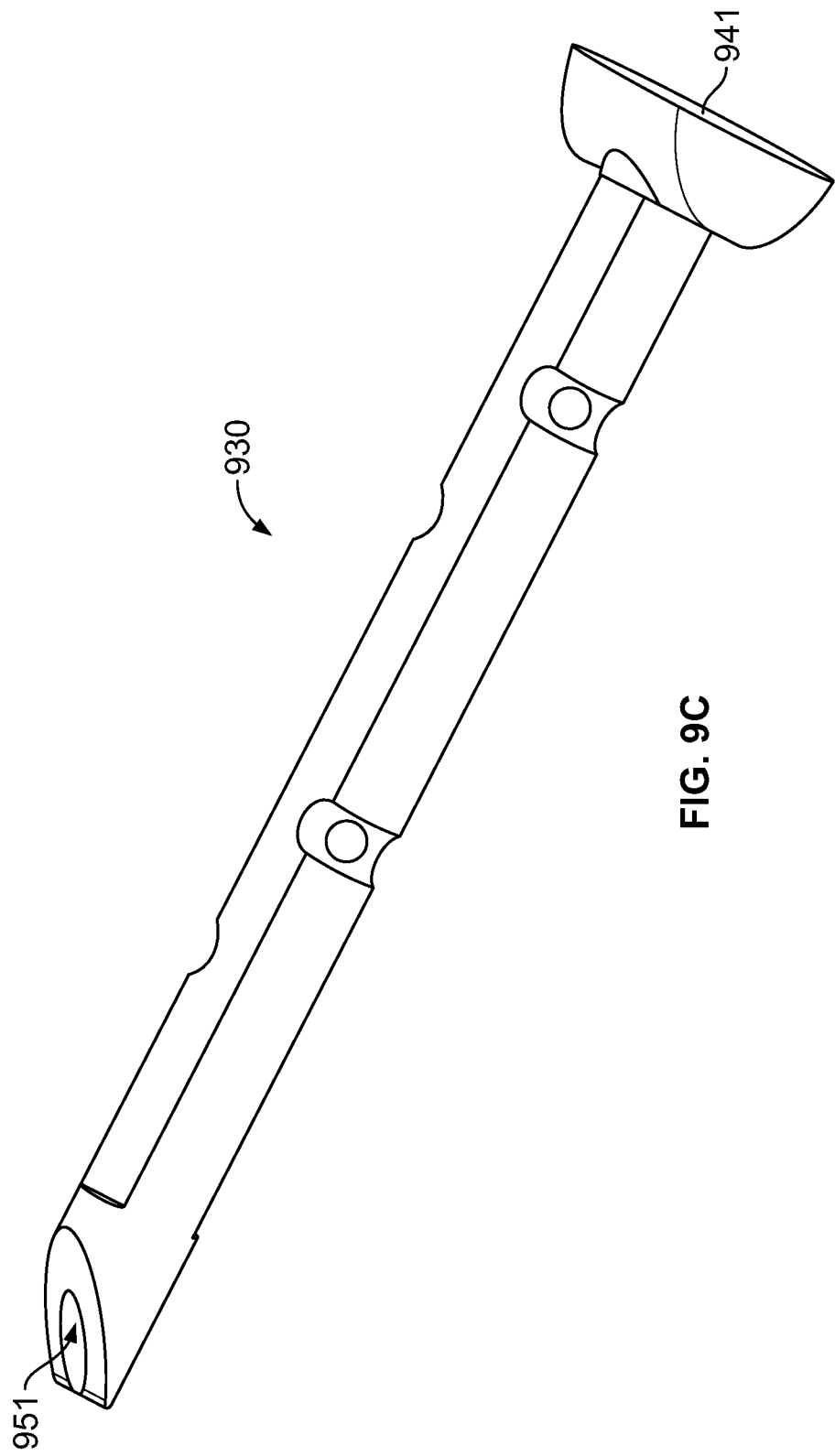
FIG. 9C is a perspective view of the implant of FIG. 9A.

In the embodiment of FIGS. 9A-9C, the flange 934 is designed like a plug. As shown, it has a semi-cylindrical shape, with the axis of the semi-cylinder being oriented perpendicular to the longitudinal axis of the tube 932, giving the implant 930 a T-shape. The rounded side of the enlarged head or flange 934 faces the tube 934 so that it presses into the tissue, e.g., the trabecular meshwork. In addition to being rounded, the side of the enlarged head or flange at the inlet end that faces the tube may be tapered or conical. Having the side of the enlarged head or flange at the inlet end that faces the tube be rounded, tapered or conical allows the enlarged head or flange to be partially or completely touching the tissue, e.g., the trabecular meshwork.

As discussed above, any suitable dimensions for the implants may be used. For example, the length of the tube 932 may be approximately 4.5 mm, and the width of the tube 932 may be approximately 0.4 mm. In the embodiment of FIGS. 9A-9C, the flange 934 may have, for example, a length of about 1 mm. Other dimensions may be used.

Figure 9D:
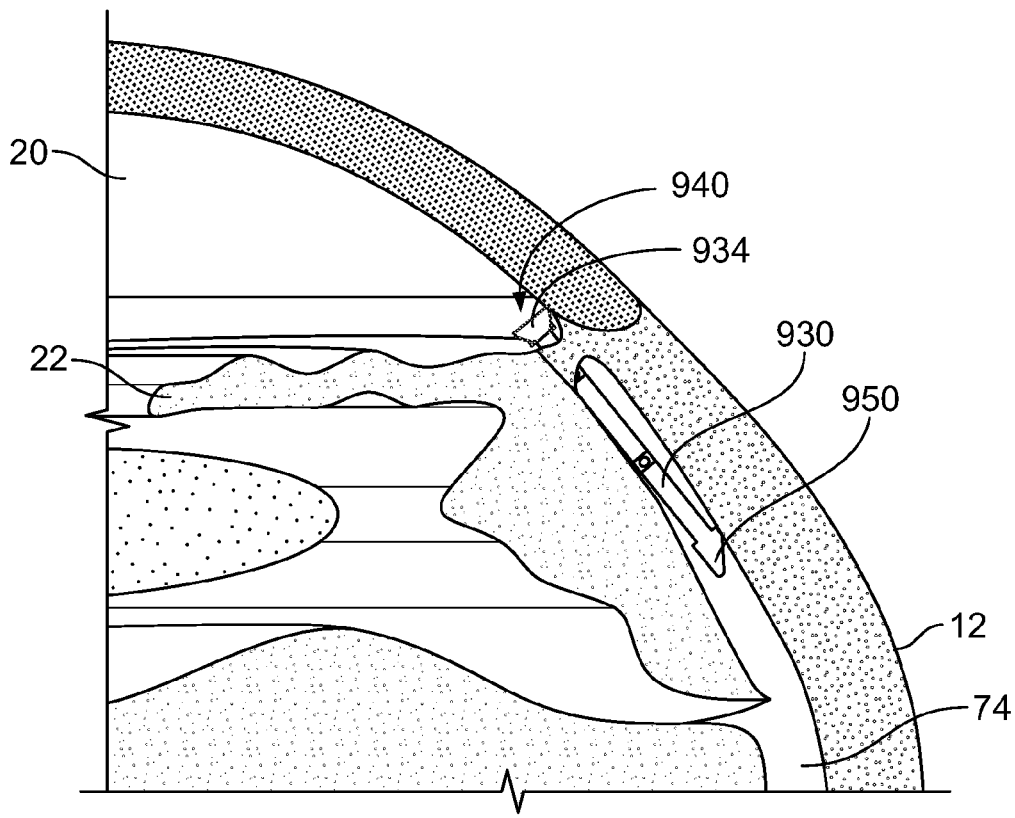
FIG. 9D shows the implant of FIG. 9A implanted in an eye.

FIG. 9D shows the implant 930 implanted to direct the flow of aqueous humor into a suprachoroidal space 74. FIG. 9D shows the implant 930 positioned with its inlet end 940 in the anterior chamber 20 adjacent the iris 22 and its outlet end 950 positioned to direct the flow of aqueous humor into or toward the suprachoroidal space 74 between the choroid 72 and the sclera 12. The flange 934 serves as a plug to help position the implant and keep it in place. The flange 934 rests against the tissue, e.g., the trabecular meshwork or other tissue through which the implant 930 is implanted.

FIGS. 10A through 10D show an implant 1030 similar to the implant 930, but with a relatively flat enlarged head or flange 1034 at its inlet end 1040. The implant 1030 comprises a tube 1032 with an inlet end 1040, an outlet end 1050, and a tube passage 1038 having an inlet 1041 and an outlet 1051. The flange 1034 is connected to the tube 1032 at its inlet end 1040. The implant 1030 has one or more side holes 1042, and a reduced profile with flat surfaces 1062, 1064. The side holes 1042 help prevent clogging and allow increased fluid flow.

The implant 1030 has a beveled surface 1056 at the outlet end 1050, facilitating implantation. The implant 1030 also has one or more retention projections in the form of one or more spurs 1052 for retaining the implant 1030 in the eye after insertion.

The flange 1034 is designed like a relatively flat plate. As shown, the flange 1034 has a generally rectangular shape, with rounded sides, and is oriented perpendicular to the tube 1032, giving the implant a T-shape. The dimensions may be similar to those described above, and the flange 1034 may have, for example, a length of about 1 mm. Other dimensions may be used.

Figure 10D:
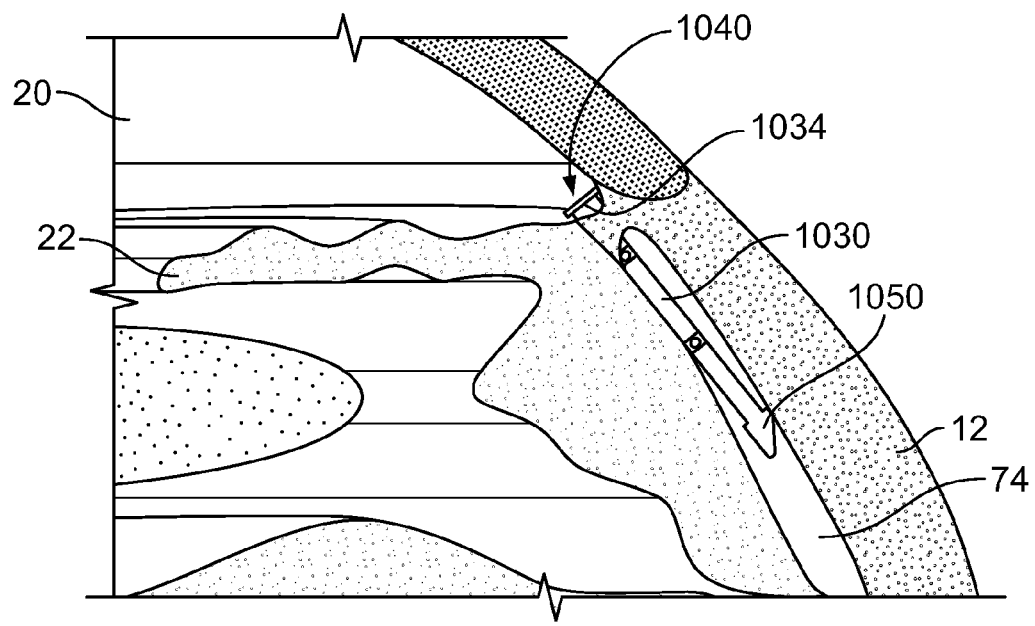
FIG. 10D shows the implant of FIG. 10A implanted in an eye.
Figure 10A:
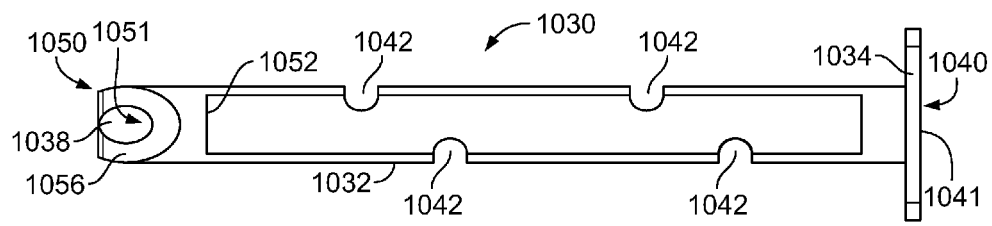
FIG. 10A is a side view of an implant in accordance with another embodiment.
Figure 10B:
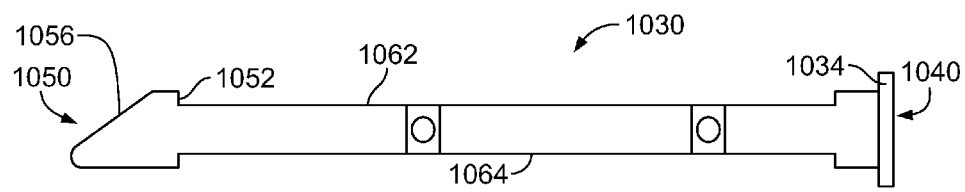
FIG. 10B is another side view of the implant of FIG. 10A.
Figure 10C:
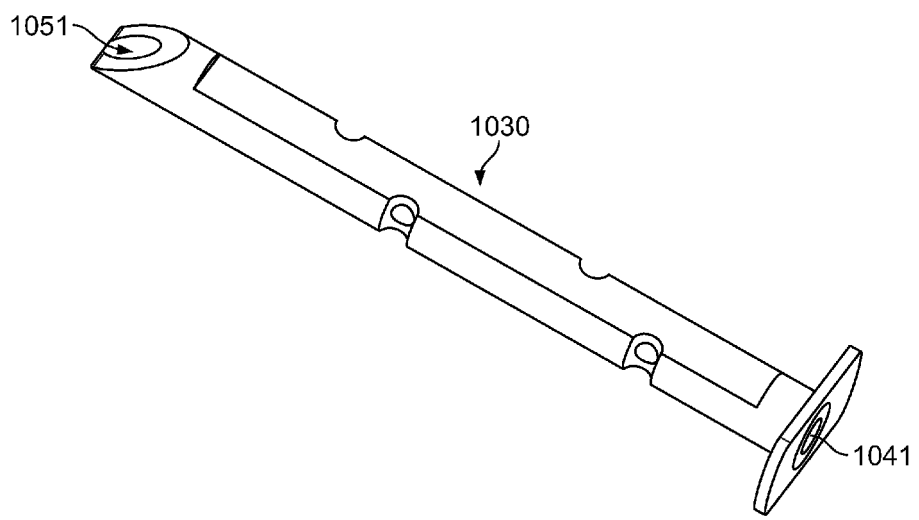
FIG. 10C is a perspective view of the implant of FIG. 10A.

FIG. 10D shows the implant 1030 implanted to direct the flow of aqueous humor into a suprachoroidal space 74. FIG. 10D shows the implant 1030 positioned with its inlet end 1040 in the anterior chamber 20 adjacent the iris 22 and its outlet end 1050 positioned to direct the flow of aqueous humor into or toward the suprachoroidal space 74 between the choroid 72 and the sclera 12. The flange 1034 helps position the implant and keep it in place. The flange 1034 rests against the tissue, e.g., the trabecular meshwork or other tissue through which the implant 1030 is implanted.

Figure 11A:
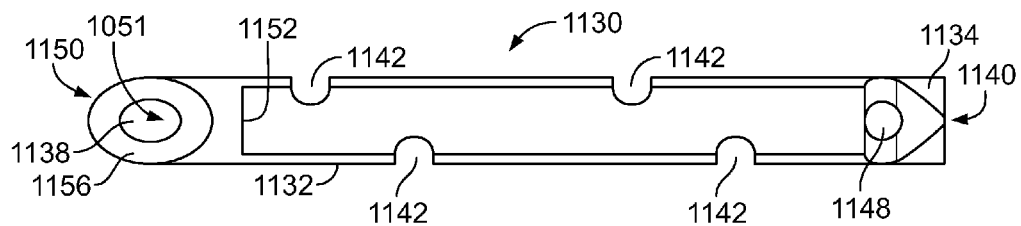
FIG. 11A is a side view of an implant in accordance with another embodiment.
Figure 11B:
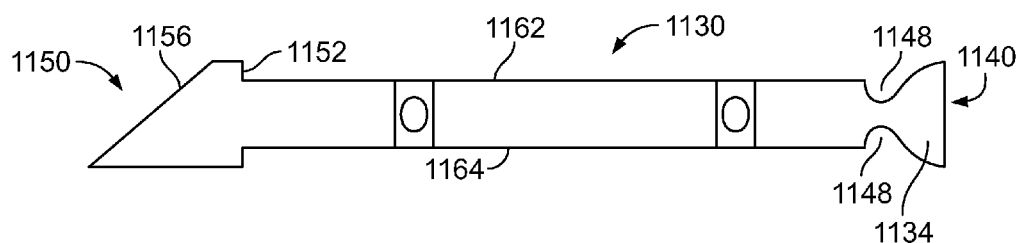
FIG. 11B is another side view of the implant of FIG. 11A.
Figure 11C:
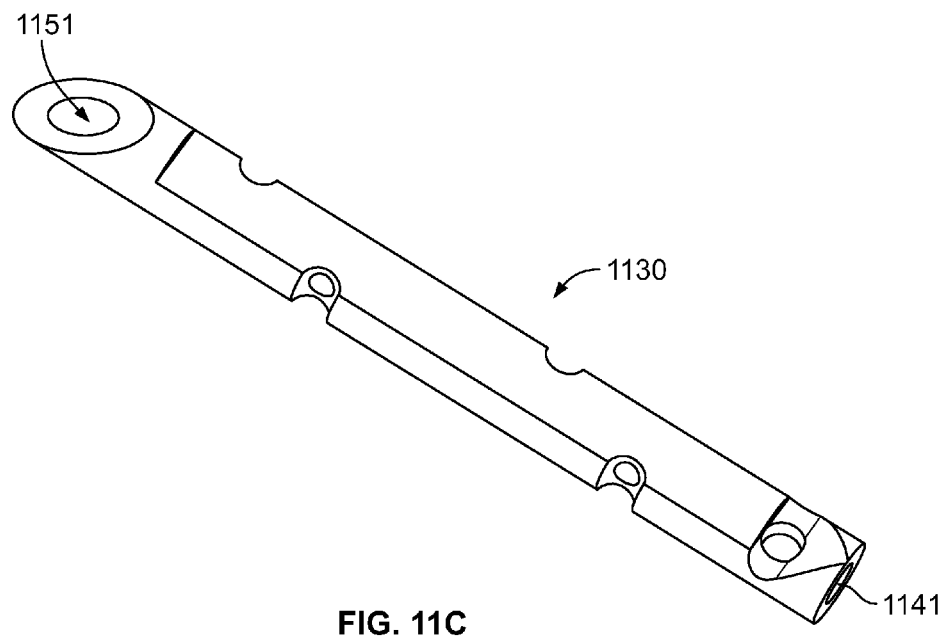
FIG. 11C is a perspective view of the implant of FIG. 11A.

FIGS. 11A through 11C show an implant 1130 similar to the implants 930 and 1030. The implant 1130 comprises a tube 1132 having an inlet end 1140, an outlet end 1150, and a tube passage 1138 with an inlet 1141 and an outlet 1151. An enlarged head or flange 1134 is connected to the tube 1132 at its inlet end 1140. The implant 1130 has one or more side holes 1142, and a reduced profile with flat surfaces 1162, 1164. The side holes 1142 help prevent clogging and allow increased fluid flow. The flat surfaces provide a reduced profile and, similar to other flat surfaces described herein like flat surfaces 962, 964, 1062 and 1064, help prevent rotation of the implant.

The implant 1130 has a beveled surface 1156 at the outlet end 1150, facilitating implantation through tissue. The implant 1130 also has one or more retention projections in the form of one or more spurs 1152 for helping retain the implant 1130 in the eye after insertion. The flange 1134 helps position the implant at the inlet end. Side holes 1148 may be provided to allow alternative inlet flow. Also, the underside of the flange 1134 is rounded to help position the implant 1130 and help avoid tissue injury. In addition, as mentioned above, having the side of the enlarged head or flange at the inlet end that faces the tube be rounded, tapered or conical allows the enlarged head or flange to partially or completely contact the tissue, e.g., the trabecular meshwork.

FIGS. 12A through 12D illustrate another implant 1230, having similarities to the implant 130 in FIG. 1A. Implant 1230 comprises a tube 1232 and an enlarged head or disk or flange 1234. The plane of the flange 1234 forms an angle with the tube 1232. The tube 1232 has an inlet end 1240, an outlet end 1250, and a tube passage 1238 having an axial inlet 1241 and an axial outlet 1251. The flange 1234 is connected to the tube 1232 at its outlet end 1250. The implant 1230 has a reduced profile with flat surfaces 1262, 1264. The dimensions may be similar to those in FIG. 1A, except the tip is sharper.

The implant 1230 has one or more side holes 1242, which help prevent clogging, assist in fluid flow and can be used as a marker. The implant 1230 has a beveled surface 1236 at the inlet end 1240. The beveled surface 1236 increases the area of the axial inlet 1241 to enlarge the entrance to the tube passage 1238. The implant 1230 can be implanted such that the beveled surface 1236 faces away from the iris. The implant 1230 also has one or more retention projections in the form of one or more spurs 1252 for retaining the implant 1230 in the eye after insertion.

The flange 1234 may be in a narrow elliptical or oval shape to facilitate insertion through tissue and into the desired location. The angle between the plane of the flange 1234 and the longitudinal axis of the tube 1232 can be relatively small, so that the major axis of the flange 1234 more closely lines up with the longitudinal axis of the tube 1232.

Figure 12A:
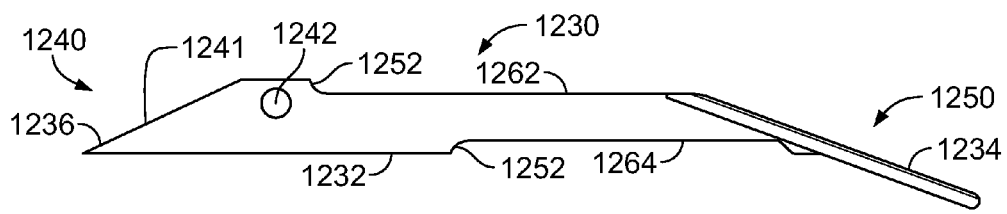
FIG. 12A is a side view of an implant in accordance with another embodiment.
Figure 12B:
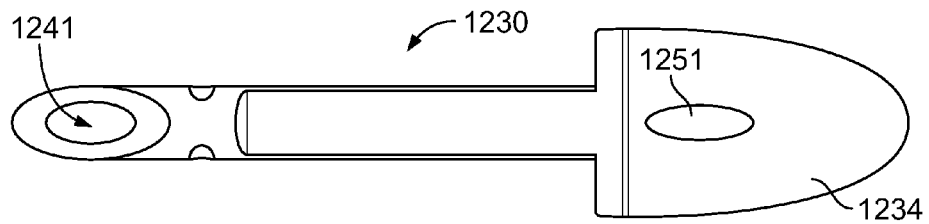
FIG. 12B is another side view of the implant of FIG. 12A.
Figure 12C:
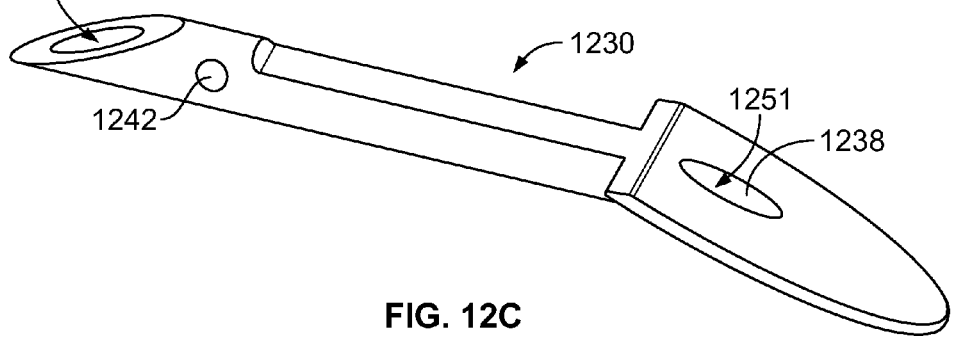
FIG. 12C is a perspective view of the implant of FIG. 12A.
Figure 12D:
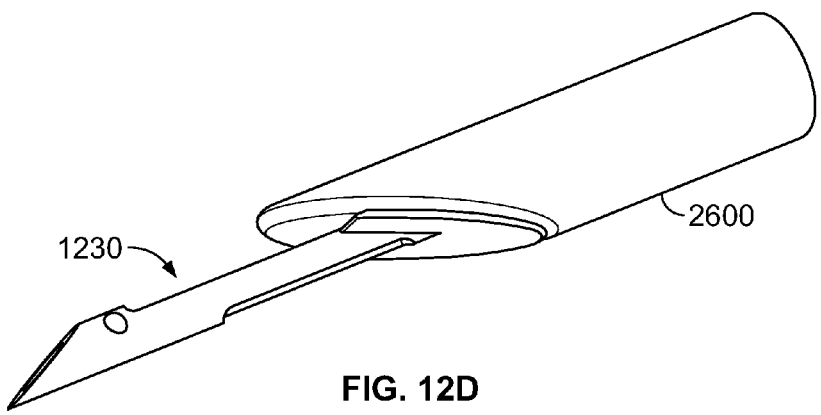
FIG. 12D shows the implant of FIG. 12A on a delivery device.

FIG. 12D shows the implant 1230 on a delivery device 2600. The delivery device 2600 and its use are described in more detail in connection with FIGS. 26A and 26B.

FIGS. 13A through 13D illustrate another implant 1330, having similarities to the implant 1230. Implant 1330 comprises a tube 1332 and an enlarged head, disk or flange 1334. The plane of the flange 1334 forms an angle with the tube 1332. The tube 1332 has an inlet end 1340, an outlet end 1350, and a tube passage 1338 having an axial inlet 1341 and an axial outlet 1351. The flange 1334 is connected to the tube 1332 at its outlet end 1350. The implant 1330 has a reduced profile with flat surfaces 1362, 1364. The shape and dimensions may be similar to those in FIG. 1A, except that the inlet end does not have a beveled surface but instead has a rounded tip 1337.

The implant 1330 has one or more side holes 1342, which help prevent clogging, assist in fluid flow and can be used as a marker. The implant 1330 also has one or more retention projections in the form of one or more spurs 1352 for helping retain the implant 1330 in the eye after insertion.

The flange 1334 may be in a narrow elliptical or oval shape to facilitate insertion through tissue and into the desired location. The angle between the plane of the flange 1334 and the longitudinal axis of the tube 1332 can be relatively small, so that the major axis of the flange 1334 more closely lines up with the longitudinal axis of the tube 1232.

The rounded tip 1337 helps prevent damage to the cornea and/or iris. Any of the implants described herein may be provided with a rounded tip at the inlet end to help prevent damage to the cornea and/or iris.

Figure 13A:
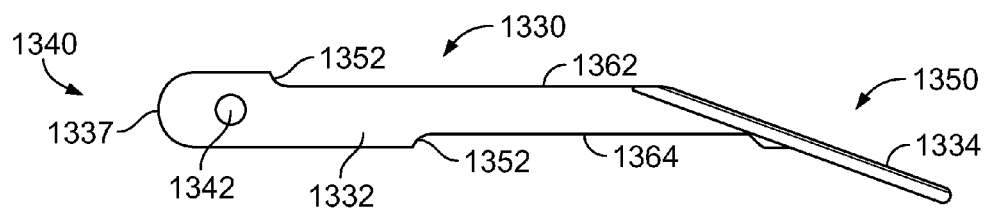
FIG. 13A is a side view of an implant in accordance with another embodiment.
Figure 13B:
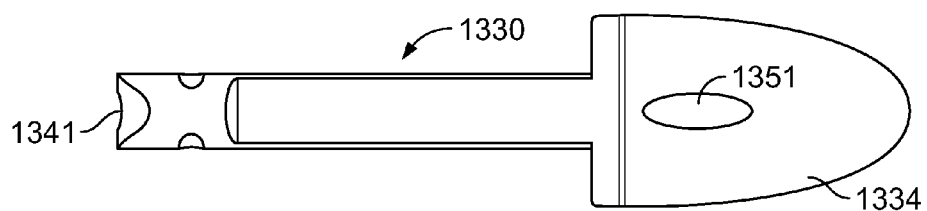
FIG. 13B is another side view of the implant of FIG. 13A.
Figure 13C:
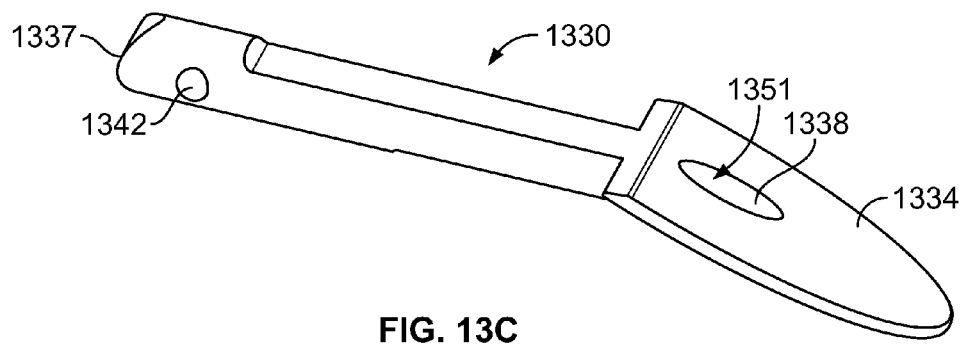
FIG. 13C is a perspective view of the implant of FIG. 13A.
Figure 13D:
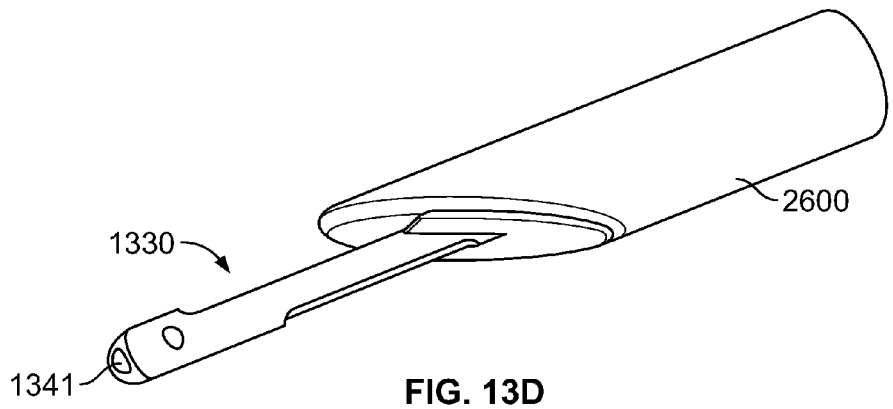
FIG. 13D shows the implant of FIG. 13A on a delivery device.

FIG. 13D shows the implant 1330 on a delivery device 2600. The delivery device 2600 and its use are described in more detail in connection with FIGS. 26A and 26B.

FIGS. 14A through 14D illustrate another implant 1430, having similarities to the implants 130, 1230 and 1330. Implant 1430 comprises a tube 1432 and an enlarged head, disk or flange 1434. The plane of the flange 1434 forms an angle with the tube 1432. The tube 1432 has an inlet end 1440, an outlet end 1450, and a tube passage 1438 having an axial inlet 1441 and an axial outlet 1451. The flange 1434 is connected to the tube 1432 at its outlet end 1450. The inlet end 1440 has a rounded tip 1437. The implant 1430 has a reduced profile with flat surfaces 1462, 1464. The general shape and dimensions may be similar to that of implants 130, 1230 and 1330.

The implant 1430 has one or more side holes 1442, which help prevent clogging, assist in fluid flow and can be used as a marker. The implant 1430 also has one or more retention projections in the form of one or more spurs 1452 for helping retain the implant 1430 in the eye after insertion.

The flange 1434 in this embodiment projects exclusively or primarily on one side of the implant. The flange 1434 may be in the form of a portion of a circle, oval or ellipse.

Figure 14A:
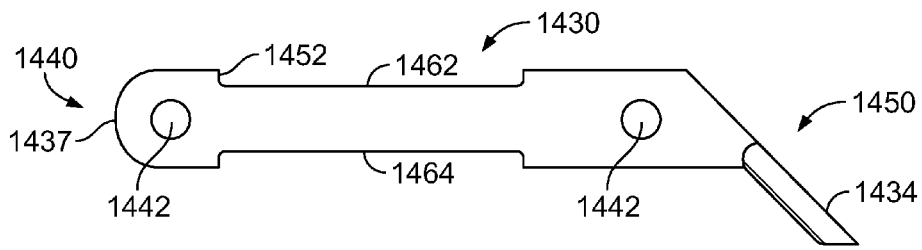
FIG. 14A is a side view of an implant in accordance with another embodiment.
Figure 14B:
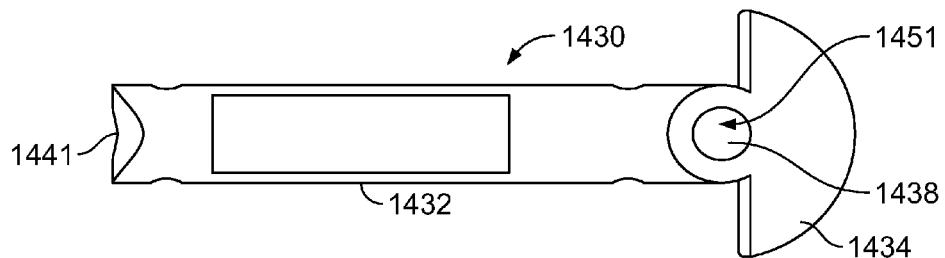
FIG. 14B is another side view of the implant of FIG. 14A.
Figure 14C:
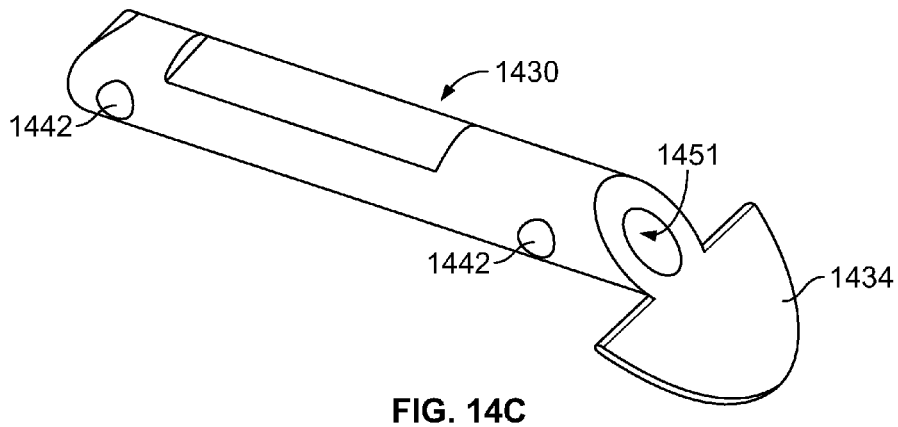
FIG. 14C is a perspective view of the implant of FIG. 14A.
Figure 14D:
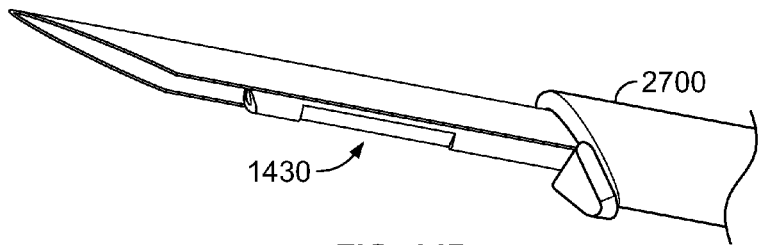
FIG. 14D shows the implant of FIG. 14A on a delivery device.

FIG. 14D shows the implant 1430 on a delivery device 2700. The shape of the flange 1434 facilitates loading the implant in this type of delivery device. The delivery device 2700 and its use are described in more detail in connection with FIG. 27.

FIGS. 15A through 15D illustrate another implant 1530, having similarities to the implants 130, 1230, 1330 and 1430. Implant 1530 comprises a tube 1532 and an enlarged head, disk or flange 1534. The plane of the flange 1534 forms an angle with the tube 1532. The tube 1532 has an inlet end 1540, an outlet end 1550, and a tube passage 1538 having an axial inlet 1541 and an axial outlet 1551. The flange 1534 is connected to the tube 1532 at its outlet end 1550. The inlet end 1540 has a rounded tip 1537. The implant 1530 has a reduced profile with flat surfaces 1562, 1564. The general shape and dimensions may be similar to those of implants 130, 1230, 1330 and 1430.

The implant 1530 has one or more side holes 1542, which help prevent clogging, assist in fluid flow and can be used as a marker. The implant 1530 also has one or more retention projections in the form of one or more spurs 1552 for helping retain the implant 1530 in the eye after insertion.

Figure 15A:
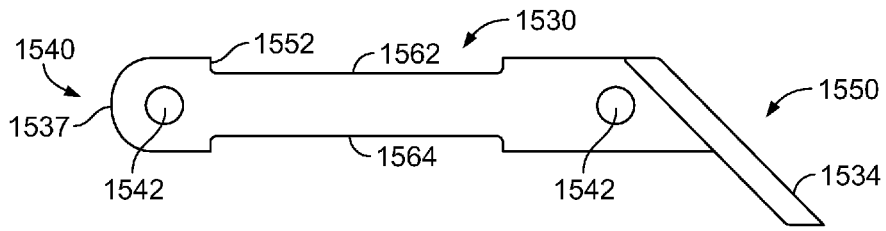
FIG. 15A is a side view of an implant in accordance with another embodiment.
Figure 15B:
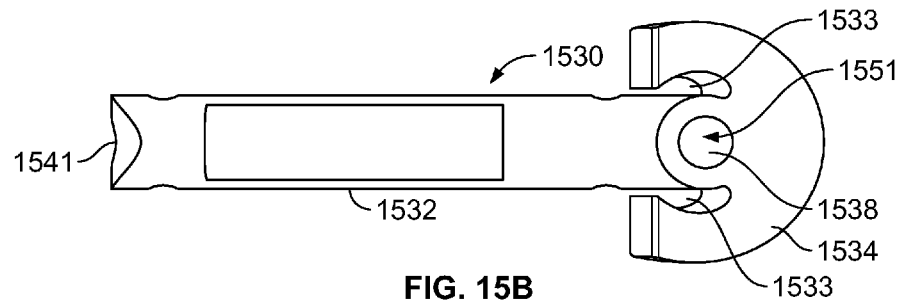
FIG. 15B is another side view of the implant of FIG. 15A.
Figure 15C:
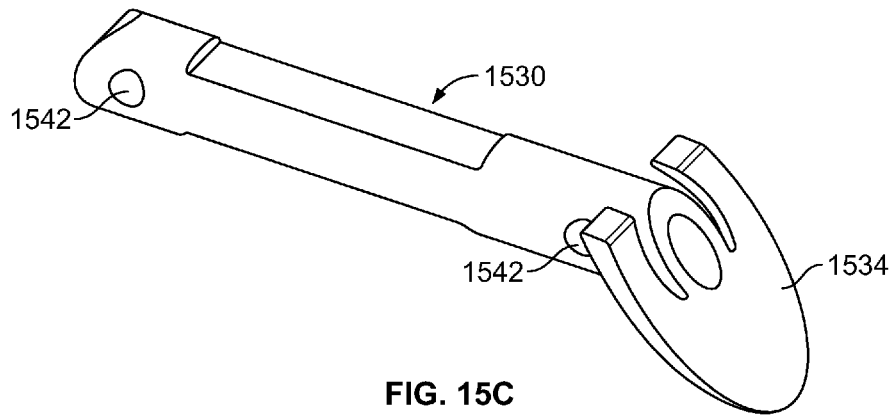
FIG. 15C is a perspective view of the implant of FIG. 15A.
Figure 15D:
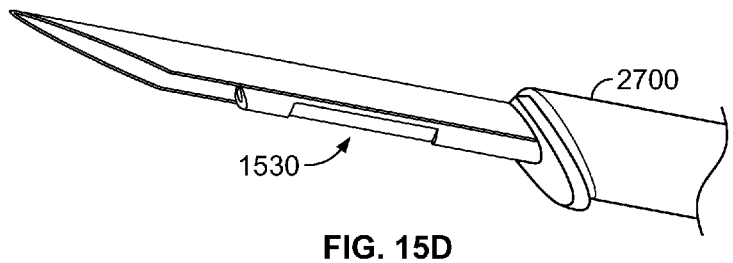
FIG. 15D shows the implant of FIG. 15A on a delivery device.

The flange 1534 may be, for example, in the form of a circle, oval or ellipse, or a portion thereof. The flange 1534 in this embodiment has grooves or access pockets 1533 which receive the wall of a delivery device 2700 as shown in FIG. 15D. This helps retain the implant on the delivery device and assists in a safer device detachment.

FIG. 15D shows the implant 1530 on a delivery device 2700. The shape of the flange 1534 facilitates attaching the implant to this type of delivery device. The delivery device 2700 and its use are described in more detail in connection with FIG. 27.

FIGS. 16A through 16D illustrate another implant 1630, having similarities to the implants 130, 1230, 1330, 1430 and 1530. Implant 1630 comprises a tube 1632 and an enlarged head, disk or flange 1634. The plane of the flange 1634 forms an angle with the tube 1632. The tube 1632 has an inlet end 1640, an outlet end 1650, and a tube passage 1638 having an axial inlet 1641 and an axial outlet 1651. The flange 1634 is connected to the tube 1632 at its outlet end 1650. The inlet end 1640 has a beveled surface 1636 and a rounded tip 1637. The implant 1630 has a reduced profile with flat surfaces 1662, 1664. The general shape and dimensions may be similar to that of implants 130, 1230, 1330, 1430 and 1530.

Figure 16A:
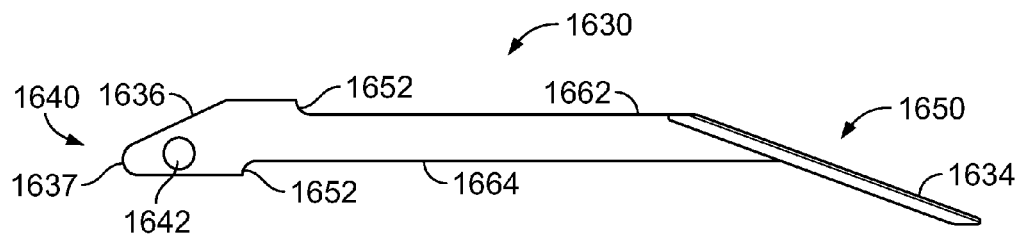
FIG. 16A is a side view of an implant in accordance with another embodiment.
Figure 16B:
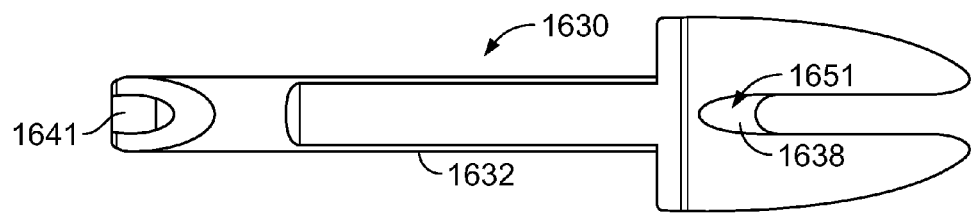
FIG. 16B is another side view of the implant of FIG. 16A.
Figure 16C:
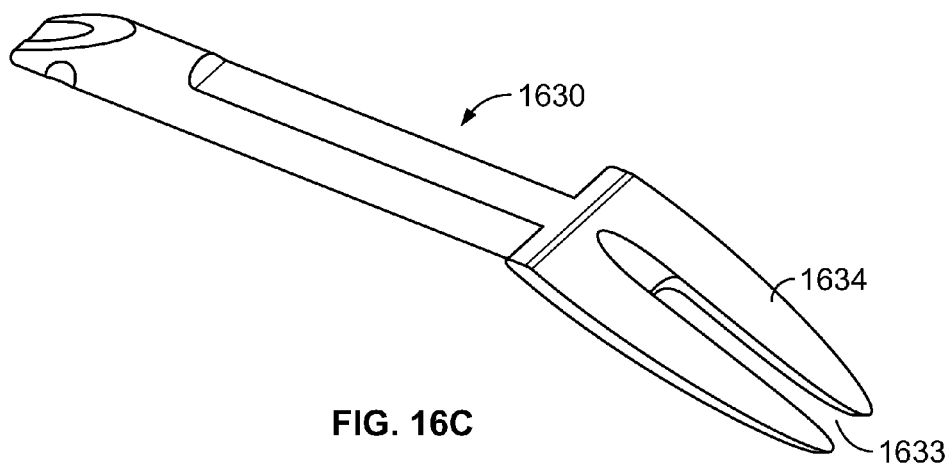
FIG. 16C is a perspective view of the implant of FIG. 16A.

The implant 1630 has one or more side holes 1642, which help prevent clogging, assist in fluid flow and can be used as a marker. The implant 1630 also has one or more retention projections in the form of one or more spurs 1652 for helping retain the implant 1630 in the eye after insertion. As can be seen in FIG. 16A, the spurs 1652 are unaligned. The shape and positioning of the retention projections or spurs can be selected, for example, depending on the location in which the implant is to be implanted, the desired angle, and the general shape and contour of the tissue to which the retention projections or spurs are intended to be adjacent.

The flange 1634 may be, for example, in the form of a circle, oval or ellipse, or a portion thereof. The flange 1634 in this embodiment has a groove 1633 which facilitates fluid drainage. The groove 1633 allows fluid flow to the opposite side of the flange 1634.

Figure 16D:
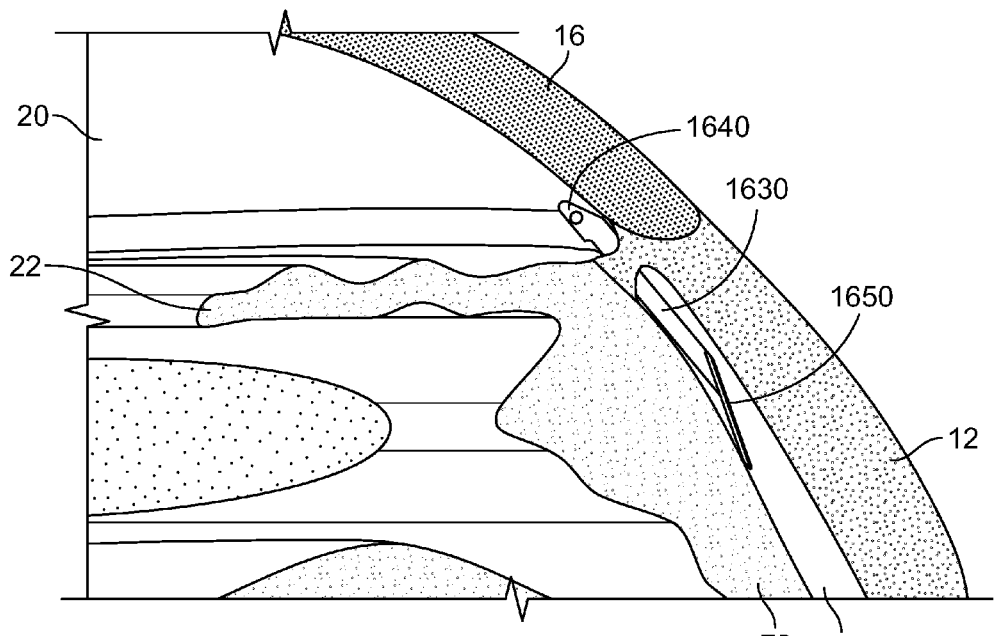
FIG. 16D shows the implant of FIG. 16A implanted in an eye.

FIG. 16D shows the implant 1630 implanted to direct the flow of aqueous humor into the suprachoroidal space. FIG. 16D shows the implant 1630 positioned with its inlet end 1640 in the anterior chamber 20 adjacent the iris 22 and its outlet end 1650 positioned to direct the flow of aqueous humor into or toward the suprachoroidal space 74 between the choroid 72 and the sclera 12. In FIG. 16D, the implant 1630 is implanted so that the beveled surface 1636 faces away from the iris 22, toward the cornea 16.

FIGS. 17A through 17D illustrate another implant 1730, similar to the implant 1630, except that upon implantation the beveled surface 1736 faces toward the iris 22 instead of toward the cornea 16. Implant 1730 comprises a tube 1732 and an enlarged head, disk or flange 1734. The plane of the flange 1734 forms an angle with the tube 1732. The tube 1732 has an inlet end 1740, an outlet end 1750, and a tube passage 1738 having an axial inlet 1741 and an axial outlet 1751. The flange 1734 is connected to the tube 1732 at its outlet end 1750. The inlet end 1740 has a beveled surface 1736 and a rounded tip 1737. The implant 1730 has a reduced profile with flat surfaces 1762, 1764. The general shape and dimensions may be similar to those of implant 1630.

The implant 1730 has one or more side holes 1742, which help prevent clogging, assist in fluid flow and can be used as a marker. The implant 1730 also has one or more retention projections in the form of one or more spurs 1752 for helping retain the implant 1730 in the eye after insertion. As can be seen in FIG. 17A, the spurs 1752 are unaligned.

The flange 1734 may be, for example, in the form of a circle, oval or ellipse, or a portion thereof. The flange 1734 in this embodiment has a groove 1733 which facilitates fluid drainage.

Figure 17D:
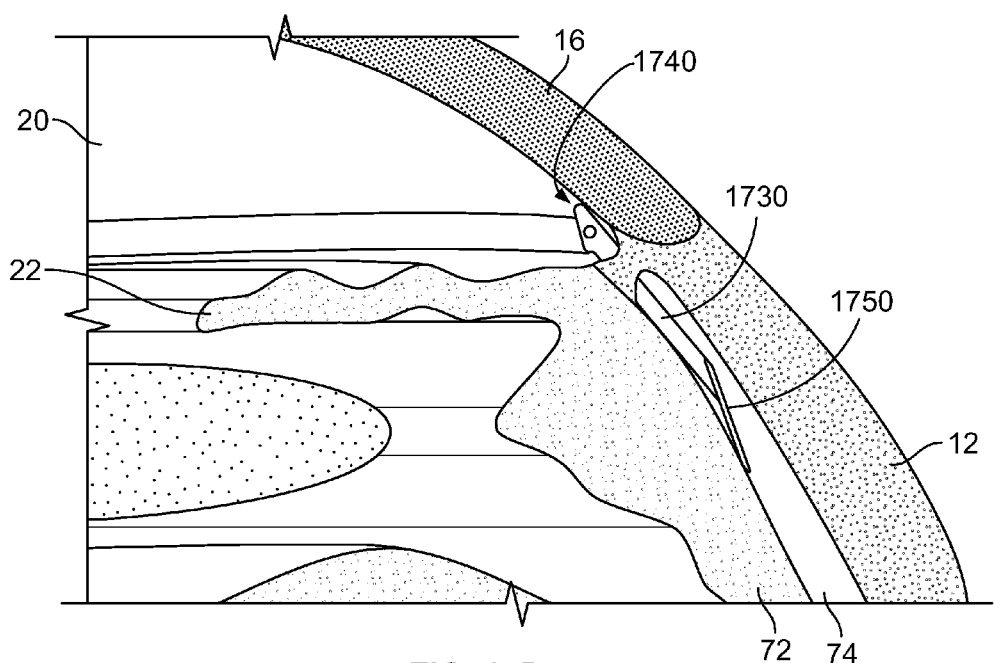
FIG. 17D shows the implant of FIG. 17A implanted in an eye.
Figure 17A:
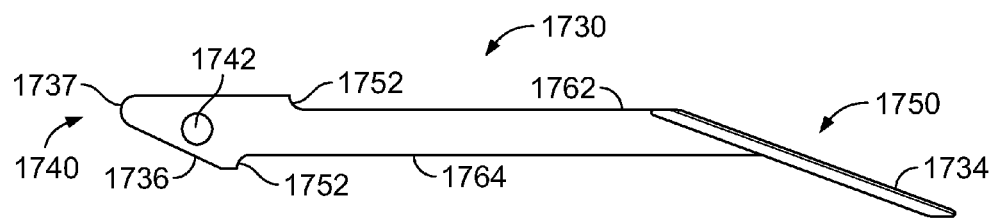
FIG. 17A is a side view of an implant in accordance with another embodiment.
Figure 17B:
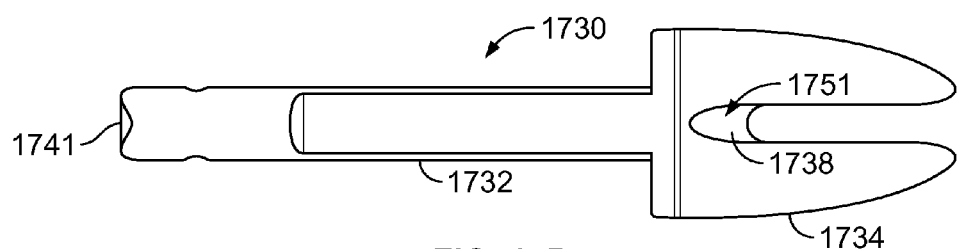
FIG. 17B is another side view of the implant of FIG. 17A.
Figure 17C:
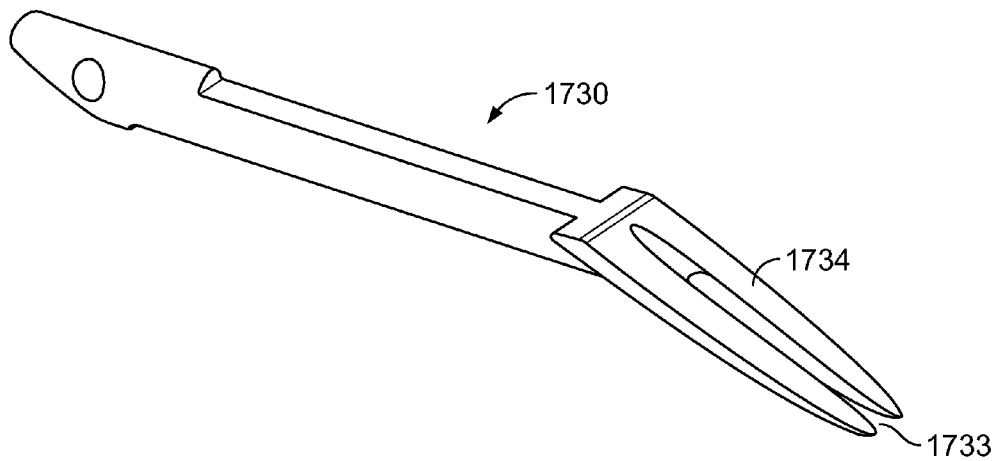
FIG. 17C is a perspective view of the implant of FIG. 17A.

FIG. 17D shows the implant 1730 implanted to direct the flow of aqueous humor into the suprachoroidal space. FIG. 17D shows the implant 1730 positioned with its inlet end 1740 in the anterior chamber 20 adjacent the iris 22 and its outlet end 1750 positioned to direct the flow of aqueous humor into or toward the suprachoroidal space 74 between the choroid 72 and the sclera 12. As can be seen in FIG. 17D, upon implantation the beveled surface 1736 faces toward the iris 33 instead of toward the cornea 16, as in FIG. 16D.

FIGS. 18A through 18D illustrate another implant 1830, similar to the implant 130. Implant 1830 comprises a tube 1832 and an enlarged head, disk or flange 1834. The plane of the flange 1834 forms an angle with the tube 1832. The tube 1832 has an inlet end 1840, an outlet end 1850, and a tube passage 1838 having an axial inlet 1841 and an axial outlet 1851. The flange 1834 is connected to the tube 1832 at its outlet end 1850. The inlet end 1840 has a beveled surface 1836 and a rounded tip 1837. The implant 1830 has a reduced profile with flat surfaces 1862, 1864. The general shape and dimensions may be similar to those of implant 130.

The implant 1830 has one or more side holes 1842, which help prevent clogging, assist in fluid flow and can be used as a marker. The implant 1830 also has one or more retention projections in the form of one or more spurs 1852 for helping retain the implant 1830 in the eye after insertion.

The flange 1834 may be, for example, in the form of a circle, oval or ellipse, or a portion thereof. Other suitable shapes are possible.

Figure 18A:
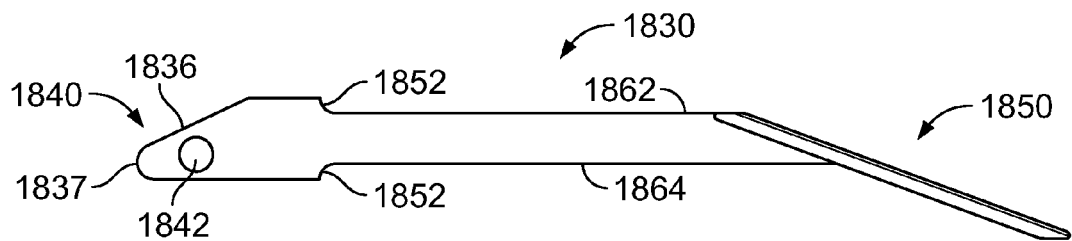
FIG. 18A is a side view of an implant in accordance with another embodiment.
Figure 18B:
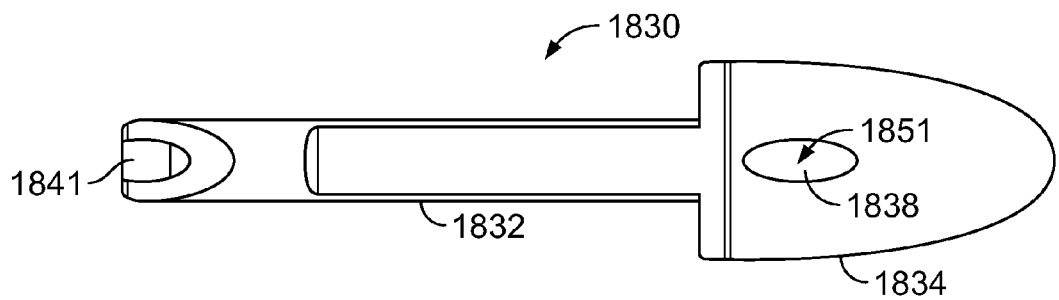
FIG. 18B is another side view of the implant of FIG. 18A.
Figure 18C:
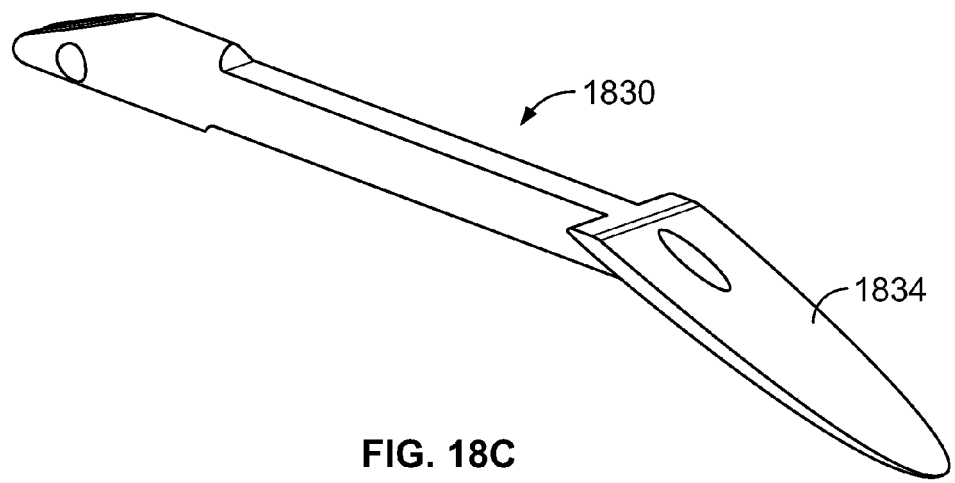
FIG. 18C is a perspective view of the implant of FIG. 18A.
Figure 18D:
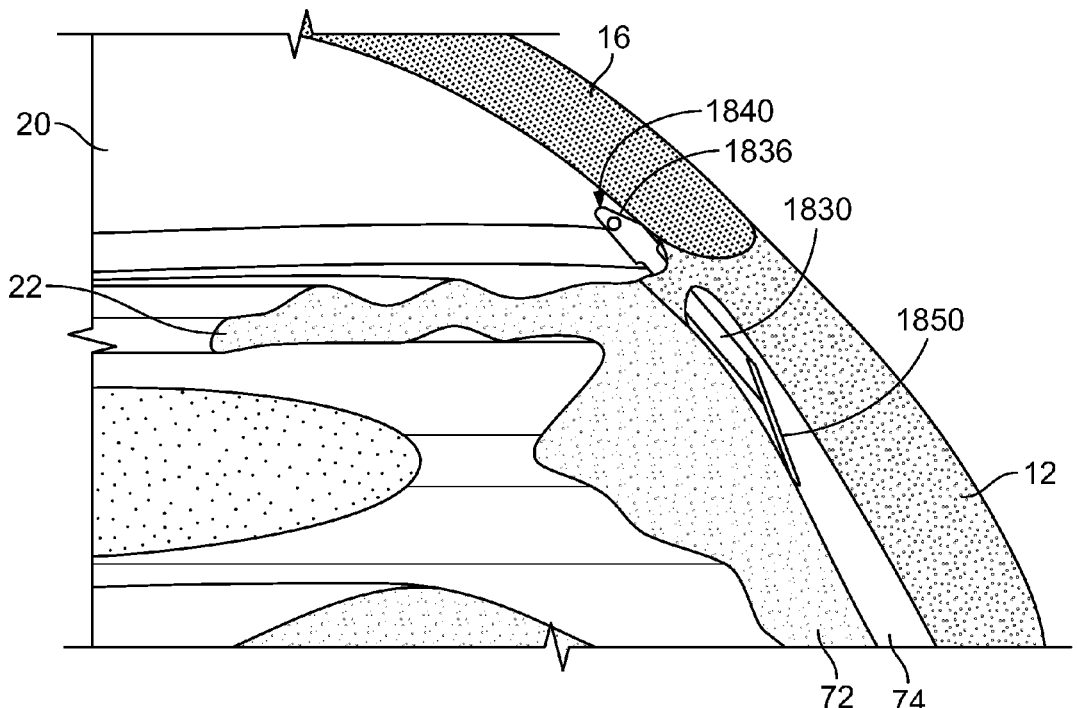
FIG. 18D shows the implant of FIG. 18A implanted in an eye.

FIG. 18D shows the implant 1830 implanted to direct the flow of aqueous humor into the suprachoroidal space. FIG. 18D shows the implant 1830 positioned with its inlet end 1840 in the anterior chamber 20 adjacent the iris 22 and its outlet end 1850 positioned to direct the flow of aqueous humor into or toward the suprachoroidal space 74 between the choroid 72 and the sclera 12. As can be seen in FIG. 18D, upon implantation the beveled surface 1836 faces toward the cornea 16.

FIGS. 19A through 19D illustrate another implant 1930, having similarities to the implant 1630. Implant 1930 is curved at the inlet end 1940 so that beveled surface 1936 is farther away from the cornea, to prevent contact between the implant and the cornea. Implant 1930 comprises a tube 1932 and an enlarged head, disk or flange 1934. The plane of the flange 1934 forms an angle with the tube 1932. The tube 1932 has an inlet end 1940, an outlet end 1950, and a tube passage 1938 having an axial inlet 1941 and an axial outlet 1951. The flange 1934 is connected to the tube 1932 at its outlet end 1950. The inlet end 1940 has a beveled surface 1936 and a rounded tip 1937. The implant 1930 has a reduced profile with flat surfaces 1962, 1964. The general shape and dimensions may be similar to those of implant 1630.

The implant 1930 has one or more side holes 1942, which help prevent clogging, assist in fluid flow and can be used as a marker. The implant 1930 also has one or more retention projections in the form of one or more spurs 1952 for helping retain the implant 1930 in the eye after insertion.

The flange 1934 may be, for example, in the form of a circle, oval or ellipse, or a portion thereof. The flange 1934 in this embodiment has a groove 1933 which facilitates fluid drainage.

Figure 19D:
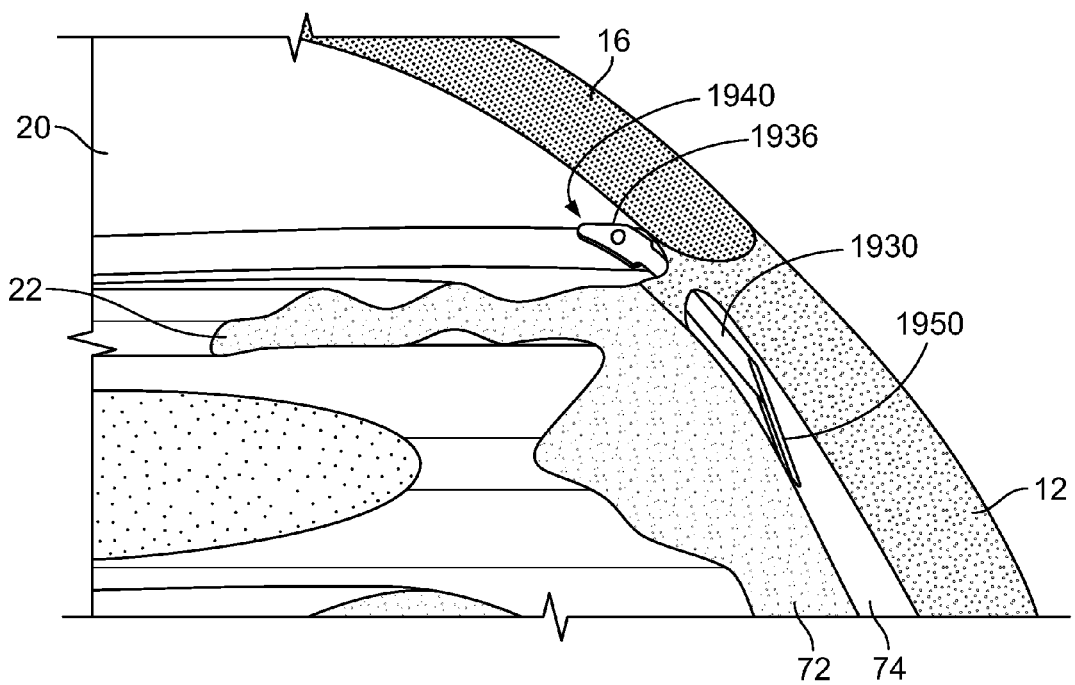
FIG. 19D shows the implant of FIG. 19A implanted in an eye.
Figure 19A:
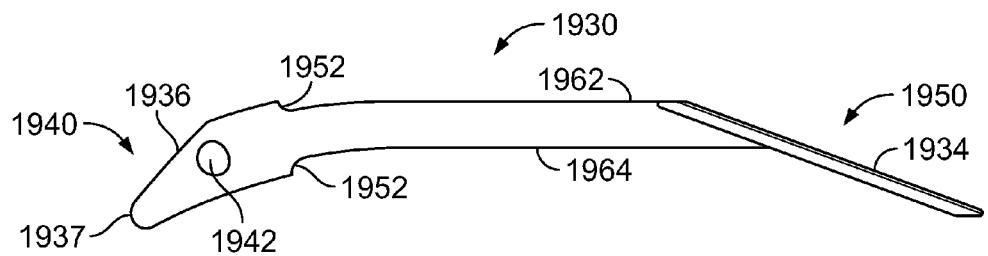
FIG. 19A is a side view of an implant in accordance with another embodiment.
Figure 19B:
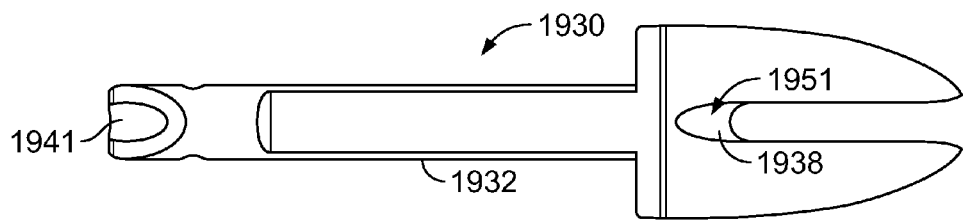
FIG. 19B is another side view of the implant of FIG. 19A.
Figure 19C:
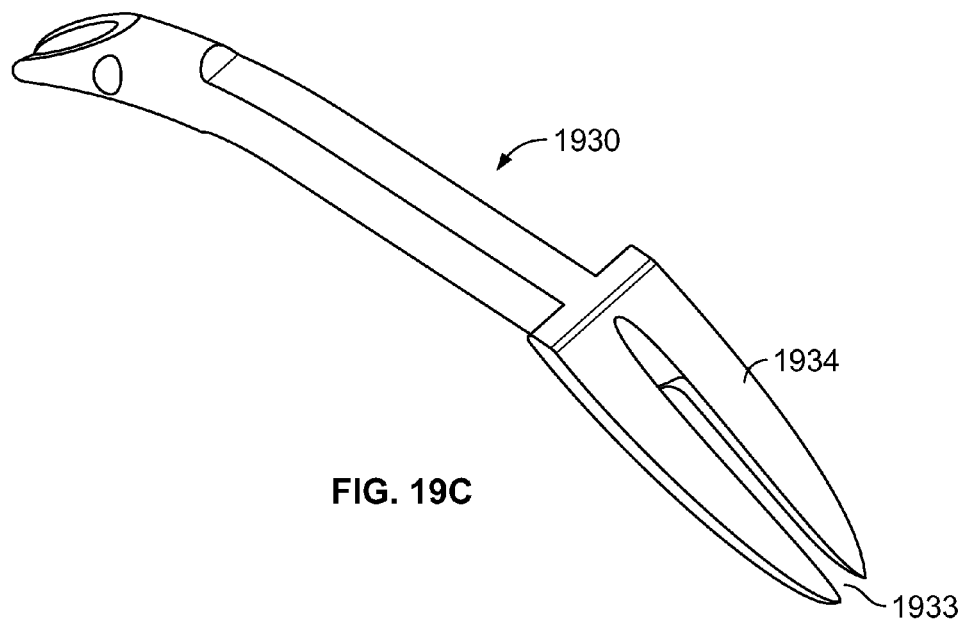
FIG. 19C is a perspective view of the implant of FIG. 19A.

FIG. 19D shows the implant 1930 implanted to direct the flow of aqueous humor into the suprachoroidal space. FIG. 19D shows the implant 1930 positioned with its inlet end 1940 in the anterior chamber 20 adjacent the iris 22 and its outlet end 1950 positioned to direct the flow of aqueous humor into or toward the suprachoroidal space 74 between the choroid 72 and the sclera 12. As can be seen in FIG. 19D, the curvature of the implant 1930 at the inlet end 1940 keeps the inlet end 1940 from contacting the cornea 16.

FIGS. 20A through 20D illustrate another implant 2030, similar to the implant 1830, except that upon implantation the beveled surface 1836 faces toward the iris instead of toward the cornea. Implant 2030 comprises a tube 2032 and an enlarged head, disk or flange 2034. The plane of the flange 2034 forms an angle with the tube 2032. The tube 2032 has an inlet end 2040, an outlet end 2050, and a tube passage 2038 having an axial inlet 2041 and an axial outlet 2051. The flange 2034 is connected to the tube 2032 at its outlet end 2050. The inlet end 2040 has a beveled surface 2036 and a rounded tip 2037. The implant 2030 has a reduced profile with flat surfaces 2062, 2064. The general shape and dimensions may be similar to those of implant 1830.

The implant 2030 has one or more side holes 2042, which help prevent clogging, assist in fluid flow and can be used as a marker. The implant 2030 also has one or more retention projections in the form of one or more spurs 2052 for helping retain the implant 2030 in the eye after insertion.

The flange 2034 may be, for example, in the form of a circle, oval or ellipse, or a portion thereof. Other suitable shapes are possible.

Figure 20A:
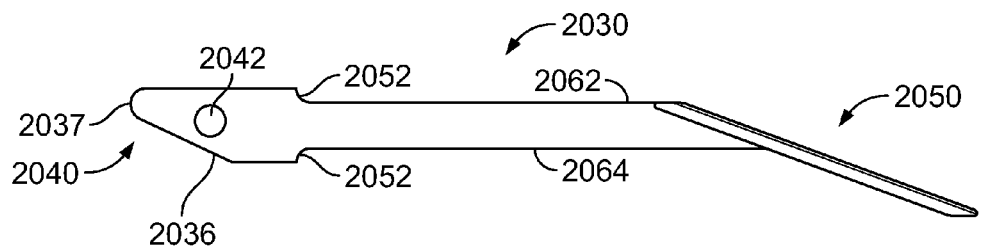
FIG. 20A is a side view of an implant in accordance with another embodiment.
Figure 20B:
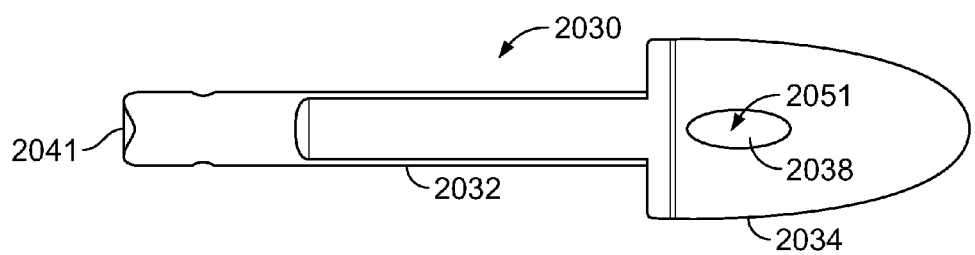
FIG. 20B is another side view of the implant of FIG. 20A.
Figure 20C:
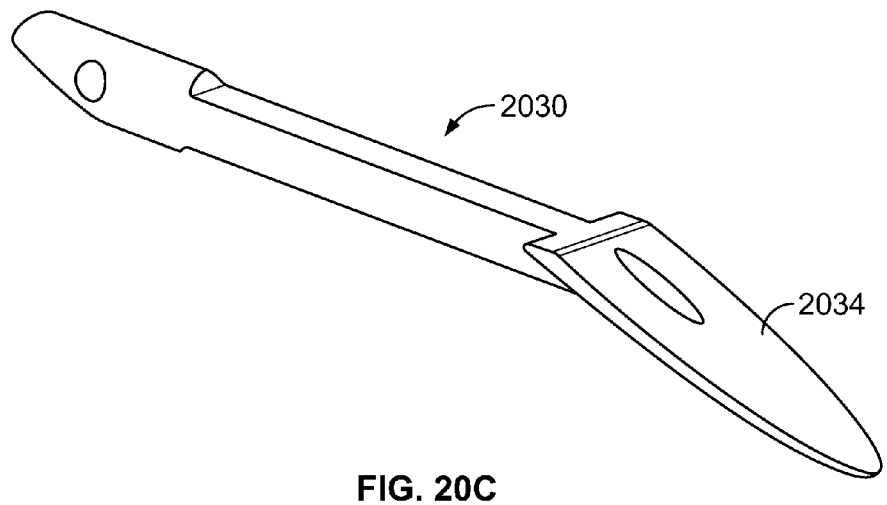
FIG. 20C is a perspective view of the implant of FIG. 20A.
Figure 20D:
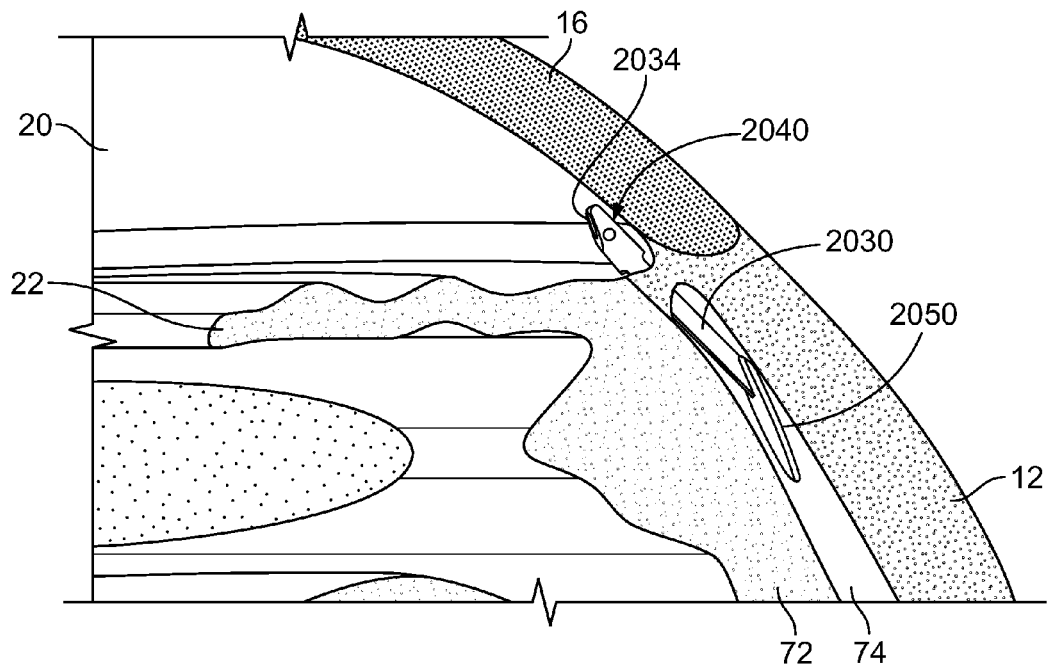
FIG. 20D shows the implant of FIG. 20A implanted in an eye.

FIG. 20D shows the implant 2030 implanted to direct the flow of aqueous humor into the suprachoroidal space. FIG. 20D shows the implant 2030 positioned with its inlet end 2040 in the anterior chamber 20 adjacent the iris 22 and its outlet end 2050 positioned to direct the flow of aqueous humor into or toward the suprachoroidal space 74 between the choroid 72 and the sclera 12. As can be seen in FIG. 20D, upon implantation the beveled surface 2036 faces toward the iris 22, away from the cornea 16.

FIGS. 21A through 21D illustrate another implant 2130, similar to the implant 1730, except that the implant 2130 has a smaller profile at the inlet end 2140 and only one spur 2152. Implant 2130 comprises a tube 2132 and an enlarged head, disk or flange 2134. The plane of the flange 2134 forms an angle with the tube 2132. The tube 2132 has an inlet end 2140, an outlet end 2150, and a tube passage 2138 having an axial inlet 2141 and an axial outlet 2151. The flange 2134 is connected to the tube 2132 at its outlet end 2150. The inlet end 2140 has a beveled surface 2136 and a rounded tip 2137. The implant 2130 has a reduced profile with flat surfaces 2162, 2164. The general shape and dimensions may be similar to that of implant 1730, except with a reduced profile and single spur 2152 at the inlet end 2140.

The implant 2130 has one or more side holes 2142, which help prevent clogging, assist in fluid flow and can be used as a marker. The implant 2130 also has a retention projection in the form of a spur 2152 for helping retain the implant 1730 in the eye after insertion.

The flange 2134 may be, for example, in the form of a circle, oval or ellipse, or a portion thereof. The flange 2134 in this embodiment has a groove 2133 which facilitates fluid drainage.

Figure 21D:
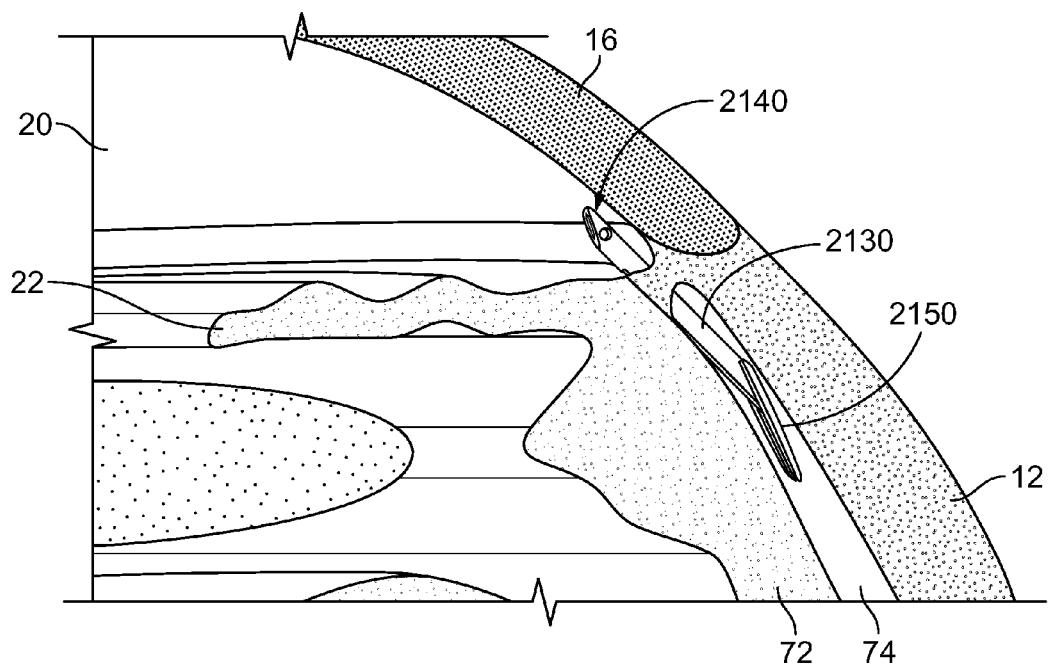
FIG. 21D shows the implant of FIG. 21A implanted in an eye.
Figure 21A:
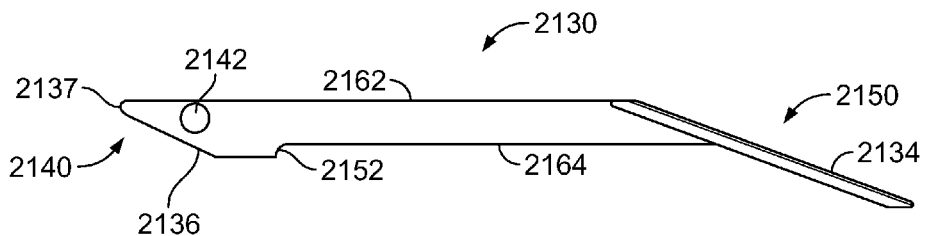
FIG. 21A is a side view of an implant in accordance with another embodiment.
Figure 21B:
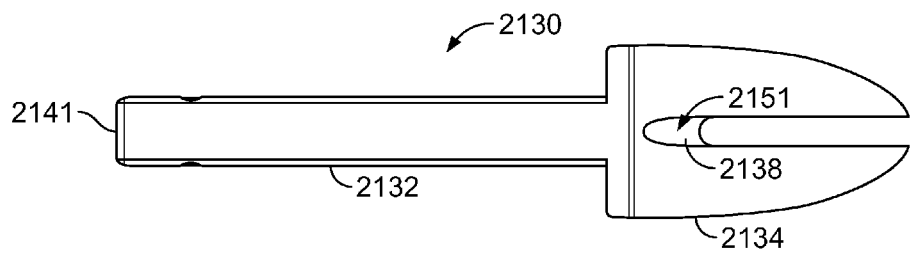
FIG. 21B is another side view of the implant of FIG. 21A.
Figure 21C:
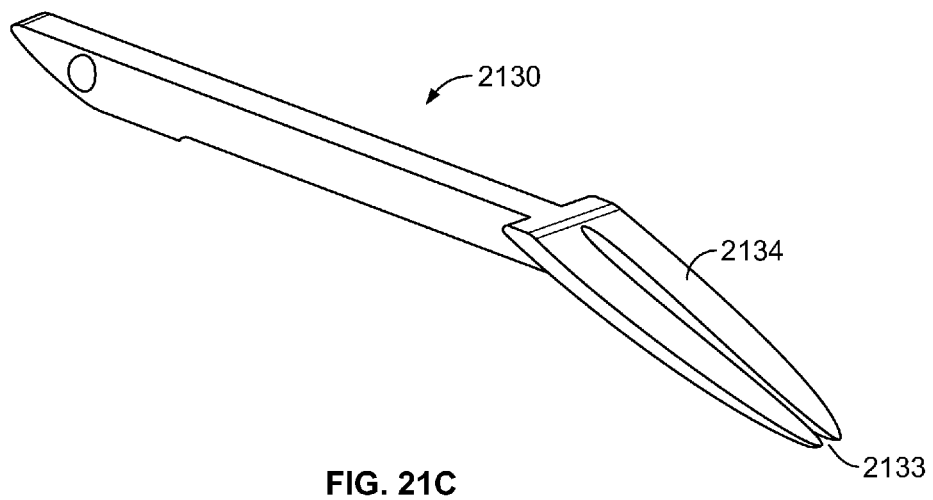
FIG. 21C is a perspective view of the implant of FIG. 21A.

FIG. 21D shows the implant 2130 implanted to direct the flow of aqueous humor into the suprachoroidal space. FIG. 21D shows the implant 2130 positioned with its inlet end 2140 in the anterior chamber 20 adjacent the iris 22 and its outlet end 2150 positioned to direct the flow of aqueous humor into or toward the suprachoroidal space 74 between the choroid 72 and the sclera 12. As can be seen in FIG. 21D, upon implantation the beveled surface 2136 faces toward the iris 22 and away from the cornea 16.

Figure 22A:
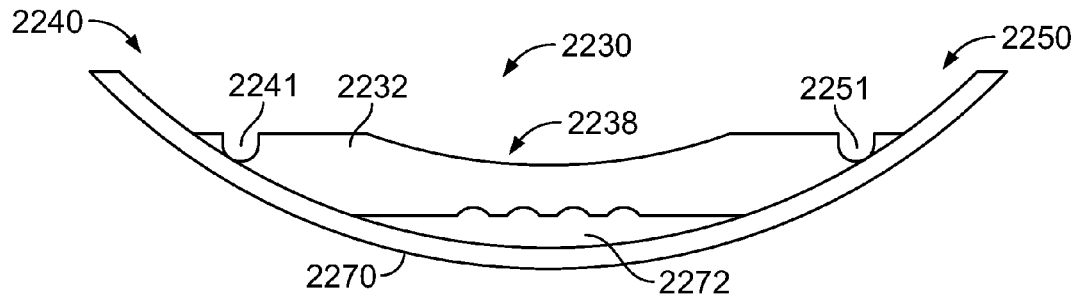
FIG. 22A is a side view of an implant in accordance with another embodiment.
Figure 22B:
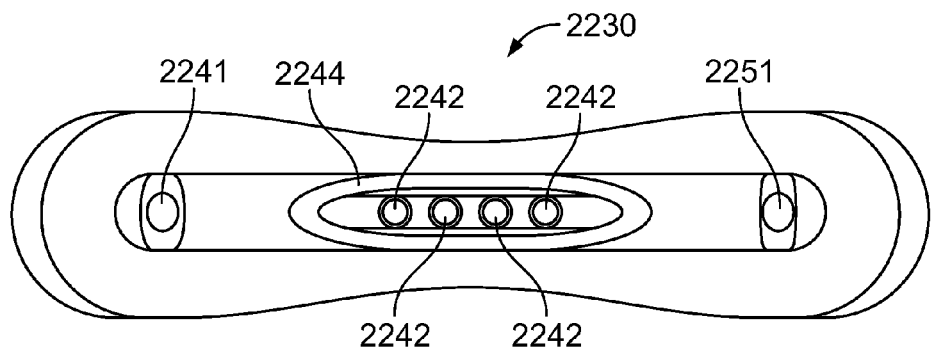
FIG. 22B is another side view of the implant of FIG. 22A.
Figure 22C:
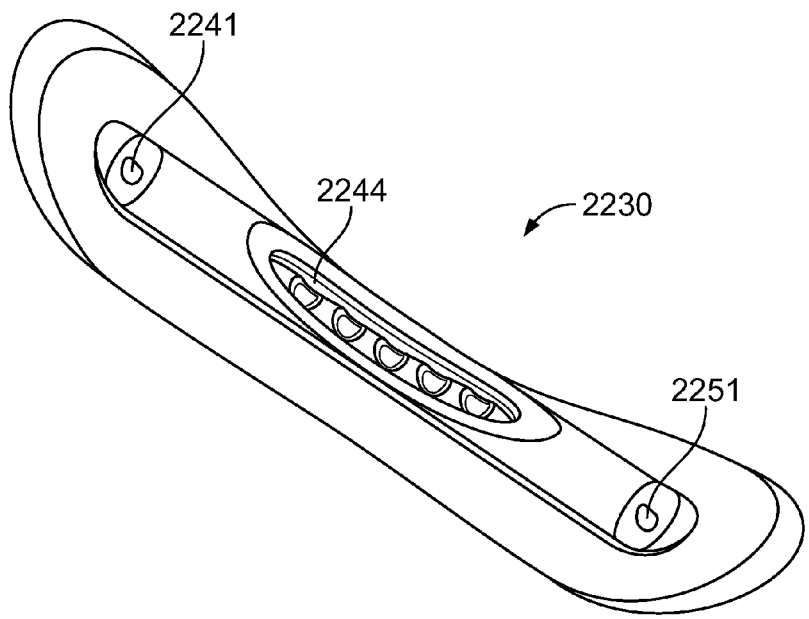
FIG. 22C is a perspective view of the implant of FIG. 22A.

FIGS. 22A through 22C show another version of an implant 2230. Implant 2230 comprises a tube 2232 and a curved support portion 2270. The tube 2232 has an inlet end 2240, an outlet end 2250, and a tube passage 2238 having an inlet 2241 and an outlet 2251.

The tube 2232 has a relatively large side hole 2244 on one side and several smaller side holes 2242 on an opposite side, facing the support portion 2270. The side holes 2242, 2244 can help prevent clogging and assist in fluid flow.

The curved support portion 2270 provides a space 2272 between the tube 2232 and the support portion 2270. The curvature of the support portion 2270 may approximate the curvature of the eye, or it may have a larger or smaller curvature.

The implant 2230 may be implanted in a manner similar to other devices described herein, with the inlet end 2240 in the anterior chamber and the outlet end 2250 draining into or toward the suprachoroidal space. The spacing 2272 between the tube 2232 and the support portion 2270 allows large fluid flow relatively unobstructed by tissue. As this device is completely symmetrical, mounting it on a delivery system may be used to implant the device ab interno and ab externo.

Figure 23A:
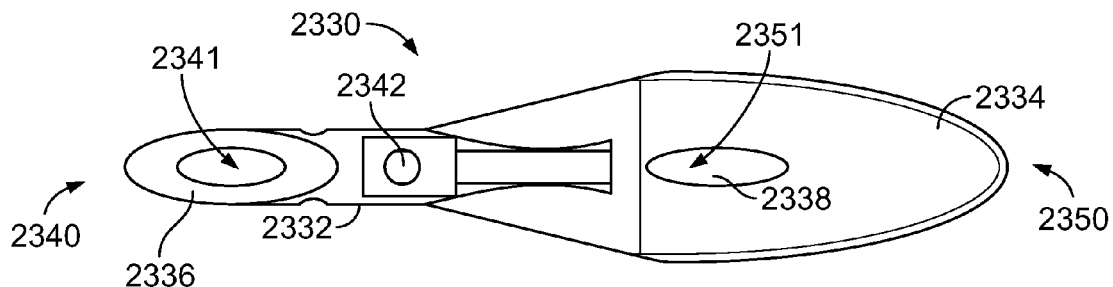
FIG. 23A is a side view of an implant in accordance with another embodiment.
Figure 23B:
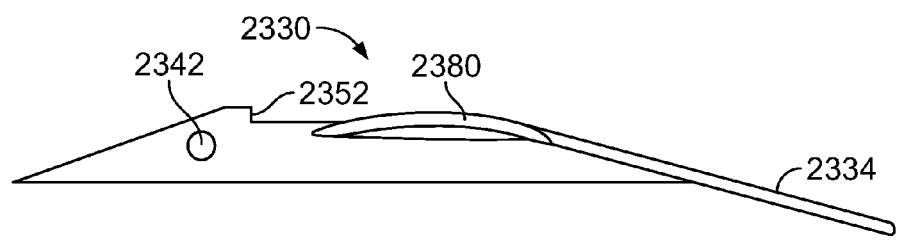
FIG. 23B is another side view of the implant of FIG. 23A.
Figure 23C:
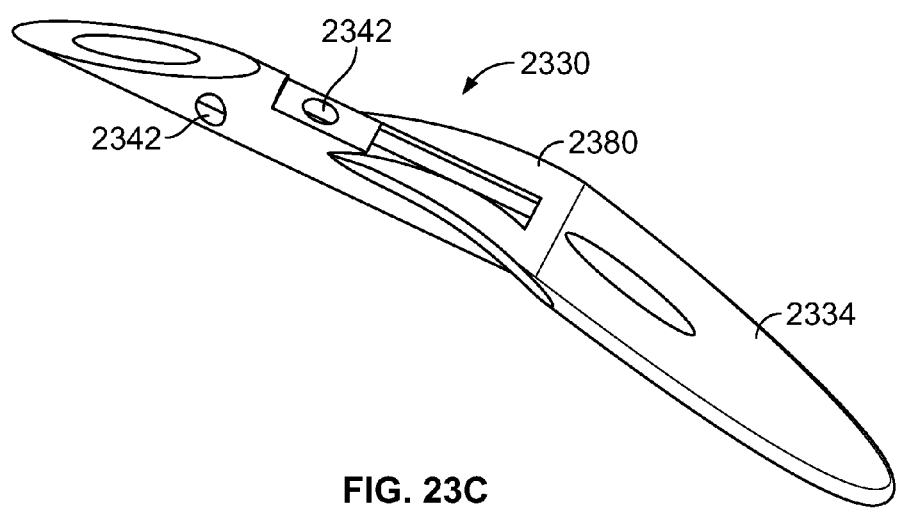
FIG. 23C is a perspective view of the implant of FIG. 23A.

FIGS. 23A through 23C illustrate another embodiment of an implant 2330. The implant 2330 has similarities to the implant 130 in FIG. 1A. Implant 2330 comprises a tube 2332 and an enlarged head, disk or flange 2334. The plane of the flange 2334 forms an angle with the tube 2332. The tube 2332 has an inlet end 2340, an outlet end 2350, and a tube passage 2338 having an axial inlet 2341 and an axial outlet 2351. The flange 2334 is connected to the tube 2332 at its outlet end 2350.

The implant 2330 has one or more side holes 2342, which help prevent clogging, assist in fluid flow and can be used as a marker. The implant 2330 has a beveled surface 2336 at the inlet end 2340. The implant 2330 also has one or more retention projections in the form of one or more spurs 2352 for helping retain the implant 2330 in the eye after insertion.

The flange 2334 may be in a narrow elliptical or oval shape to facilitate insertion through tissue and into the desired location. The angle between the plane of the flange 2334 and the longitudinal axis of the tube 2332 can be relatively small, so that the major axis of the flange 2334 more closely lines up with the longitudinal axis of the tube 2332. The flange 2334 can be relatively large and the flange can have spacers 2380 to help space the tissue at the outlet end away from the outlet flow in order to assist fluid flow.

Figure 24A:
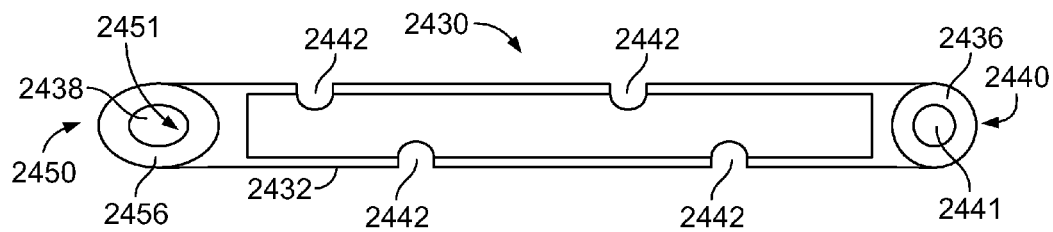
FIG. 24A is a side view of an implant in accordance with another embodiment.
Figure 24B:
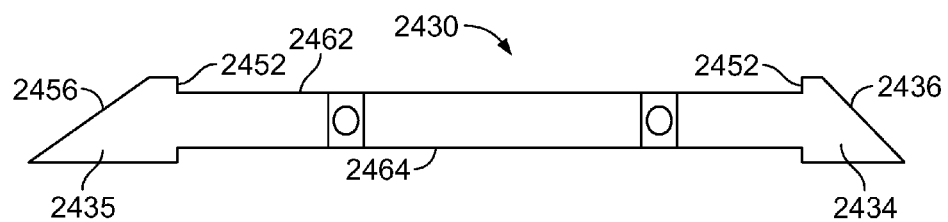
FIG. 24B is another side view of the implant of FIG. 24A.
Figure 24C:
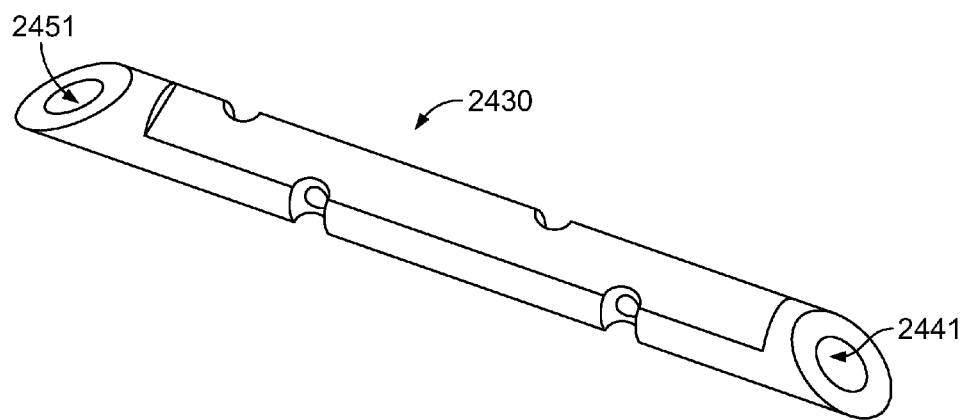
FIG. 24C is a perspective view of the implant of FIG. 24A.

FIGS. 24A through 24C show an implant 2430 similar to the implant 1030 shown in FIGS. 10A through 10D, but with beveled heads at both ends. The implant 2430 comprises a tube 2432 with an inlet end 2440, an outlet end 2450, and a tube passage 2438 with an inlet 2441 and an outlet 2451. The implant 2430 has an enlarged head or flange 2434 at the inlet end 2440 and an enlarged head or flange 2435 at the outlet end 2450. The implant 2430 has one or more side holes 2442, and a reduced profile with flat surfaces 2462, 2464. The side holes 2442 help prevent clogging and allow increased fluid flow.

The implant 2430 has a beveled surface 2436, 2456 at each end. As with other embodiments described herein, the angles of the beveled surfaces 2436, 2456 are selected in accordance with the intended implantation location. In the implant 2430, the angles of the beveled surfaces 2436, 2456 are different from each other. The implant 2430 also has one or more retention projections in the form of one or more spurs 2452 for helping retain the implant 2430 in the eye after insertion.

Figure 25A:
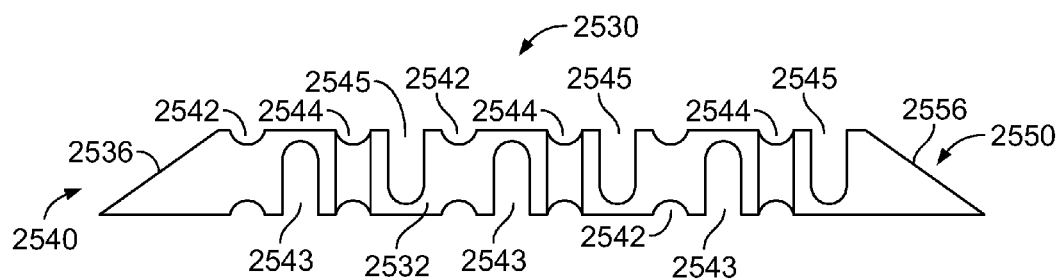
FIG. 25A is a side view of an implant in accordance with another embodiment.
Figure 25B:
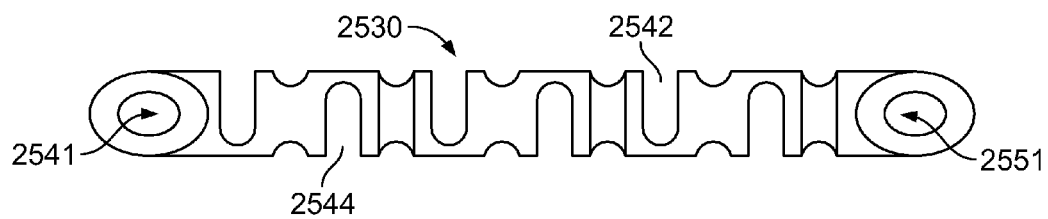
FIG. 25B is another side view of the implant of FIG. 25A.
Figure 25C:
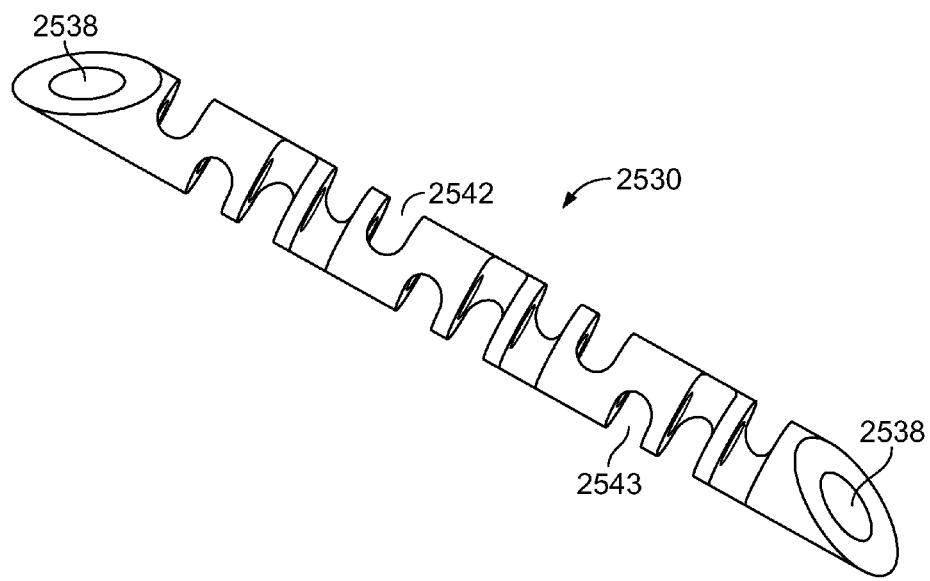
FIG. 25C is a perspective view of the implant of FIG. 25A.

FIGS. 25A through 25C show another embodiment of an implant 2530. The implant 2530 comprises a tube 2532 with an inlet end 2540, an outlet end 2550, and a tube passage 2538 having an inlet 2541 and an outlet 2551. The implant 2430 has a beveled surface 2536, 2556 at each end.

The implant 2530 has a plurality of side holes 2542, 2543, 2544, 2545 along its length. The side holes 2542, 2543, 2544, 2545 are formed by lateral cuts, grooves or channels in the tube 2532 and are staggered in relation to each other. In the implant 2530, each side hole 2542 is formed by a cut, groove or channel that is placed 90 degrees around the tube 2532 from an adjacent cut, groove or channel of an adjacent side hole 2543 and/or 2545. Each side hole 2543 is formed by a cut, groove or channel that is placed 90 degrees around the tube 2532 from an adjacent cut, groove or channel of an adjacent side hole 2542 and/or 2544. Each side hole 2544 is formed by a cut, groove or channel that is placed 90 degrees around the tube 2532 from an adjacent cut, groove or channel of an adjacent side hole 2543 and/or 2545. Each side hole 2545 is formed by a cut, groove or channel that is placed 90 degrees around the tube 2532 from an adjacent cut, groove or channel of an adjacent side hole 2544 and/or 2542.

It will be appreciated that an arrangement of staggered cuts, grooves or channels as in implant 2530 provides flexibility to the tube 2532. For example, in the orientation illustrated in FIG. 25A, bending the two ends downward will open the channels of side holes 2545 and similarly cause some closing of the channels of side holes 2543, allowing the implant 2530 to take on a curvature along its length. With the staggering of the cuts, grooves or channels of the side holes 2542, 2543, 2544, 2545, the implant 2530 can bend in any direction as well as in multiple directions at once. In this way, the implant can more easily conform to the space in which it is implanted.

Figure 26A:
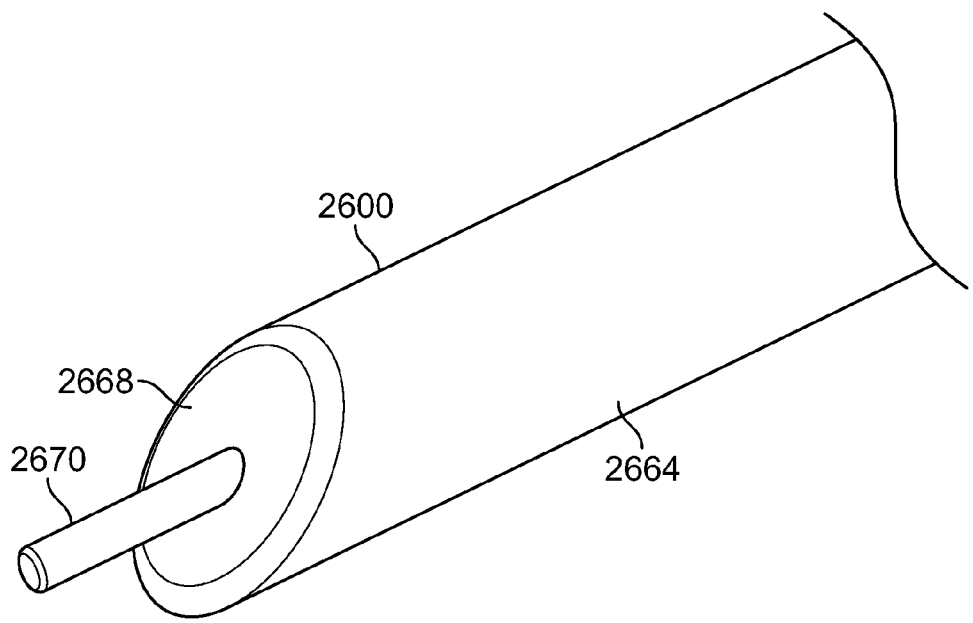
FIG. 26A is a perspective view of an embodiment of a delivery device.
Figure 26B:
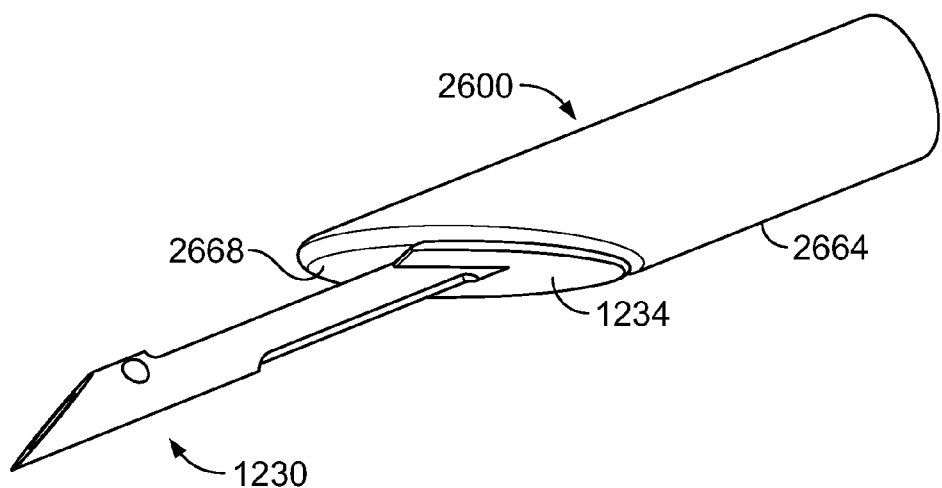
FIG. 26B is a perspective view of the delivery device of FIG. 26A with an implant mounted thereon.

FIGS. 26A and 26B illustrate a delivery device 2600 for inserting an implant into an eyeball. The delivery device 2600 is similar to delivery devices described and illustrated in U.S. patent application Ser. No. 08/975,386, filed Nov. 20, 1997, now U.S. Pat. No. 6,203,513, the disclosure of which, as mentioned above, is incorporated by reference herein.

The delivery device 2600 has a rodlike instrument 2664 such as a needle or probe. The rodlike instrument 2664 has a tip 2670 for penetrating a tube passage of the implant and a retention mechanism for preventing the implant from moving up the delivery device during implantation, for example in the form of an abutment surface 2668 having an angle generally corresponding to that of the flange of the implant. This configuration also prevents rotation of the implant on the delivery device, thereby ensuring proper orientation of the implant in the eyeball. In an alternative embodiment, the retention mechanism may be the tip 2670 of the rodlike instrument, constructed to engage the inside of the tube passage of the implant with a friction fit, thereby preventing the implant from moving up the delivery device during implantation.

Figure 27:
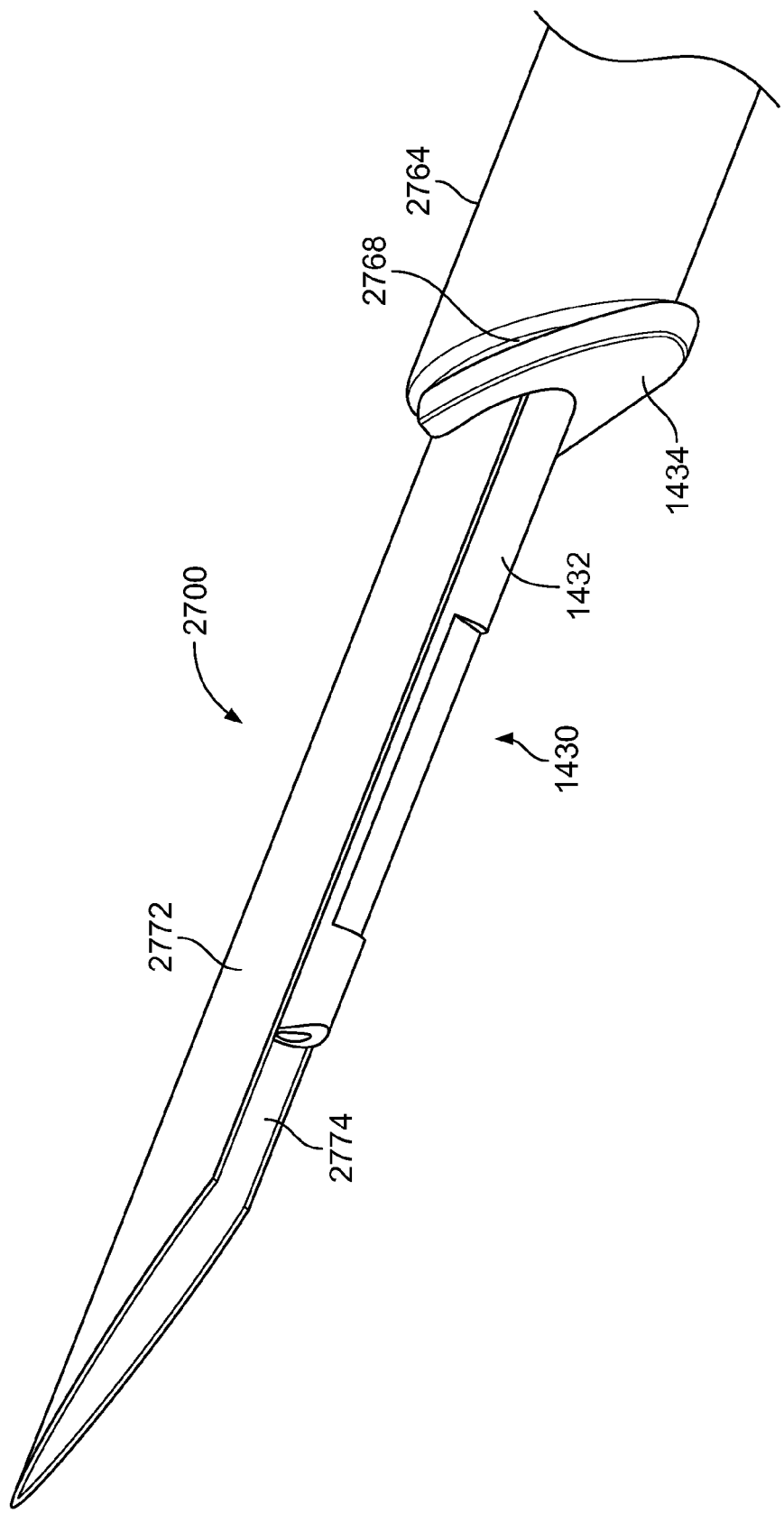
FIG. 27 is a perspective view of another embodiment of a delivery device, carrying an implant.

FIG. 27 illustrates another delivery device 2700 for inserting an implant into an eyeball. The delivery device 2700 has a suitable rodlike instrument 2764 such as a needle or probe. The rodlike instrument 2764 has a wall 2772 with a bore 2774 therein. The tube of the implant fits in the bore 2774, with the flange of the implant projecting outside of the wall 2772. The rodlike instrument 2764 also has a retention mechanism for preventing the implant from moving up the delivery device during implantation, for example in the form of an abutment surface 2768 having an angle generally corresponding to that of the flange of the implant.

Figure 28A:
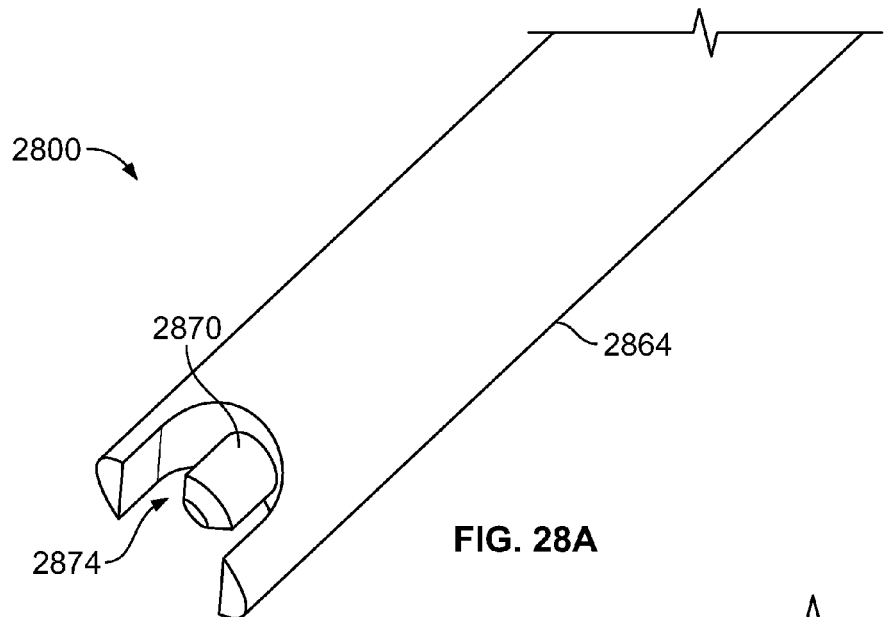
FIG. 28A is a perspective view of another embodiment of a delivery device.
Figure 28B:
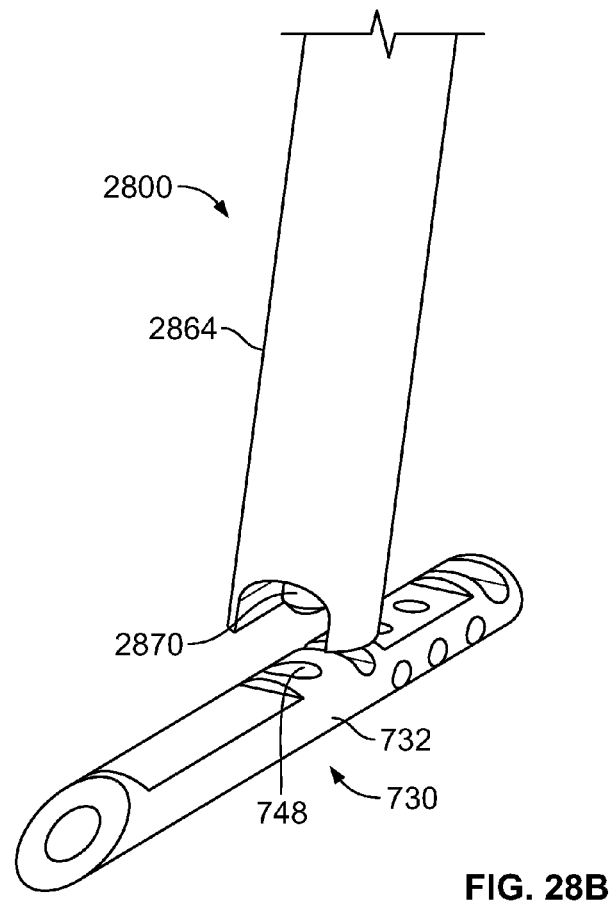
FIG. 28B is a perspective view of the delivery device of FIG. 28A, being attached to an implant.

FIGS. 28A and 28B illustrate another delivery device 2800 for inserting an implant into an eyeball. The delivery device 2800 has a suitable rodlike instrument 2864 such as a needle or probe. The rodlike instrument 2864 has a recess 2874 for accommodating the tube of the implant and a tip 2870 for inserting into a hole in the implant. The delivery device 2800 can grip the implant when the tip 2870 is inserted into the hole in the implant.

Delivery devices such as those illustrated in FIGS. 28 and 29 of U.S. patent application Ser. No. 08/975,386 may also be used to deliver implants as described herein. In those figures, the delivery device 110 has a handle (not shown) and a rodlike instrument 112. The rodlike instrument 112 has central bore 114 in which is located a retractable wire 116. The retractable wire 116 is positioned for penetrating a tube passage 102 of the implant 100 when the implant 100 is attached to the delivery device 110. The delivery device 110 has a retention mechanism including an abutment surface 118 having an angle generally corresponding to that of the disk 106 of the implant 100 for preventing the implant 100 from moving up the delivery device 110 during implantation and a hook 120 for preventing the implant 100 from moving down the wire 116.

For implantation, the implant 100 is placed over the wire 116 with the wire 116 projecting into the tube passage 102 and with the abutment surface 118 abutting against the disk 106 with the hook 120 retaining the disk 106 round the opposite side. FIG. 28 of U.S. patent application Ser. No. 08/975,386 illustrates the end of the delivery device 110 in this condition, with the retention wire 116 in its forward position.

After the implant is in position, the retention wire 116 is retracted out of the implant 100. FIG. 29 of U.S. patent application Ser. No. 08/975,386 illustrates the end of the delivery device 110 with the retention wire retracted. With the retention wire retracted, the implant is free to slide away from the hook 120, allowing the delivery device 110 to be withdrawn, leaving the implant in place.

Figure 29A:
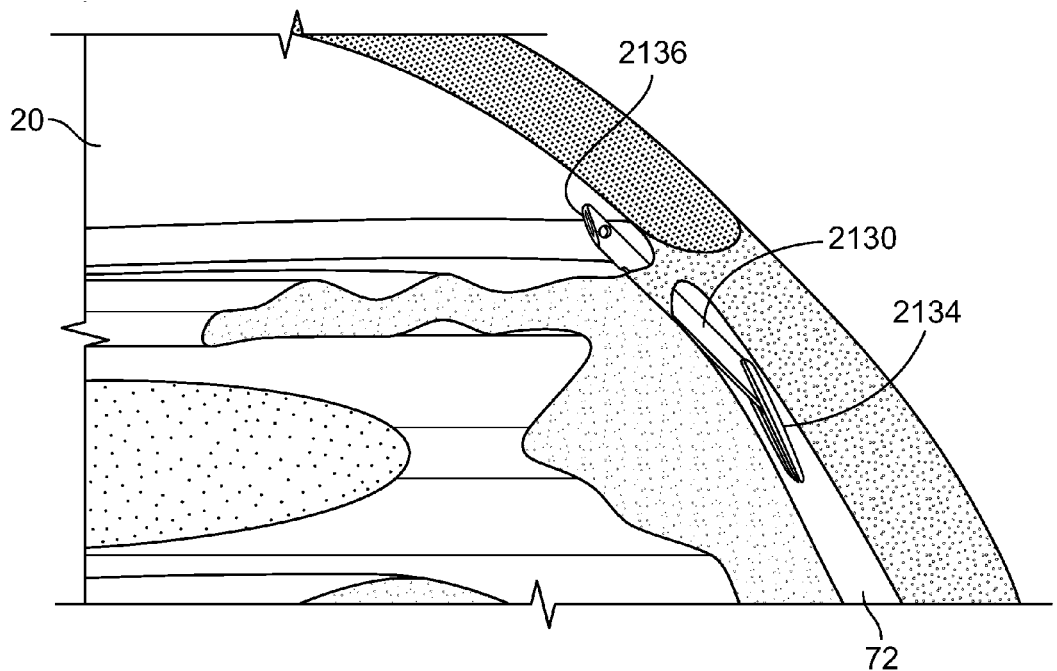
FIG. 29A shows an implant positioned for drainage from the anterior chamber to a suprachoroidal space.
Figure 29B:
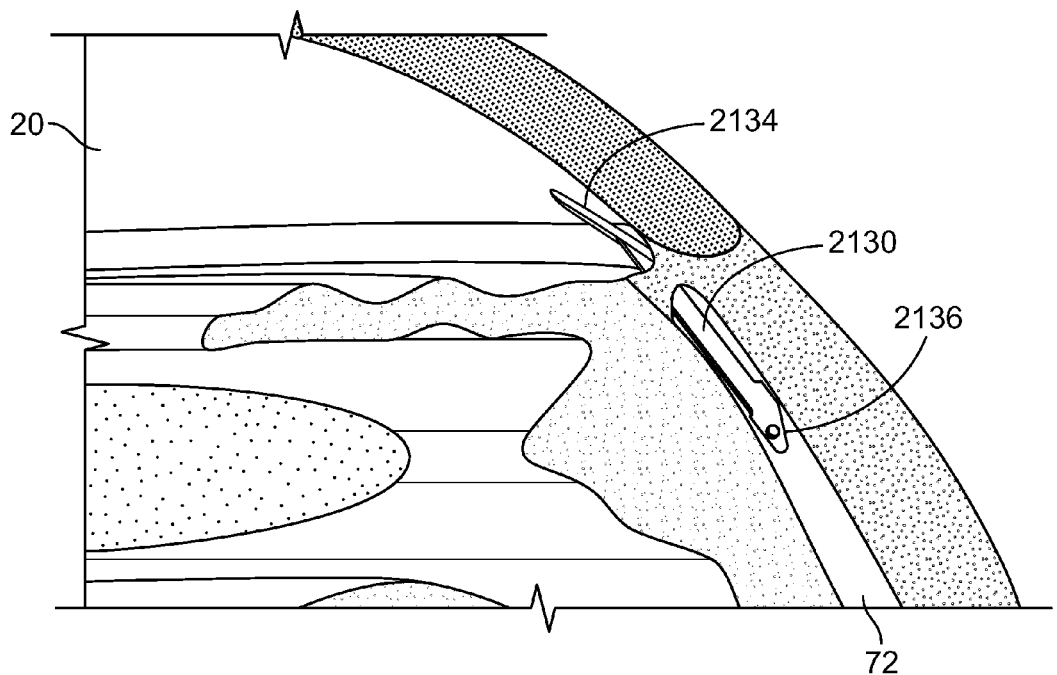
FIG. 29B shows the implant of FIG. 29A with the positions of its inlet end and outlet end reversed, again positioned for drainage from the anterior chamber to a suprachoroidal space.
Figure 30A:
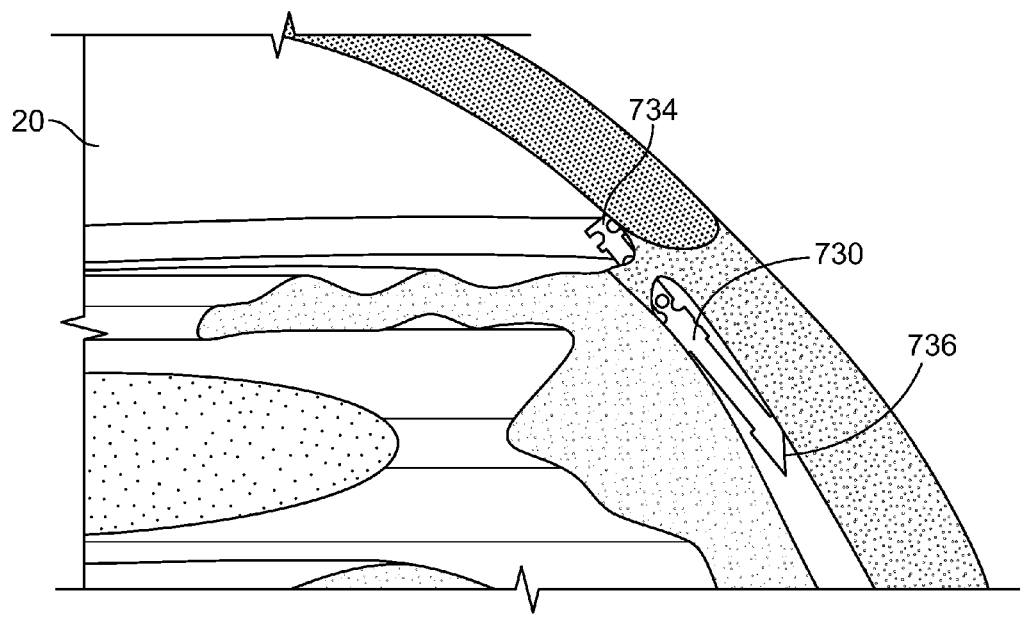
FIG. 30A shows another implant positioned for drainage from the anterior chamber to a suprachoroidal space.
Figure 30B:
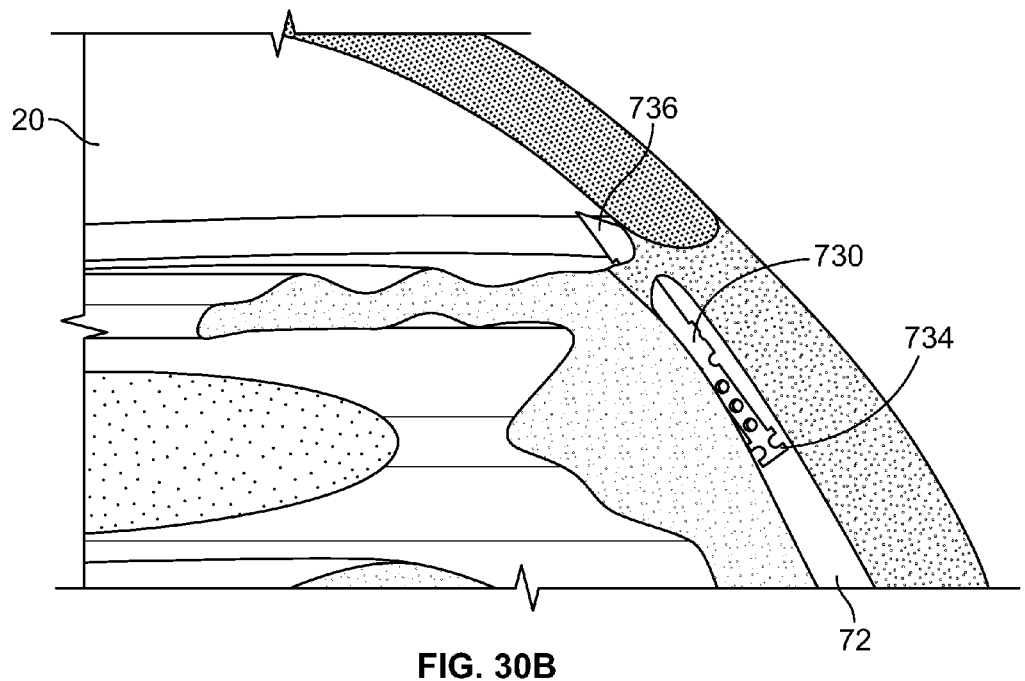
FIG. 30B shows the implant of FIG. 30A with the positions of its inlet end and outlet end reversed, again positioned for drainage from the anterior chamber to a suprachoroidal space.

It will be appreciated that implants as described herein can support flow in either direction. Thus, the inlet ends as described herein may be used as outlet ends, and vice versa. For example, FIGS. 29A and 29B show an implant 2130 in a first position in FIG. 29A and in a reversed position in FIG. 29B. Similarly, FIGS. 30A and 30B show an implant 730 in a first position in FIG. 30A and in a reversed position in FIG. 30B.

Figure 31:
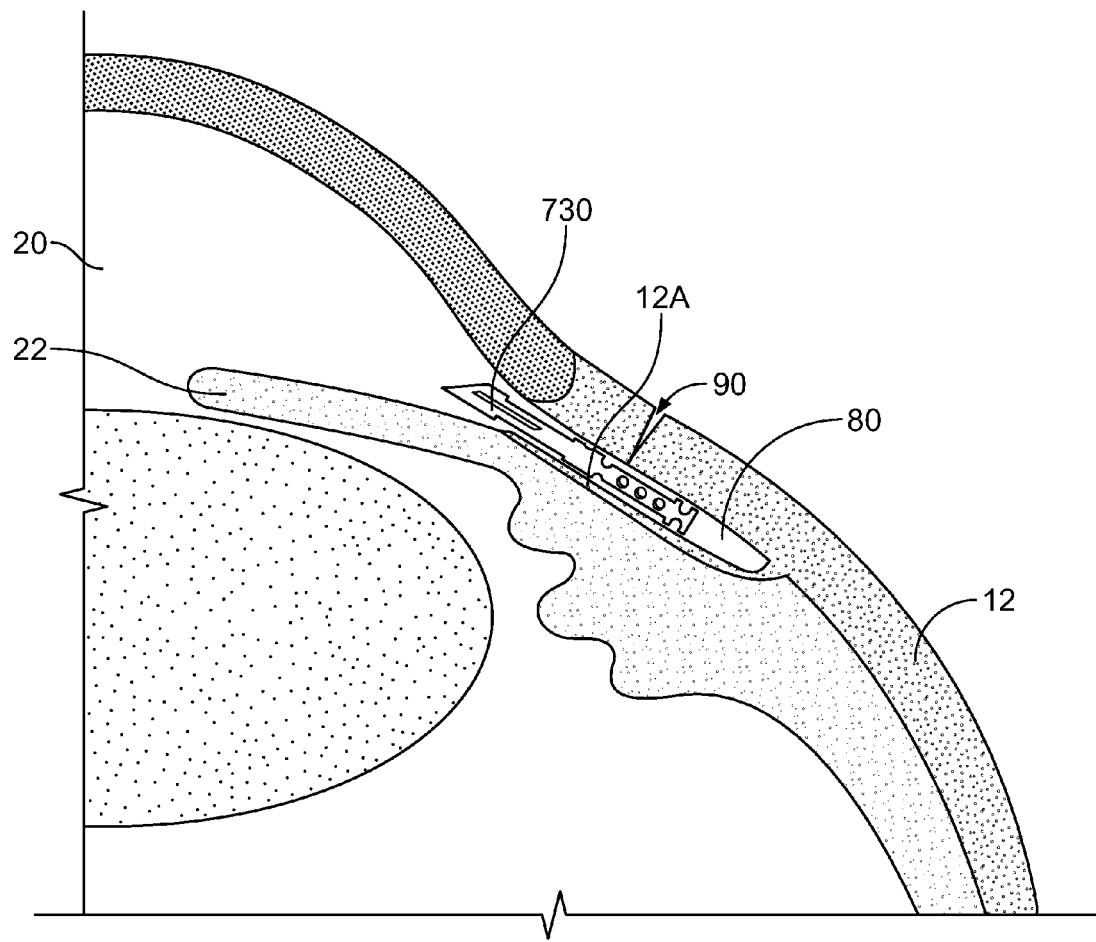
FIG. 31 shows an implant positioned for drainage from the anterior chamber to a juxta-uveal space.

In addition to draining from the anterior chamber to the suprachoroidal space, the implants as described herein may also provide drainage to a "juxta-uveal" location. This is illustrated in FIG. 31. The juxta-uveal location is a pocket 80 within scleral tissue 12, separated from the choroid by a thin layer 12A of scleral tissue. When implanted in the juxta-uveal location 80, the implant is positioned with its inlet end in the anterior chamber 20 of the eye and its outlet end in the pocket 80 that is formed during the procedure in the juxta-uveal portion of the sclera 12, leaving a thin layer 12A of sclera between the device and the choroid, such that the implant is near the choroid but not in direct contact with the choroid. When implanted in this juxta-uveal location, no part of the implant would be in direct contact with either the choroid or ciliary tissue. The placement of the outlet end within the scleral tissue, as opposed to in contact with the choroid, is believed to have the advantage of avoiding the risks of bleeding, hypotony and fibrosis that can be associated with the choroid.

Implantation of implants as described herein can be performed as follows. First, the implant is mounted on, attached to, or otherwise loaded in or on a suitable delivery device, such as a delivery device as described herein.

In an example ab externo method, a physician forms an incision in the sclera from outside the eye. Alternatively, the implant itself or the delivery device may be penetrated into the eye to form the incision. The implant is directed through the incision to the intended implantation location.

The incision can be made in a location such that the inlet end is advanced first as the leading end during implantation or such that the outlet end is advanced first as the leading end during implantation. Alternatively, the incision may be made in an intermediate location, for example at a location similar to that of incision 90 in FIG. 31. Then one end of the implant may be put through the incision and generally into position, after which the other end of the implant may be put through the incision and tucked into position. To facilitate putting the second end through the incision, the first end may be forced further distally and/or the tissue may be stretched.

Once the implant is in position, the delivery device is withdrawn, leaving the implant in place. If desired, the incision can be closed with a suture or sutures.

In an example ab interno method, a physician forms an incision in the eye, generally in the cornea or sclera. Alternatively, the implant itself or the delivery device may be penetrated into the eye to form the incision. The physician then advances the implant through the incision, into and across the anterior chamber, to the intended implantation location. The outlet end of the implant is penetrated into the trabecular meshwork or other tissue through which the implant is to be implanted. If desired, an incision or hole can be made in the trabecular meshwork or other tissue before advancing the implant therethrough.

Once the implant is in position, the delivery device is withdrawn, leaving the implant in place. If desired, the incision in the cornea or sclera can be closed with a suture or sutures.

An implant constructed in accordance with the disclosure may be manufactured entirely from or covered with any suitable material such as stainless steel, silicon, gold, nitinol, Teflon, tantalum, PMMA, or any other suitable plastic, metal or other material. The implant may also be coated with heparin or any other suitable biologically active compound.

An implant in accordance with the disclosure may be manufactured in various ways. The tube may be formed from the tip of a standard stainless steel hypodermic needle or similar tube. The various holes, cuts, grooves, channels and/or surfaces may be formed by removing material from the tube.

One alternative method for manufacturing an implant according to the invention is illustrated in FIGS. 17 through 19 of U.S. patent application Ser. No. 08/975,386. FIG. 17 shows an initial step of the process in which an outer tube 74 having a longitudinal bore is cut into the illustrated pattern. In a next step of the process, illustrated in FIG. 18 of U.S. patent application Ser. No. 08/975,386, a smaller inner tube 90 is placed inside the longitudinal bore of the remaining portion or portions of the outer tube 74. The inner tube 90 has an outer diameter that generally corresponds to the inner diameter of the outer tube 74. When the inner tube 90 is placed inside the outer tube 74, the two tubes may be secured together, for example by welding the tubes together at the areas identified by reference numerals 86 and 88. After the two tubes are joined together, further cuts are made to form the implant as shown in FIG. 19. This step includes simultaneously cutting the outer tube and inner tube along an angled plane at the outlet end of the implant to form the upper surface of the disk 84 and to cut away the unwanted portion of the inner tube 90 that would otherwise have projected beyond that upper surface of the disk 84. The portion of the inner tube 90 that remains after these final cuts forms the implant shaft. The portions of the outer tube 74 that remain after these final cuts form the retention projection 82 and the disk 84. As a variation of this method, all or most of the cuts can be made after the smaller tube is placed inside the larger tube.

It will be appreciated by persons having ordinary skill in the art that variations on this manufacturing process and other manufacturing processes are possible. For example, an implant made of plastic may be manufactured by a suitable molding operation.

As described in U.S. patent application Ser. No. 08/975,386, various mechanisms may be used, if desired, for giving different flow characteristics to the implant. It may be desirable to use implants with different flow characteristics for different patients and/or to have an implant in which the flow characteristics may be changed after implantation in a particular patient. FIGS. 20 through 27 of U.S. patent application Ser. No. 08/975,386 illustrate various mechanisms for assisting in controlling the flow of fluid, e.g. aqueous humors, through an implant. These mechanisms may be used with other implants as described herein.

As will be appreciated by persons having ordinary skill in the art, the various embodiments described herein are given by way of example only. Various changes, modifications and variations may be applied to the described embodiments without departing from the scope of the invention, as defined by the appended claims.

The invention claimed is:

1. A method of implanting an intraocular implant, comprising:
   (i) positioning an intraocular implant to be carried by a delivery device;
   wherein the intraocular implant comprises a tube having an inlet end, an outlet end, and a tube passage;
   wherein the inlet end is adapted to extend into the anterior chamber of the eye;
   wherein the outlet end is adapted to be implanted adjacent scleral tissue of the eye;
   wherein the implant further comprises a flange at one end of the tube, and wherein a surface of the flange is tilted at a first angle relative to a plane perpendicular to a longitudinal axis of the tube; wherein the delivery device comprises a rodlike instrument and a retention mechanism, wherein the retention mechanism comprises an abutment surface tilted at a second angle relative to a plane perpendicular to a longitudinal axis of the rodlike instrument, wherein the second angle generally corresponds to the first angle;
   (ii) forming an incision in the eye;
   (iii) directing the implant to a desired implantation location; and
   (iv) withdrawing the delivery device.

2. A method according to claim 1, wherein the intraocular implant further comprises one or more side holes.

3. A method according to claim 1, wherein the intraocular implant further comprises a beveled surface at one end of the tube.

4. A method according to claim 1, wherein the intraocular implant further comprises one or more retention projections in the form of one or more spurs.

5. A method according to claim 1, wherein the delivery device comprises a tip for penetrating a tube passage of the implant.

6. A method according to claim 1, wherein the retention mechanism of the delivery device is adapted for preventing the implant from moving up the delivery device during implantation.

7. An intraocular implant in combination with a delivery device, comprising:
   an intraocular implant comprising a tube having an inlet end, an outlet end, and a tube passage, wherein the inlet end is adapted to extend into the anterior chamber of the eye, wherein the outlet end is adapted to be implanted adjacent scleral tissue of the eye, wherein the implant further comprises a flange at one end of the tube, and wherein a surface of the flange is tilted at a first angle relative to a plane perpendicular to a longitudinal axis of the tube; and
   a delivery device comprising a rodlike instrument and a retention mechanism, wherein the retention mechanism comprises an abutment surface tilted at a second angle relative to a plane perpendicular to a longitudinal axis of the rodlike instrument, wherein the second angle generally corresponds to the first angle;
   wherein the intraocular implant is carried by the delivery device.

8. A combination of intraocular implant and delivery device according to claim 7, wherein the intraocular implant further comprises one or more side holes.

9. A combination of intraocular implant and delivery device according to claim 7, wherein the intraocular implant further comprises a beveled surface at one end of the tube.

10. A combination of intraocular implant and delivery device according to claim 7, wherein the intraocular implant further comprises one or more retention projections in the form of one or more spurs.

11. A combination of intraocular implant and delivery device according to claim 7, wherein the delivery device comprises a tip for penetrating a tube passage of the implant.

12. A combination of intraocular implant and delivery device according to claim 7, wherein the retention mechanism of the delivery device is adapted for preventing the implant from moving up the delivery device during implantation.

* * * * *